(12) United States Patent
Anderson et al.

(10) Patent No.: US 9,931,210 B2
(45) Date of Patent: Apr. 3, 2018

(54) VARIABLE ANGLE BLADE AUGMENT

(71) Applicant: Smith & Nephew, Inc., Memphis, TN (US)

(72) Inventors: Jennifer Kristin Anderson, Cordova, TN (US); Jeffrey Joel Shea, Memphis, TN (US); Richard Douglas Lambert, Collierville, TN (US); Michael Scott Bennett, Southaven, MS (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 15/458,701

(22) Filed: Mar. 14, 2017

(65) Prior Publication Data

US 2017/0181856 A1  Jun. 29, 2017

Related U.S. Application Data

(63) Continuation-in-part of application No. 15/026,778, filed as application No. PCT/US2015/062649 on Nov. 25, 2015.

(Continued)

(51) Int. Cl.
  *A61F 2/34* (2006.01)
  *A61F 2/30* (2006.01)
  *A61F 2/46* (2006.01)

(52) U.S. Cl.
  CPC ...... *A61F 2/30734* (2013.01); *A61F 2/30771* (2013.01); *A61F 2/34* (2013.01);
  (Continued)

(58) Field of Classification Search
  CPC ...... A61F 2/30; A61F 2/32; A61F 2/34; A61F 2/30767; A61F 2/30734; A61F 2/30385;
  (Continued)

(56) References Cited

U.S. PATENT DOCUMENTS 5,176,711 A * 1/1993 Grimes .............. A61B 17/1666
                                                  623/22.22
5,916,268 A * 6/1999 Schollner ........... A61B 17/1746
                                                  623/22.36

(Continued)

FOREIGN PATENT DOCUMENTS

DE      4133433 C1    5/1993
EP      0628294 A1    12/1994
WO    2013086235 A1    6/2013

OTHER PUBLICATIONS

International Search Report; European Patent Office; International Application No. PCT/US2015/062649; Feb. 17, 2016; 4 pages.

(Continued)

*Primary Examiner* — Alvin Stewart
(74) *Attorney, Agent, or Firm* — Taft Stettinius & Hollister LLP

(57) ABSTRACT

A variable angle blade augment including an augment component and a blade component. The blade component includes a buttress portion and a neck portion, with the neck portion having a body segment and a face segment that is contoured for mating engagement with an outer surface of the acetabular shell. The augment component has a first opening sized and shaped to receive insertion of the body segment, and which is also sized to accommodate selective adjustment of, when the body segment is positioned in the first opening, linear and angular orientations of the blade component relative to the augment component. Additionally, the body segment has a length that is sized to facilitate direct contact of the face segment with the acetabular shell when the variable angle blade augment is in an assembled configuration. Further, cement can be injected into the internal cavity to unitize the connection between the acetabular shell and the blade component.

24 Claims, 23 Drawing Sheets

Related U.S. Application Data

(60) Provisional application No. 62/084,919, filed on Nov. 26, 2014.

(52) U.S. Cl.
CPC ............... *A61F 2002/3055* (2013.01); *A61F 2002/3069* (2013.01); *A61F 2002/30385* (2013.01); *A61F 2002/30434* (2013.01); *A61F 2002/30518* (2013.01); *A61F 2002/30542* (2013.01); *A61F 2002/30578* (2013.01); *A61F 2002/30604* (2013.01); *A61F 2002/30736* (2013.01); *A61F 2002/30784* (2013.01); *A61F 2002/4631* (2013.01)

(58) Field of Classification Search
CPC .. A61F 2002/30736; A61F 2002/30738; A61F 2002/30537; A61F 2002/3054; A61F 2002/3055; A61F 2002/30553; A61F 2002/30604
See application file for complete search history.

(56) References Cited

U.S. PATENT DOCUMENTS

| | | | | | |
|---|---|---|---|---|---|
| 6,162,257 | A * | 12/2000 | Gustilo | ................. | A61B 17/15 623/22.32 |
| 6,340,370 | B1 * | 1/2002 | Willert | ..................... | A61F 2/34 623/22.21 |
| 6,454,809 | B1 * | 9/2002 | Tornier | ............... | A61F 2/30724 623/22.32 |
| 6,818,019 | B2 * | 11/2004 | Horber | ................. | A61F 2/4014 403/90 |
| 7,011,686 | B2 * | 3/2006 | Ball | .................... | A61F 2/4014 623/19.14 |
| 7,695,473 | B2 * | 4/2010 | Ralph | ................ | A61B 17/8023 606/71 |
| 7,740,661 | B2 * | 6/2010 | Baratz | .................. | A61F 2/3804 623/20.11 |
| 8,114,091 | B2 * | 2/2012 | Ratron | ................... | A61B 17/15 606/86 R |
| 8,597,365 | B2 * | 12/2013 | Meridew | .................... | A61F 2/34 623/22.32 |
| 8,663,333 | B2 * | 3/2014 | Metcalfe | .............. | A61F 2/4014 623/19.11 |
| 8,828,089 | B1 * | 9/2014 | Perez | .................. | A61F 2/30734 606/91 |
| 9,345,576 | B2 * | 5/2016 | Shea | ................... | A61F 2/30734 |
| 9,474,618 | B2 * | 10/2016 | Bickley | ..................... | A61F 2/40 |
| 2008/0021568 | A1 * | 1/2008 | Tulkis | ................. | A61F 2/30734 623/22.35 |
| 2009/0204225 | A1 * | 8/2009 | Meridew | ............. | A61F 2/30734 623/22.21 |
| 2009/0326670 | A1 * | 12/2009 | Keefer | ................ | A61F 2/30734 623/22.22 |
| 2013/0035766 | A1 * | 2/2013 | Meridew | ................... | A61F 2/34 623/22.21 |
| 2014/0343686 | A1 * | 11/2014 | Shea | .................... | A61F 2/30734 623/23.43 |
| 2015/0351917 | A1 * | 12/2015 | Link | ................... | A61F 2/30734 623/22.11 |
| 2016/0262895 | A1 * | 9/2016 | Shea | .................. | A61F 2/30734 |
| 2016/0278925 | A1 * | 9/2016 | Roby | ................. | A61F 2/30734 |
| 2016/0317308 | A1 * | 11/2016 | Shea | ................. | A61F 2/30734 |
| 2017/0181856 | A1 * | 6/2017 | Anderson | .......... | A61F 2/30734 |

OTHER PUBLICATIONS

Written Opinion of the International Searching Authority; European Patent Office; International Application No. PCT/US2015/062649; 6 pages.

* cited by examiner

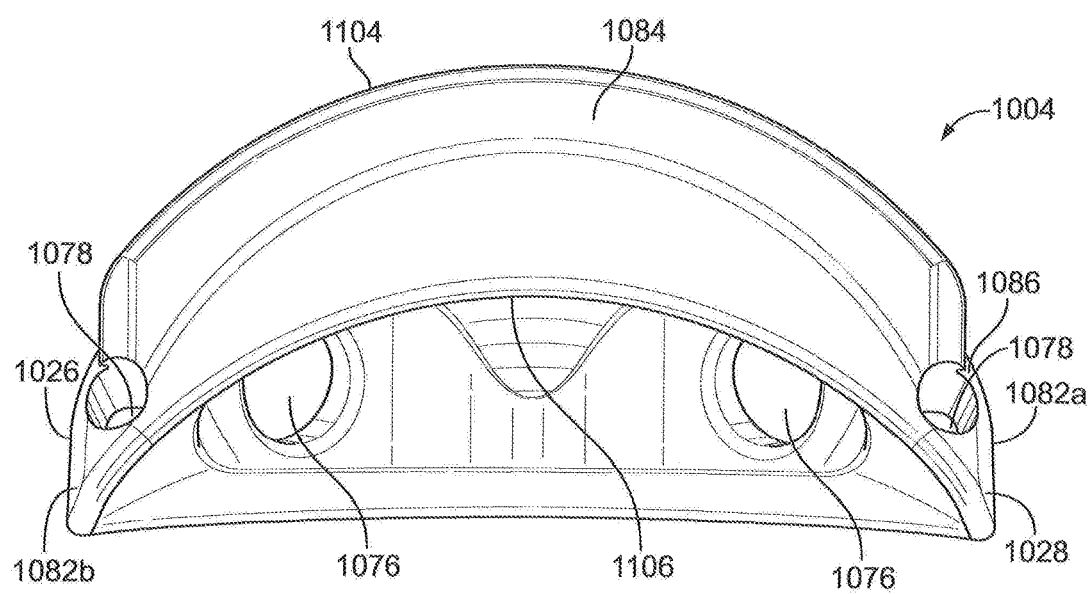
FIG. 9E
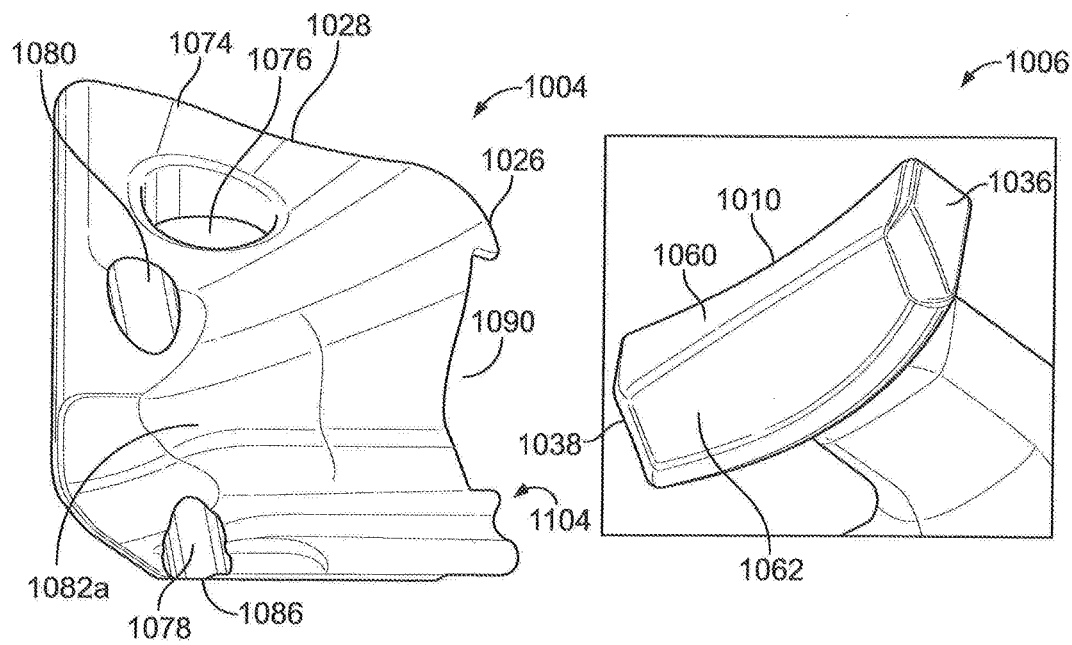
FIG. 9F
FIG. 9G

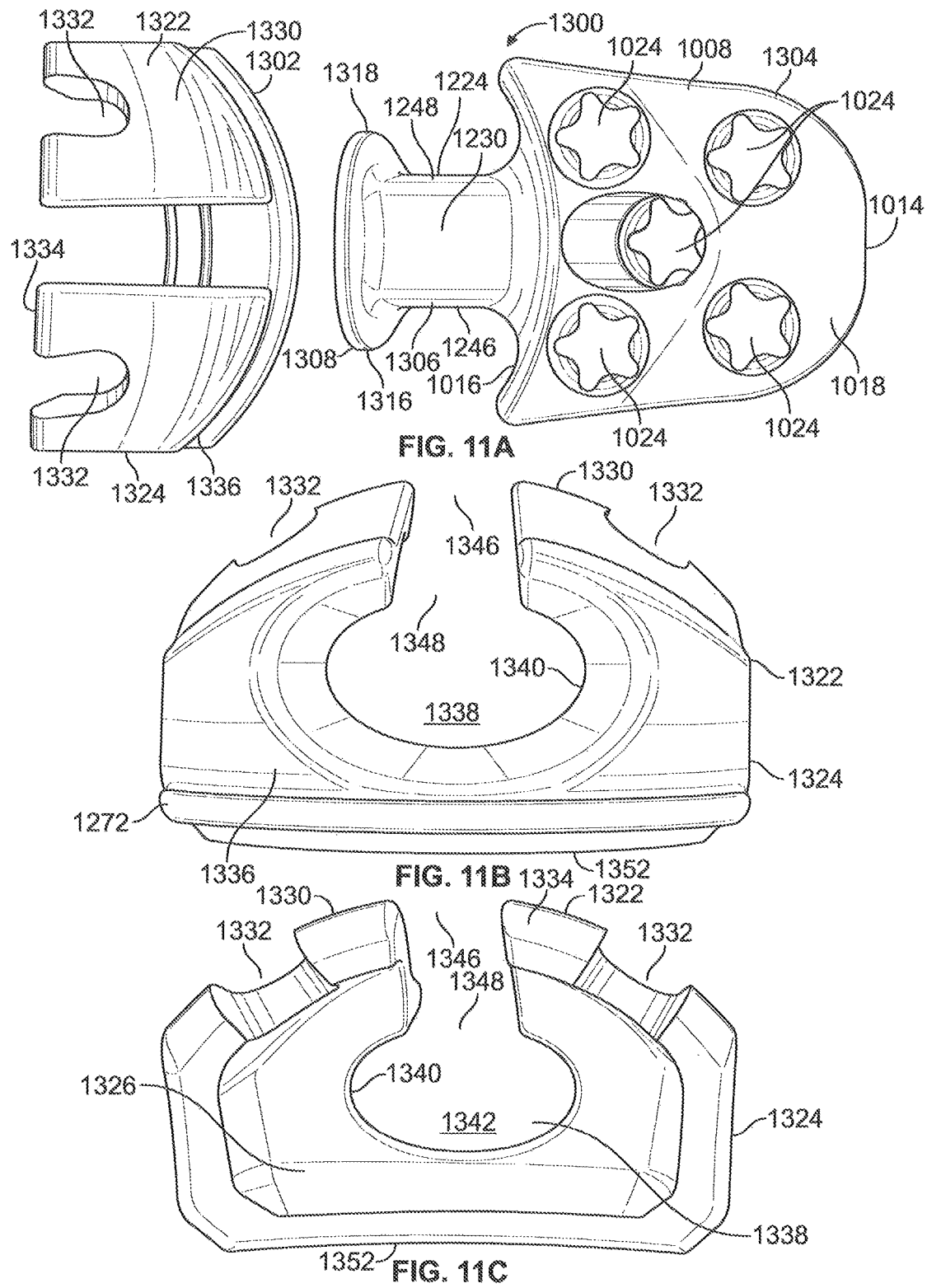

VARIABLE ANGLE BLADE AUGMENT

CROSS-REFERENCE TO RELATED APPLICATIONS

The present application is a continuation-in-part of U.S. patent application Ser. No. 15/026,778 filed Apr. 1, 2016, which is a U.S. National Phase of International PCT Application No. PCT/US2015/062649 filed Nov. 25, 2015, which claims the benefit of U.S. Provisional Patent Application No. 62/084,919 filed Nov. 26, 2014, the contents of each application hereby incorporated by reference in their entirety.

BACKGROUND

Embodiments of the present invention generally relate to the field of implantable orthopedic medical devices. More particularly, but not exclusively, embodiments of the present invention relate to implants for revision acetabular surgery.

Joints often undergo degenerative changes that necessitate replacing the joint with a prosthetic joint. For example, the hip joint may be replaced with two bearing surfaces between the femoral head and the acetabulum. The first bearing surface is often a prosthesis shell or acetabular cup having a liner that provides an inner bearing surface that receives and cooperates with an artificial femoral head in an articulating relationship to track and accommodate relative movement between the femur and the acetabulum.

In at least some instances, a second or subsequent surgery may be performed to replace a prosthetic joint with another replacement prosthetic joint. Such replacement of the original prosthetic joint may be performed for a number of reasons including, for example, the need to remove diseased or degenerated bone. Further, these additional surgeries often require the replacement of the original prostheses with a larger or enhanced prosthetic joint, often referred to as a revision prosthesis. With respect to acetabular revision surgery, an acetabular prosthesis may include additional mounting elements such as, for example, augments that provide additional support and/or stability for the replacement prosthesis. These additional mounting or attachment members are often required due to bone degeneration, bone loss or bone defects in the affected area (i.e., the hip joint). Moreover, such bone deficiencies or defects often present challenges in attaining optimized and structurally sound prosthetic fixation to the host bone. Accordingly, mounting members may be provided in conjunction with a prosthesis system in order to aid the surgeon in achieving optimal fixation of the prosthetic joint, or a component of the prosthetic joint, to a bone of the patient.

Prior attempts to provide such mounting attachments (i.e., augments) with modularity have often fallen short, and instead typically provide a few discrete positions at which the mounting members may be positioned. For example, an ongoing challenge is to align implantable medical devices such as, for example, reconstructive devices, to the natural physiology of a patient. Proper alignment often may at least assist in attaining optimal wear resistance and optimal performance for many devices. Yet, patient anatomical variations present challenges in providing a medical device that may be properly aligned for each patient. For example, contemporary medical devices that address complex revision acetabular surgery may include multiple buttress augment designs that are dedicated for supporting particular sides or areas of the acetabular cup. Yet, the buttress surface of augments is typically shaped or contoured along a fixed angle or angles. Further, such fixed angles often provide an optimal match for the variations for only some patients' anatomies, and may not allow for an optimal match with other patients' anatomies.

Limitations relating to the available angles at which augment devices may be aligned, as well as augment devices having separated hand or orientation designations, among other limitations, often provide obstacles to both the installation and cost of these types of implantable medical devices. For example, medical implants that are provided in multiple directional or hand orientations may add complexity to the surgical procedure. Moreover, the time associated with at least the selection and confirmation that the correct hand side configuration of the medical device has been selected for implantation in a patient may reduce the time available to the surgeon to attain proper alignment and/or positioning of all of components of the medical device during the implantation procedure. Additionally, different hand configurations may increase the costs associated with procuring, storing, and/or otherwise having readily available an appropriate quantity of implantable devices. Moreover, the time and effort during surgery to properly match the fixed angles of buttress surfaces and the acetabular cup with the patient's particular anatomy may adversely impact the time available to the surgeon to address other aspects of the implantation procedure.

Thus, there remains a need for improved orthopedic medical devices for use in revision acetabular surgeries. The present invention addresses this need and provides other benefits and advantages in a novel and non-obvious manner.

SUMMARY

In one form of the invention, an implantable variable angle blade augment is provided to support an acetabular shell, and includes a blade component and an augment component. The blade component includes a buttress portion and a neck portion, with the neck portion having a body segment and a face segment. The augment component having a first opening extending through a top side portion of the augment component and a second opening extending through a bottom side portion of the augment component, the first opening and the second opening being on opposing sides of, and in fluid communication with, an internal cavity of the augment component, the first opening sized to accommodate selective adjustment of at least one of a linear orientation and an angular orientation of the blade component relative to the augment component when the body segment is positioned in the first opening, the neck portion having a length that is sized to position, when the body segment is positioned in the first opening, the face segment at a location at least proximally adjacent to the second opening such that, when the bottom side portion is positioned adjacent to the acetabular shell, a portion of the face segment directly engages an outer surface of the acetabular shell.

In another form of the invention, an implant system is provided which includes an acetabular shell having an outer surface, and a variable blade augment. The variable blade augment includes a blade component and an augment component. The blade component has a buttress portion and a neck portion, with the neck portion having a body segment and a face segment. The augment component has a first opening extending through a top side portion of the augment component and a second opening extending through a bottom side portion of the augment component, with the top and bottom sides being on opposing sides of the augment component, and with the bottom side shaped for mating engagement with the outer surface of the acetabular shell. The first opening and the second opening are in fluid communication with an internal cavity of the augment component, with the first opening sized and shaped to receive at least a portion of the body segment and accommodate selective adjustment of at least one of a linear orientation and an angular orientation of the blade component relative to the augment component when the body segment is positioned in the first opening. The neck portion has a length that is sized to extend the body segment through the first opening and into the internal cavity by a length that positions a portion of the face segment at a location that is at least proximally adjacent to the second opening such that, when the bottom side portion is positioned adjacent to the acetabular shell, a portion of the face segment directly contacts the outer surface of the acetabular shell.

In a further form of the invention, a variable angle blade augment is provided which includes an augment section and a blade segment. The augment section is structured to abut against at least an outer surface of a component of an implantable medical device, and with a reservoir of the augment section structured to receive injection of an adhesive that is configured to unitize at least the augment section with the component of the implantable medical device. The blade segment includes a body segment and an extension, with the extension having a first connector adapted for pivotal displacement about an aperture of the augment section, and with at least a portion of the first connector structured to be secured to the augment section by a mechanical connection, and wherein at least a portion of the blade segment has a length sized to extend through the augment section and directly contact the component of the implantable medical device.

BRIEF DESCRIPTION OF THE DRAWINGS

The description herein makes reference to the accompanying figures wherein like reference numerals refer to like parts throughout the several figures and views.

FIG. 9E illustrates a front view of the augment shown in FIG. 9A.

FIG. 9F illustrates a side view of the augment shown in FIG. 9A.

FIG. 9G illustrates a bottom perspective view of a portion of a neck portion of the blade component shown in FIG. 9A.

FIG. 11A illustrates an exploded back view of a variable angle blade augment having a slotted-type augment component and a separate blade component.

FIG. 11B illustrates a top view of the slotted-type augment component shown in FIG. 11A.

FIG. 11C illustrates a bottom view of the slotted-type of augment component shown in FIG. 11A.

Figure 1:
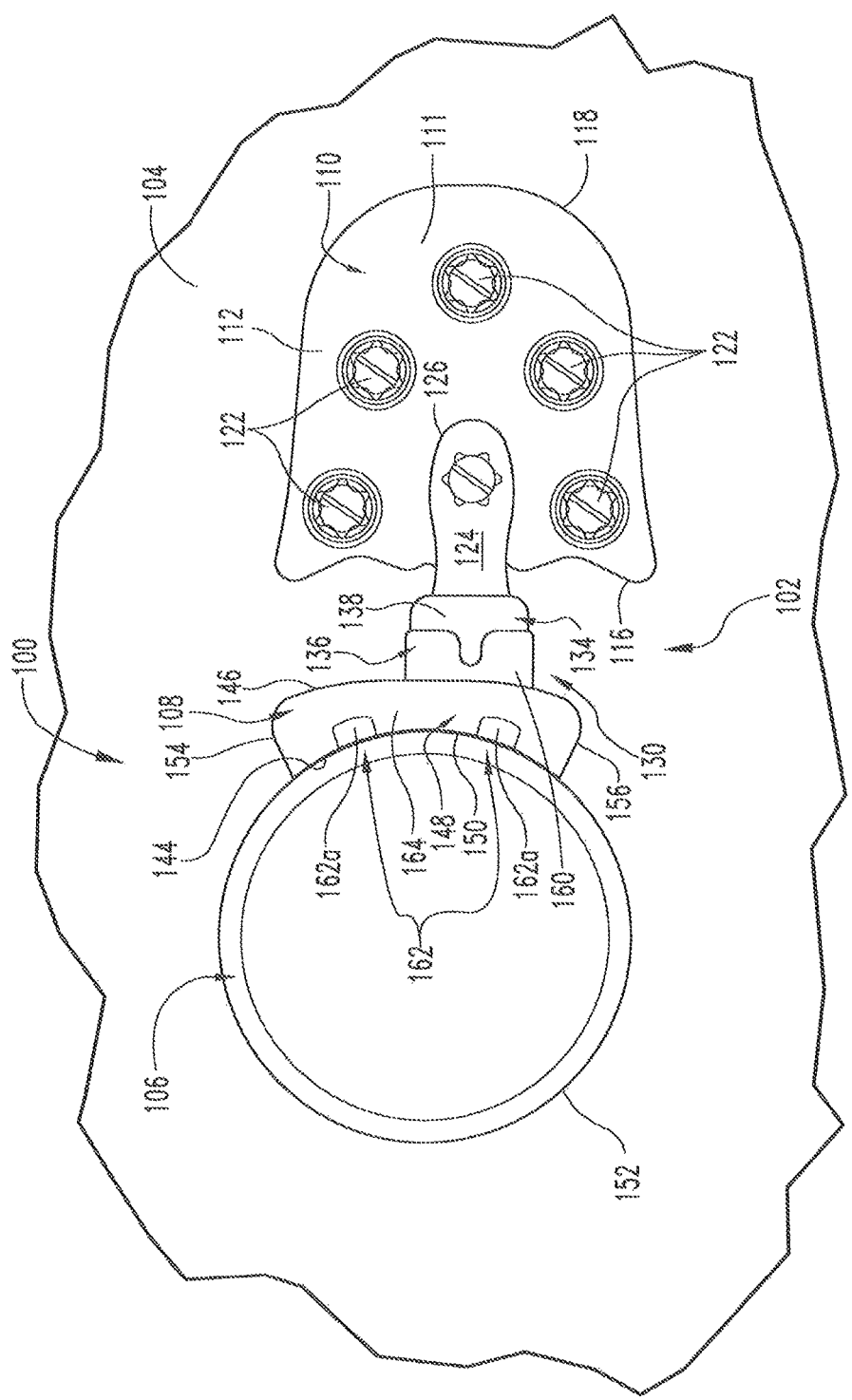
FIG. 1 illustrates a back view of an exemplary implantable medical device having a variable angle blade augment that is operably secured to a bone structure of a patient according to one embodiment.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings. Additionally, the description herein makes reference to the accompanying figures wherein like reference numerals refer to like parts throughout the several views.

DESCRIPTION OF THE ILLUSTRATED EMBODIMENTS

FIG. 1 illustrates a back view of an exemplary embodiment of an implantable medical device 100 having a variable angle blade augment 102 that is operably secured to a bone structure or bone element 104 of a patient according to one form of the present invention. The exemplary implantable medical device 100 generally includes an acetabular cup or shell 106 that is supported, at least in part, by the variable angle blade augment 102. In the illustrated embodiment, the variable angle blade augment 102 includes an augment component 108 and a separate blade component 110.

Figure 2:
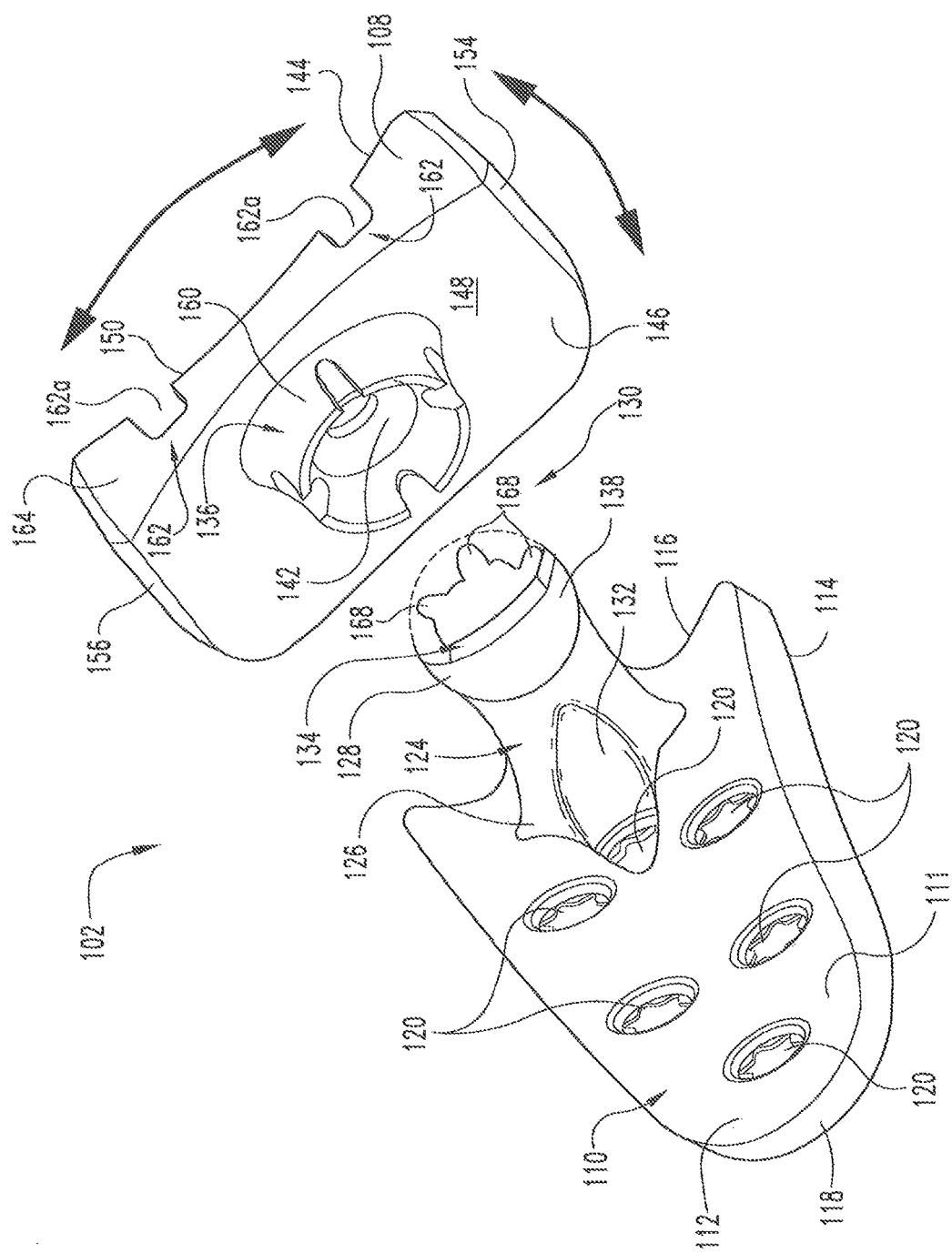
FIG. 2 illustrates an exploded side perspective view of an augment component and a separate blade component of the variable angle blade augment shown in FIG. 1.

FIG. 2 illustrates an exploded side perspective view of the variable angle blade augment 102 shown in FIG. 1, and more particularly shows a perspective view of the augment component 108 and the blade component 110. As shown, the blade component 110 may include a body segment 111 having a first side 112 and an opposite second side 114, as well as opposite first and second end portions 116, 118. As discussed below, the first end portion 116 may be adapted to provide a cement buttress that is used to secure the variable angle blade augment 102 to the acetabular cup 106 and/or the bone structure 104. Additionally, in other embodiments, the shape or contouring of the second side 114 of the body segment 111, which may be implanted adjacent to the bone structure 104 of the patient, may be manufactured or otherwise formed or contoured to match the anatomy of the patient based on pre-operative imaging or manipulation. In still other embodiments, the first side 112 of the body segment 111 may be polished so as to prevent or minimize the first side 112 from irritating or traumatizing adjacent soft tissue. Additionally, the variable angle blade augment 102 can be constructed from a variety of different materials, or combination of materials. For example, according to some embodiments, at least a portion of the variable angle blade augment 102 such as, for example, the second side 114 of the body segment, may be constructed of a porous material that can at least assist in facilitating bone in-growth into the porous material.

The body segment 111 may further include a plurality of orifices or openings 120 (FIG. 2) that generally extend through the body segment 111. The orifices 120 may each be sized and shaped to operably receive one or more mechanical fasteners 122 (FIG. 1) such as, for example, a screw, bolt, pin, and other types of suitable fasteners or anchors, that are used to secure the blade component 110 to the bone structure 104 of the patient.

The blade component 110 may also include an extension 124 that extends generally from the first end portion 116 of the blade component 110. The extension 124 may have a proximal end 126 and a distal end 128, with the proximal end 126 coupled to the body segment 111. Further, in some embodiments, the proximal end 126 may be configured to include a recess or contoured region 132 adapted to accommodate placement of at least one of the orifices 120a and/or to prevent the extension 124 from interfering with insertion and/or engagement of a fastener 122 in the orifice 120a. As discussed in further detail below, the proximal end 126 and/or the distal end 128 of the extension 124 may be adapted to allow the blade component 110 to at least pivotally, angularly and/or rotationally engage the augment component 108 via a modified socket joint 130 in a manner that also permits linear displacement of the blade component 110 relative to the augment component 108.

According to some embodiments, the distal end 128 of the extension 124 may be adapted to provide a first connector 134 for the modified socket joint 130, while the augment component 108 may be adapted to provide a mating socket capture mechanism 136. Conversely, according to other embodiments, the distal end 128 of the extension 124 may be adapted to provide the socket capture mechanism 136, and the augment component 108 may be adapted to provide the first connector 134. Further, according to some embodiments, the first connector 136 may be generally defined by a connector sidewall 138. Additionally, the connector sidewall 138 may have a variety of shapes and configurations. For example, according to some embodiments, the connector sidewall 138 may have a generally spherical-shaped configuration. However, in other embodiments, the connector sidewall 138 may provide the first connector 136 with other shapes or a combination of shapes. Additionally, the connector sidewall 138 may include one or more alignment surfaces 140a, 140b (FIG. 5) that have a shape different than the shape of other portions of the connector sidewall 138.

Figure 5:
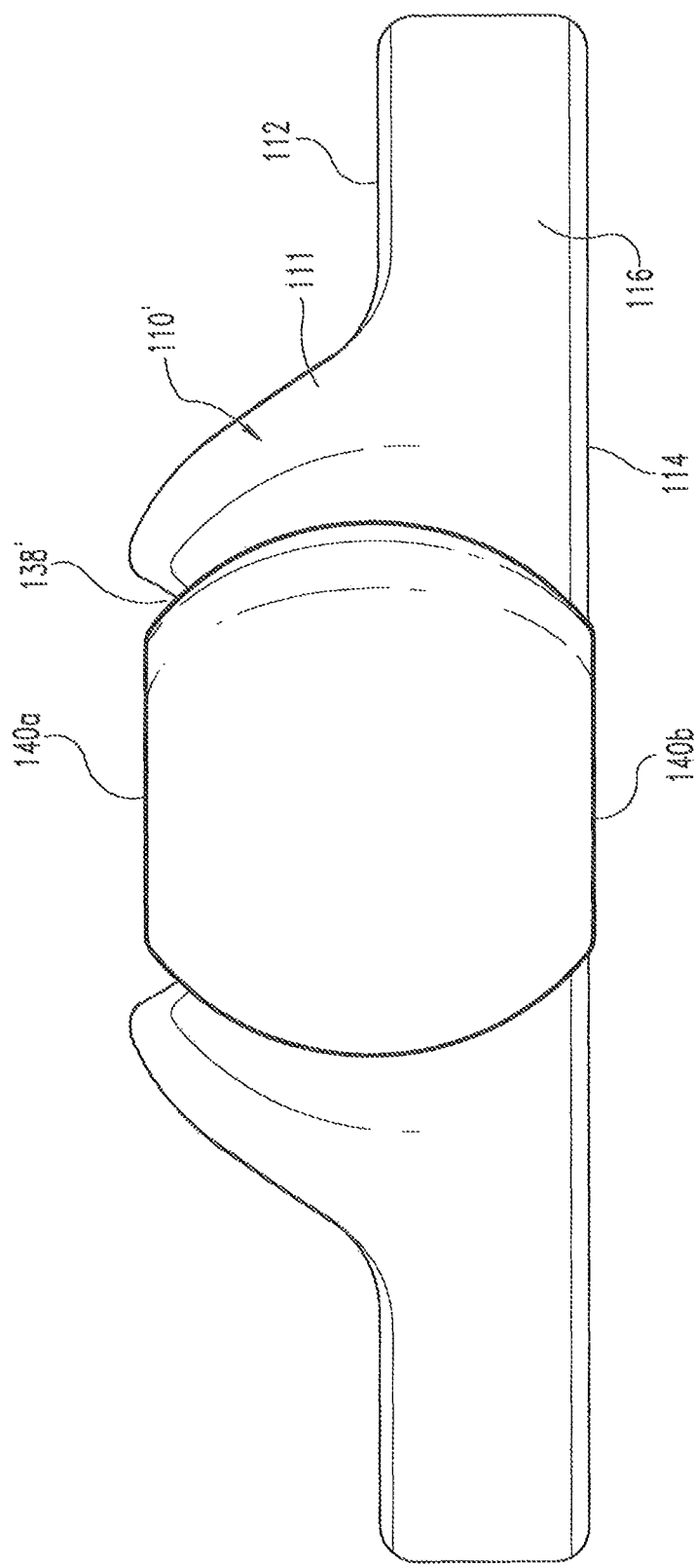
FIG. 5 illustrates a bottom view of the blade component of the variable angle blade augment shown in FIG. 3.

For example, in the illustrated embodiment shown in FIG. 5, while portions of the connector sidewall 138' may be generally spherical in shape, the alignment surfaces 140a, 140b may alternatively be generally flat or planar. More specifically, as shown in FIG. 5, according to some embodiments, the alignment surfaces 140a, 140b may be generally flat surfaces that are positioned on opposite sides of the connector sidewall 138', while portions of the connector sidewall 138' extending between the alignment surfaces 140a, 140b may be at least partially spherical in shape. According to other embodiments, the alignment surfaces 140a, 140b may be used in conjunction with a mating configuration of an aperture 142' of the socket capture mechanism 136' to at least indicate the general orientation of the blade component 110, 110' and augment component 108, 108' such as, for example, the orientation of the augment component 108, 108' relative to the first and second sides 112, 114 of the blade component 110, 110'. Moreover, such alignment surfaces 140a, 140b, as well as a mating configuration in the aperture 142 of the socket capture mechanism 136, if any, may at least assist in providing a keyway type feature that allows for intraoperative assembly of various sized or configured blade components 110 with various other augment components 108, 108', thereby further facilitating the modularity of the variable angle blade augment 102, 102'.

Figure 6:
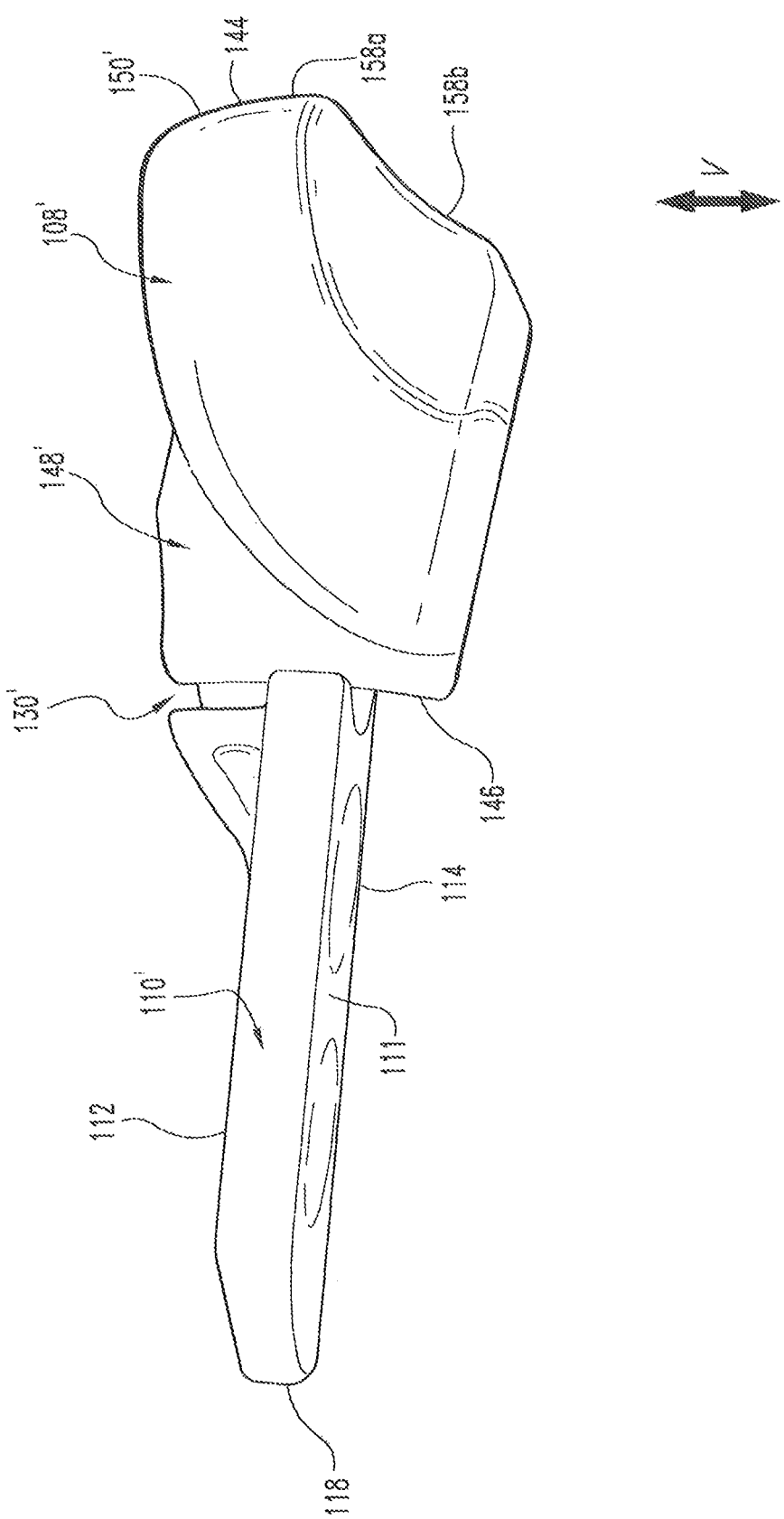
FIG. 6 illustrates a side perspective view of the implantable medical device shown in FIG. 3, with a first connector of the blade component captured in a first end portion of an aperture of a socket capture mechanism of the augment component.

As shown in at least FIGS. 1 and 2, the augment component 108, 108' may include front and rear portions 144, 146 that are positioned on opposite sides of a body region 148 of the augment component 108, 108'. The front portion 144 may include a contoured abutment surface 150 that is shaped for abutment of at least a portion of the abutment surface 150 against at least an outer surface 152 of the acetabular cup 106. The abutment surface 150 may have a variety of different configurations including, for example, having one or more different shapes, sizes and/or segments. For example, as shown in FIGS. 1 and 2, the abutment surface 150 includes a generally curve-shaped or arcuate surface that generally extends from a first side wall 154 to a second side wall 156 of the body region 148. According to such an embodiment, the curved shape of the abutment surface 150 may generally mimic the shape of at least a portion of the outer surface 152 of the acetabular cup 106. Further, according to other embodiments, the abutment surface 150 may have a variety of different sections of the shapes and/or contours. Additionally, according to further embodiments, the abutment surface 150 may be positioned about only certain portions or segments 158a, 158b of the front portion 144 (FIG. 6). Additionally, according to still other embodiments, the abutment surface 150 may protrude or otherwise extend away from the front portion 144 and/or the body region 148.

In addition to use with modular augments, in some embodiments, the variable angle blade augment 102 may also be used with augments that have variable configurations. For example, referencing FIG. 8, in some embodiments, the variable angle blade augment 102 may be utilized with augments 108" that are designed for use on the right side of a patient (i.e., a right hand configuration), or with augments 108" that are designed for use on the left side of the patient (i.e., a left hand configuration). The manner in which the augment 108" is adapted for use on different sides of a patient may vary. According to some embodiments, the extent to which the first and second sidewalls 154, 156 extend from a location on the augment 108" for an augment 108" used in association with a right side of a patient may differ from that of augments 108" used in association with the left side of a patient. For example, according to some embodiments, the first sidewall 154 may be outwardly positioned or offset a distance away from the aperture 142" when the augment component 108" is designed for use in association with the right side of the patient's hip, and which is greater than the distance at which the first sidewall 154 is positioned away from the aperture 142" when the augment component 108" is designed for use in association with the left side of the patient's hip. Conversely, according to some embodiments, the second sidewall 156 may be outwardly positioned or offset a distance away from the aperture 142" when the augment component 108" is designed for use in association with the right side of the patient's hip, and which is less than the distance at which the second sidewall 156 is positioned away from the aperture 142" when the augment component 108" is designed for use in association with the left side of the patient's hip.

Figure 7:
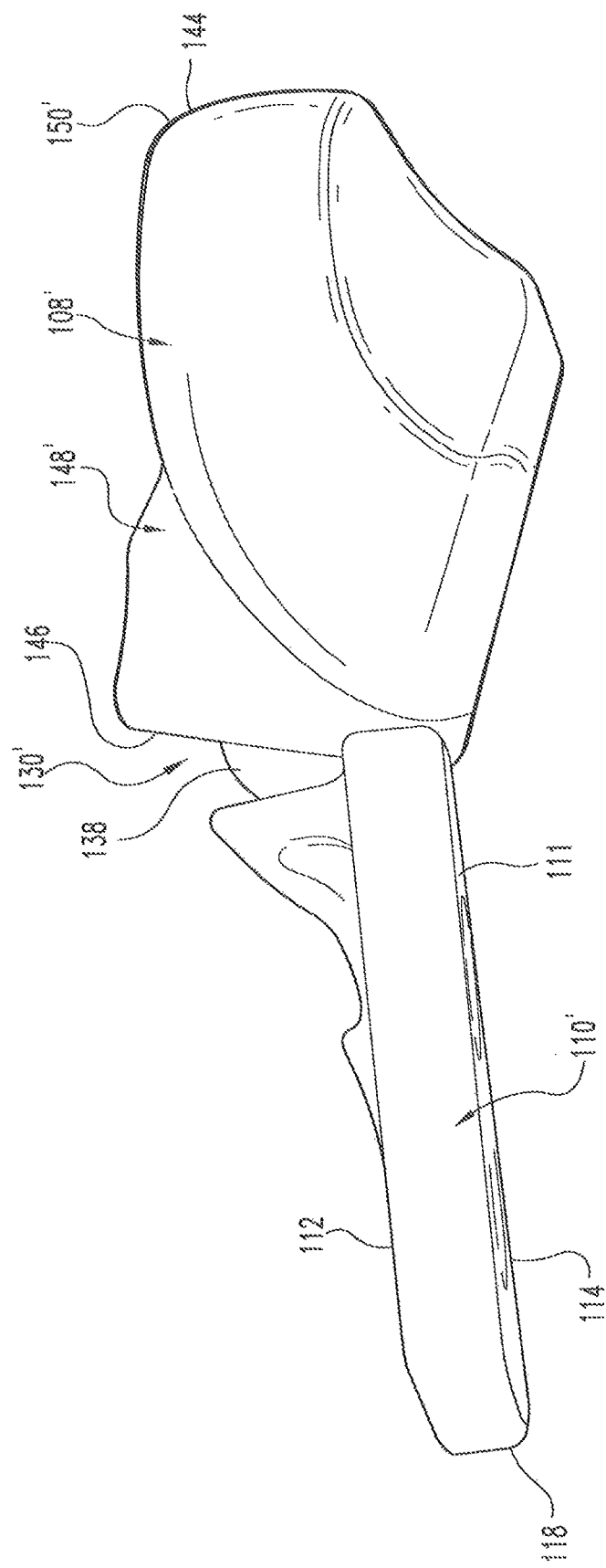
FIG. 7 illustrates a side perspective view of the implantable medical device shown in FIG. 3 with a ball of the blade component captured in a second end portion of an aperture of a socket capture mechanism of the augment component.

As shown in FIGS. 6 and 7, according to some embodiments, the shape or profile of the abutment surface 150' of the augment component 108' may change at least along a generally vertical direction (as indicated by the "V" direction in FIG. 6). Such variations in the shape of the abutment surface 150' may provide the abutment surface 150' with one or more abutment portions 158a, 158b having different configurations that are shaped to accommodate the different angles, positions and/or orientations at which the abutment surface 150' may engage, and eventually be operably secured to, the outer surface 152 of the acetabular cup 106 via manipulation of the modified socket joint 130 during implantation of the medical device 100. For example, the abutment surface 150' shown in FIGS. 6 and 7 includes at least an upper abutment portion 158a and a differently shaped lower abutment portion 158b. Moreover, in the exemplary embodiment shown in FIGS. 6 and 7, the upper abutment portion 158a may have a generally convex shape or contour, while the lower abutment portion 158b may have a generally concave shape or contour.

Referring once again to FIGS. 1 and 2, in some embodiments the socket capture mechanism 136 may be positioned about or in proximity to the rear portion 146 of the augment component 108. For example, the socket capture mechanism 136 may include a socket wall 160 that generally extends along, away from and/or into the rear portion 146 of the augment component 108. Further, the socket wall 160 may generally define the aperture 142 that is configured to at least receive the operable placement of at least a portion of the at least semi-spherical shaped first connector 134 of the blade component 110 of the variable angle blade augment 102.

Figure 3:
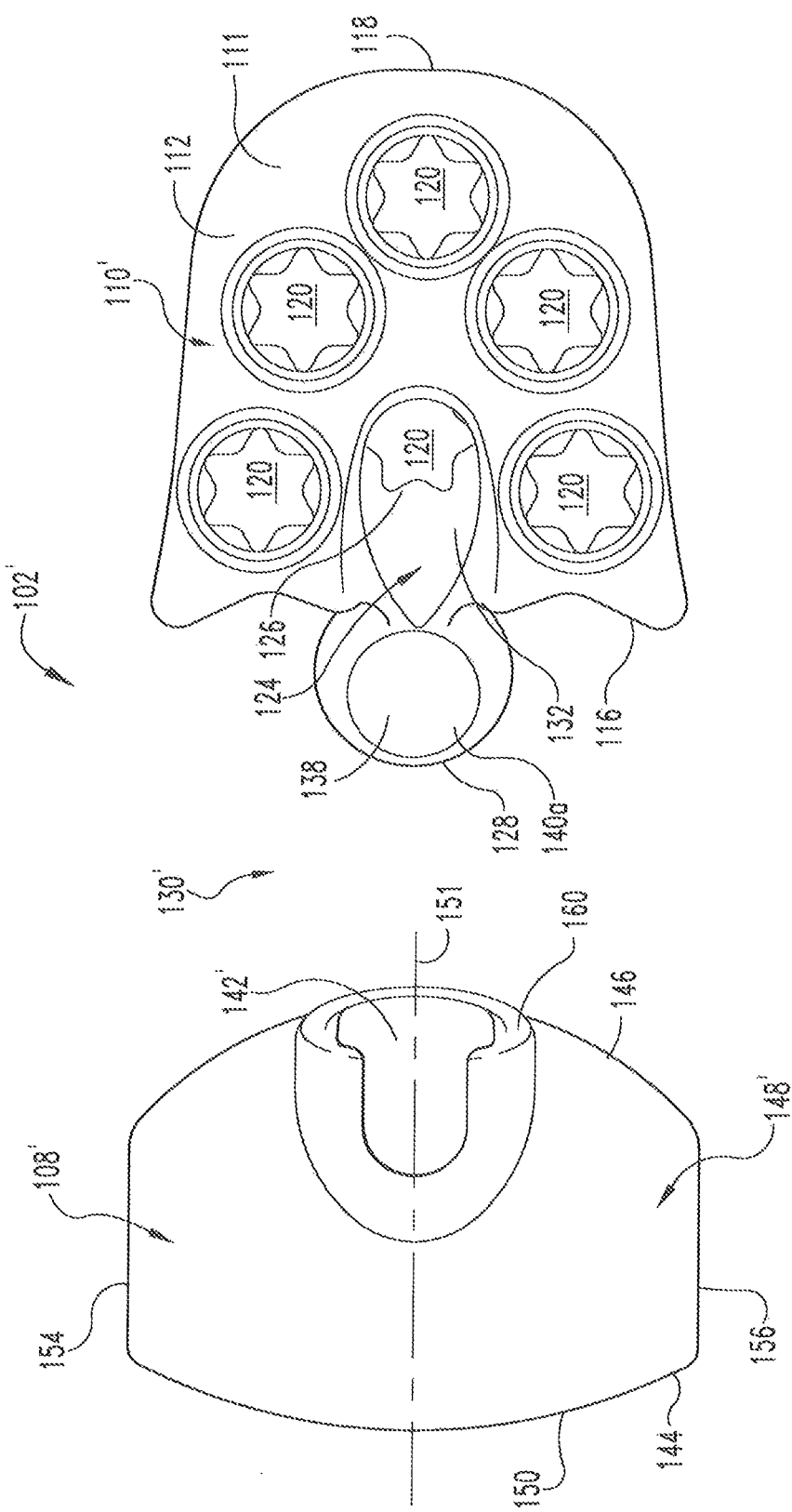
FIG. 3 illustrates an exploded back perspective view of a variable angle blade augment according to one embodiment.
Figure 4:
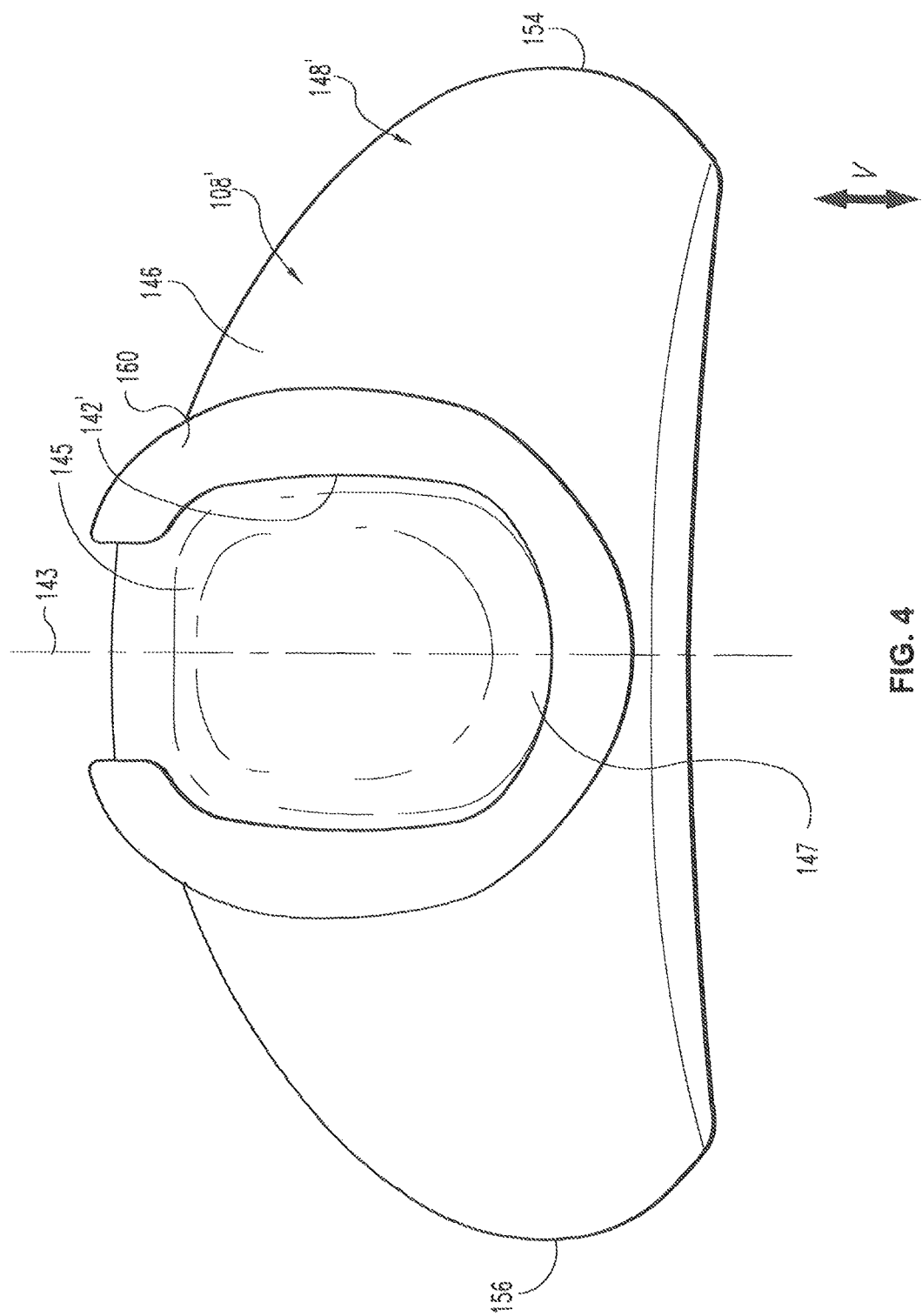
FIG. 4 illustrates a top view of the augment component of the variable angle blade augment shown in FIG. 3.

Referring to FIG. 4, according to some embodiments, the aperture 142' may be generally elongated along at least one axis. For example, as shown in FIGS. 3 and 4, the aperture 142' may be elongated along an aperture axis 143 that is arranged generally perpendicular to a central longitudinal axis 151 of a body region 148 of the augment component 108'. However, the aperture axis 143 may be positioned at a variety of other locations relative to the central longitudinal axis 151 of the augment component. Such an elongated configuration of the aperture 142' may allow for an additional range or degree of movement beyond that which may otherwise be attainable via use of a conventional ball and socket joint. For example, in addition to the relative orientation of the blade component, the augment component 108' may be pivotally adjustable via the socket joint 130', and more specifically the relative movement of the first connector 134' and/or the socket capture mechanism.

As shown in FIGS. 4 and 6, the first connector 134' may be displaced vertically (as indicated by the "V" direction) along the aperture axis 143 to a first position at a first end portion 144 of the aperture 142. Conversely, as shown in FIG. 7, the first connector 134' may also be linearly displaced along the aperture axis 143 to a second position at a second end portion 147 of the aperture 142', with the second end portion 147 being located at an end of aperture 142 that is opposite the end of the aperture 142' at which the first end portion 145 is located. Although the above examples describe the first connector 134' being positioned at opposite ends of the aperture 142', according to other embodiments, the first connector 134' may be positioned at locations between the first and second end portions 145, 147. Further, as previously discussed, in addition to being displaced along the aperture axis 143, the first connector 134' and/or the socket capture mechanism 136' may also be utilized as a ball and socket joint, thereby providing additional ranges of motion, and further facilitating the ability of the variable angle blade augment 102, 102' to accommodate a wide range of various patients' anatomies. Accordingly, the socket joint 130, 130' allows the blade component 110, 110' to be positioned relative to the augment component 108, 108' at a greater variety of positions relative to a typically ball and socket joint arrangement, while still retaining the benefits and advantages of a ball and socket joint.

According to some embodiments, the socket joint 130, 130' may have a generally uniform configuration so as to allow the variable angle blade augment 102, 102' to provide at least a degree of modularity. For example, according to some embodiments, the blade component 110 may be offered in a variety of different sizes and/or configurations including, for example, the option of selecting from blade components 110 that have different sized or shaped body segments 111 and/or extensions 124 that extend from the body segment 111 at a variety of different distances and/or angles. Similarly, the augment component 108, 108' may also be offered in a variety of sizes, shapes, or configuration including, for example, augment components 108, 108' that have different sized or shaped front portions 144 and/or body regions 148, as well as augment components 108, 108' in which the socket capture mechanism 136 is located at different positions relative to the body segment 111, among other variations. According to such embodiments, one or more of the different blade components 110 may include either a first connector 134, 134' or socket capture mechanism 136, 136' that is adapted to operably engage the other of the first connector 134, 134' or socket capture mechanism 136, 136' of a plurality of different sized or configured augment components 108, 108' so as to provide modularity that allows for the use of a variety of different sized or configured blade components 110 and augment components 108, 108'. Such modularity may further enhance the ability to adapt the variable angle blade augment 102, 102' to a patient's anatomy of bone structure. Additionally, according to other embodiments, the blade component 110 and the augment component 108, 108' may be rapid manufactured together, thereby allowing the entire construct to be fabricated at the same time, which in turn may eliminate the need to join the blade component 110 and the augment component 108, 108' together during manufacturing or surgery.

The blade component 110 and/or augment component 108, 108' may include one or more cement ports 162 that are configured to facilitate the injection or placement of an adhesive (i.e., uncured bone cement) into at least the aperture 142, 142' of the socket capture mechanism 136. For example, according to one embodiment, the socket wall 160, 160' may include or more cement ports 162 that are in fluid communication with the aperture 142, 142' of the socket capture mechanism 136, 136'. Additionally, according to other embodiments, one or more of the cement ports 162 may be sized to receive at least a portion of an instrument or device that is used to inject the adhesive into the socket capture mechanism 136, 136' and/or about at least a portion of the first connector 136. Moreover, the one or more cement ports 162 may be configured to facilitate the flow of the adhesive between at least the connector sidewall 138 and the adjacent surfaces of the aperture 142, 142' of the socket capture mechanism 136, 136'. According to other embodiments, the first connector 134 may be configured to provide one or more troughs or pockets 168 that may further facilitate the flow of adhesive between the socket capture mechanism 136 and the first connector 134. Such adhesive (which may include, for example, relatively low viscosity bone cement or other types of adhesives) may, when cured, be used to at least assist in unitizing the blade component 110, 110' and the augment component 108, 108' at a desired orientation.

Additionally, according to some embodiments, the augment component 108, 108' may also include a reservoir positioned adjacent to and in fluid communication with at least the aperture 142 of the socket capture mechanism 136. For example, according to the embodiments illustrated in FIG. 8, one or more cement ports 160*a* may be positioned about an edge 164 of the body region 146 of the augment component 108, 108', 108" that provides at least a passageway for the adhesive to be delivered to the reservoir 166. Further, according to some embodiments, the cement ports 160*a* may be configured as directional ports that direct the flow of adhesive to the reservoir 166. Adhesive supplied to the reservoir 166 may, when cured, at least assist in securing the augment component 108, 108', 108", and in turn the variable angle blade augment 102, 102', to the acetabular cup. Additionally, according to other embodiments, in addition to, or in lieu of, use of an adhesive, the augment component 108, 108', 108" and the variable angle blade augment 102, 102' may be unitized together, or to be secured to the acetabular cup via a mechanical fastener, such as, for example, a mechanically tightened ball and socket joint. Further, such mechanical unitization can be, according to some embodiments, attained through the use of a bone screw, among other mechanical fasteners.

According to further embodiments, during at least some uses or applications, the optimal position of the blade component 110 and the augment component 108, 108' may be determined by adjusting both a linear position of the first connector 134 relative to the aperture axis 143 of the aperture 142, as well as adjusting the angular and/or pivotal orientation of the blade component 110 and the augment component 108, 108' via adjustment of the ball and socket connection provided by the socket joint 130. With the abutment surface 150 at the selected or optimal position or orientation against the acetabular cup 106, the blade component 110, 110' may be secured to the bone structure 104 via insertion of the fasteners 122 in the orifices 120, and associated engagement of the fasteners 122 with the bone structure 104. The adhesive may then be injected into at least the aperture 142 via the one or more cement ports 162 such that adhesive is positioned between the first connector 134, 134' and the socket capture mechanism 136, 136' in a manner that, when the adhesive cures, assists in unitizing the blade component 110, 110' with the augment component 108, 108'. Additionally, adhesive may also be injected via one or more cement ports 162*a* into the reservoir 166 so as to facilitate, when the adhesive cures, the unitization of the variable angle blade augment 102, 102' with the acetabular cup 106. Further, uncured adhesive may also be applied to the areas between the first end portion 116 of the blade component 110 and the augment component 108, 108' and/or the acetabular cup 106 to further unitize the blade component 110 with the augment component 108, 108' and/or the variable angle blade augment 102, 102' with the acetabular cup 106. According to some embodiments, the augment component 108, 108' may also include a cement buttress section that extends adjacent and above the capture socket mechanism 136, 136' and which may also be used with the adhesive to assist in unitizing the blade component 110, 110' with the augment component 108, 108' and/or the variable angle blade augment 102, 102' with the acetabular cup 106. For example, according to certain embodiments, a cement buttress section at the first end portion 116 of the blade component 110, 110' extends adjacent and above the capture socket mechanism 136, 136', and a buttress augment component 108, 108' at the front portion 144 of the augment component 108, 108' that extends adjacent and above the capture socket mechanism 136, 136' may support adhesive, such as, for example, cement, during anatomical loading of the implantable medical device 100.

Figure 8:
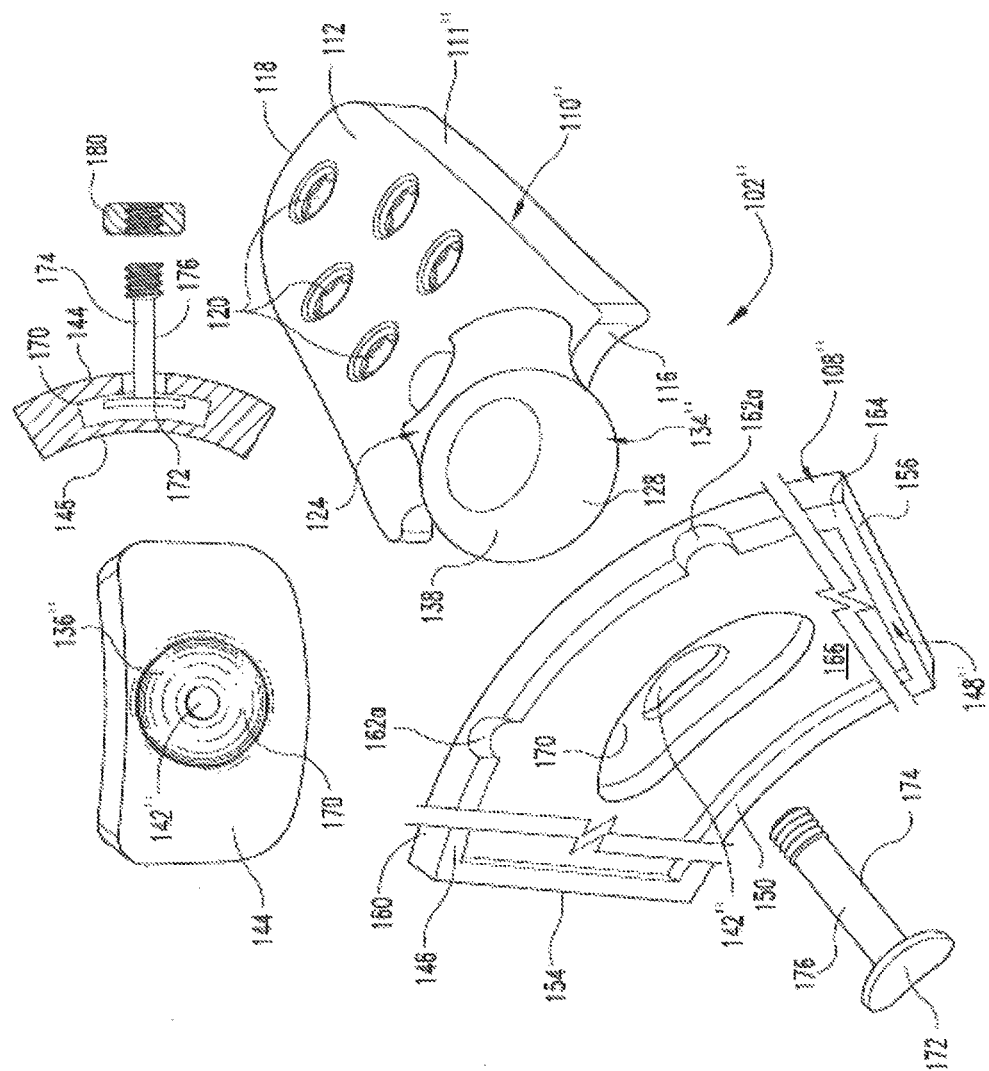
FIG. 8 illustrates an exploded perspective view of an augment component and a separate blade component according to another embodiment of a blade augment.

FIG. 8 illustrates an exploded perspective view of an augment component 108" and a separate blade component 110" according to one embodiment of a blade augment 102". In the embodiment shown in FIG. 8, a mechanical connection such as, for example, a threaded collar or nut/bolt connection or a tapered connection, may be utilized in conjunction with or in addition to an adhesive to secure the first connector 134" to the socket capture mechanism 136". Alternatively, according to another embodiment, a mechanical fastener or adhesive need not be directly used to connect the first connector 110" to the augment component 108", thereby providing a non-captured socket joint 130. In other embodiments, the reservoir 166 may include a recess 170 that is adapted to securely receive a portion of a mechanical fastener 174 such as, for example, the head 172 of a lag bolt or bone screw. Moreover, the recess 170 may be sized to allow at least a body portion 176 of the fastener 174, including a threaded portion, to pass through the recess 170 and the aperture 142" while preventing passage of the head 172. The recess 170 may have variety of shapes including, for example, a generally spherical shape.

Additionally, as shown in FIG. 8, the first connector 134" may include an orifice 178 sized to receive the placement of at least a portion of the body portion 176 of the fastener 174, while also allowing a nut 180 to operably engage the thread of the fastener 174. Such a connection between the fastener 174 and the nut 180 may allow for operable securing or locking of the position and/or orientation of the augment component 108" relative to the blade component 110". According to some embodiments, the first connector 110" may continue to have at least a generally spherical shape, and optionally may be provided with alignment surfaces 140. Moreover, the first connector 110" may be structured for pivotal displacement within an aperture 142" of the augment component 108" prior to be secured in position via a mechanical fastener, such as, for example, via use of a threaded collar that mates with a portion of the first connector 110" or a bolt that extends from or through, or is otherwise operably coupled to, the first connector 110". Additionally, an adhesive may be used to at least assist in unitizing the variable angle blade augment 102" with the acetabular cup 106 including, for example, via the placement of adhesive at least in the reservoir 166 of the augment component 108" and in the gap between the first end 116 of the blade component 110" and the augment component 108" and/or the acetabular cup 106.

FIGS. 9A-9J illustrate an exemplary implantable medical device that includes an acetabular cup or shell 1000 and a variable angle blade augment 1002. As depicted, the variable angle blade augment 1002 includes an augment component 1004 and a blade component 1006. Further, as shown by at least FIG. 9A, and as discussed below, at least a portion of the blade component 1006 is sized to engage, or otherwise interface, the acetabular cup or shell 1000 when the variable angle blade augment 1002 is operably implanted in a patient. Such direct, physical engagement between the blade component 1006 and the acetabular cup or shell 1000 can enhance the structural support and/or stabilization provided by the variable angle blade augment 1002 to the acetabular cup or shell 1000 in recreating the acetabular rim in the host bone.

The augment and blade components 1004, 1006 depicted in FIGS. 9A-9J, as well as other embodiments of components of variable angle blade augments discussed herein, can be constructed from a variety of different materials, including various different types of materials generally used for such orthopedic implants. Further, according to certain embodiments, at least portions and/or surfaces of the augment and blade components 1004, 1006 illustrated in FIGS. 9A-9J, as well as for similar components of other embodiments of augment and blade components disclosed herein, that can contact, or otherwise be facing, the bone of a patient in which the variable blade augment 1002 will be implanted can be constructed of a porous material that can at least assist in facilitating bone in-growth into the porous material, while surfaces of the augment and blade components that can contact or otherwise face soft tissue can be polished surfaces. However, according to certain embodiments, in addition to, or in lieu of, the use of porous materials, bone facing portions of the modular variable blade augment 1002 can employ a variety of other characteristics and/or features to facilitate at least anchorage of the modular variable blade augment 1002 to the host bone. For example, according to certain embodiments, bone facing surfaces of the modular variable blade augment 1002 can include a plurality or spikes or protrusion, among other surface characteristics, that can at least assist in anchoring the modular variable blade augment 1002 to the bone of the patient.

Additionally, according to certain embodiments, the augment component 1004 and/or the blade component 1006 depicted in FIGS. 1A-1J, as well other embodiments of the augment and blade components disclosed herein, can be customized for the anatomy of the patient. Moreover, according to certain embodiments, at least one of, if not both, of the augment and blade components 1004, 1006 depicted in FIGS. 1A-1J can be made to be patient-specific, including, for example, being contoured, shaped, and/or sized or otherwise configured to generally conform to the bone configuration or anatomy of the particular patient. Such embodiments, can include configuring or contouring the augment component 1004 and/or the blade component 1006 based on information regarding the anatomy of the patient, including, but not limited to, images attained of the patient's anatomy from X-rays, among other imaging techniques.

While various embodiments of the blade augments disclosed herein are discussed and illustrated in terms of the augment component and the blade component being separate components, according to other embodiments, the augment component and the blade component can be manufactured in a manner in which the augment component and the blade component are produced in an assembled state. For example, according to certain embodiments, the augment component and the blade component can be produced via additive manufacturing so that the augment component and the blade component are produced in an assembled state rather than as separate components.

Referencing at least FIGS. 9A, 9B and 9G-9J, as illustrated, the blade component 1006 can include a buttress portion 1008 and a neck portion 1010. The buttress portion 1008 can extend along a central axis 1042 (FIG. 9H) of the buttress portion 1008 between a first end 1014 and a second end 1016 of the buttress portion 1008, and include a back side 1018 and an opposing front, or bone facing, side 1020. Further, according to certain embodiments, an outer blade wall 1022 can extend along an outer perimeter of at least a portion of the buttress portion 1008. The height or width of the outer blade wall 1022 can vary to at least accommodate differences in distances between portions of the opposing back and front sides 1018, 1020 of the buttress portion 1008 that are generally adjacent to the outer blade wall 1022, as shown, for example, by at least FIG. 9H.

According to certain embodiments, the buttress portion 1008 can include a plurality of fixation holes 1024 that are configured to receive insertion of one or more mechanical fasteners that can assist in securing at least the blade component 1006 at a selected location, and/or orientation, on the bone of a patient and/or relative to the either or both the acetabular cup or shell 1000 and the augment component 1004. For example, according to certain embodiments, the fixation holes 1024 can be configured to receive and/or engage locking and/or non-locking bone screws, as well as a combination thereof. Further, at least some, if not all, of the fixation holes 1024 can be sized such that when the mechanical fasteners, such as bone screws, are received in the fixation holes 1024 and operably secured to the host bone, the mechanical fasteners are recessed within the fixation holes 1024 such that the mechanical fasteners do not protrude beyond the back side 1018 of the blade component 1006. The fixation holes 1024 can have a variety of different configurations, including for example, but not limited to, the locking holes disclosed in International Application No. PCT/US2016/051864 and U.S. patent application Ser. No. 13/524,506, the disclosures of which are incorporated herein.

Figure 9A:
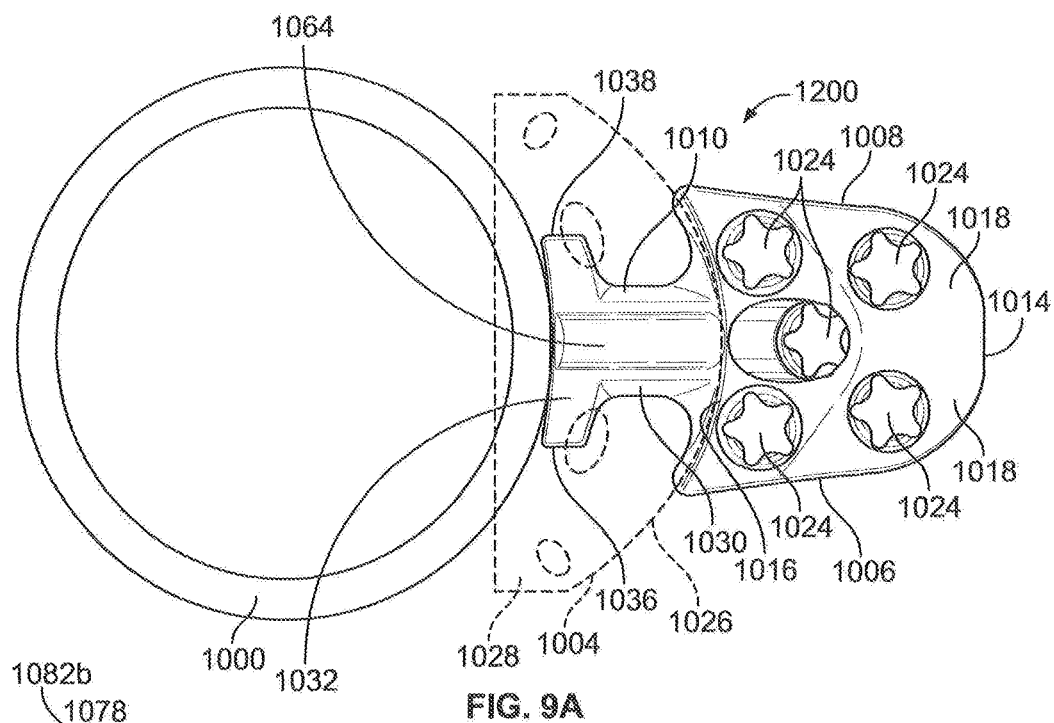
FIG. 9A illustrates a back view of an exemplary implantable medical device having a variable angle blade augment that includes an augment component and a blade component, at least a portion of the blade component sized to engage an acetabular cup or shell.
Figure 9B:
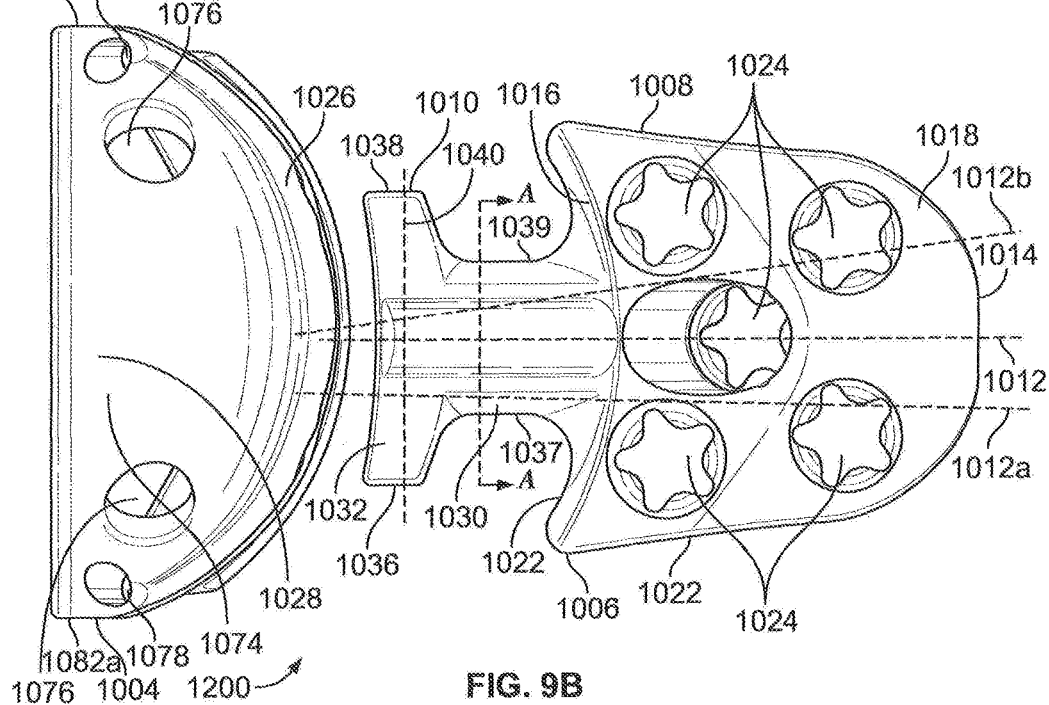
FIG. 9B illustrates an exploded back view of the variable angle blade augment shown in FIG. 9A.

As shown in at least FIGS. 9A and 9B, according to certain embodiments, at least a portion of the outer blade wall 1022 along the second end 1016 of the buttress portion 1008 can have a shape that generally mates, and/or conforms, to the shape of at least a portion of an outer surface 1026 of an augment wall 1028 of the augment component 1004 that the outer blade wall 1022 may engage, or otherwise be at least proximately adjacent to, when the variable angle blade augment 1002 is implanted or otherwise assembled. For example, as shown in at least FIGS. 9A and 9B, at least a portion of the outer blade wall 1022 at the second end 1016 of the buttress portion 1008 can have a generally concave shape that is sized to generally mate with, and/or abut against, a mating convex shaped portion of the outer surface 1026 of the augment wall 1028 of the augment component 1004. Such mating shapes along the second end 1016 of the buttress portion 1008 and the outer surface 1026 of the augment component 1004 may at least increase the size of the surface area, and/or length of the distance, of the portion of the buttress portion 1008 that can be abutted against the augment component 1004, and thereby further enhance the strength and/or stability of the engagement between at least the blade component 1006 and the augment component 1004. Moreover, as the augment component 1004 may abut against at least a portion of the acetabular cup or shell 1000, an enhancement of the strength of the engagement between the blade component 1006 and the augment component 1004 may further enhance the strength and/or stability of the engagement between at least the augment component 1004 and the acetabular cup or shell 1000.

The neck portion 1010 includes a body segment 1030 and a face segment 1032. An end of the body segment 1030 can be connected to, and/or extend from, the second end 1016 of the buttress portion 1008. For example, according to certain embodiments, the body segment 1030 can extend from a portion of the outer blade wall 1022 and/or a portion of the back side 1018 of the buttress portion 1008 that is generally located around the second end 1016 of the buttress portion 1008. Further, for example, as shown in at least FIGS. 9B and 9H, according to certain embodiments, the body segment 1030 can generally extend along a central axis 1034 of the neck portion 1010 that is, in at least a first plane parallel to, and linearly offset from, the central axis 1042 of the buttress portion 1008.

Figure 9C:
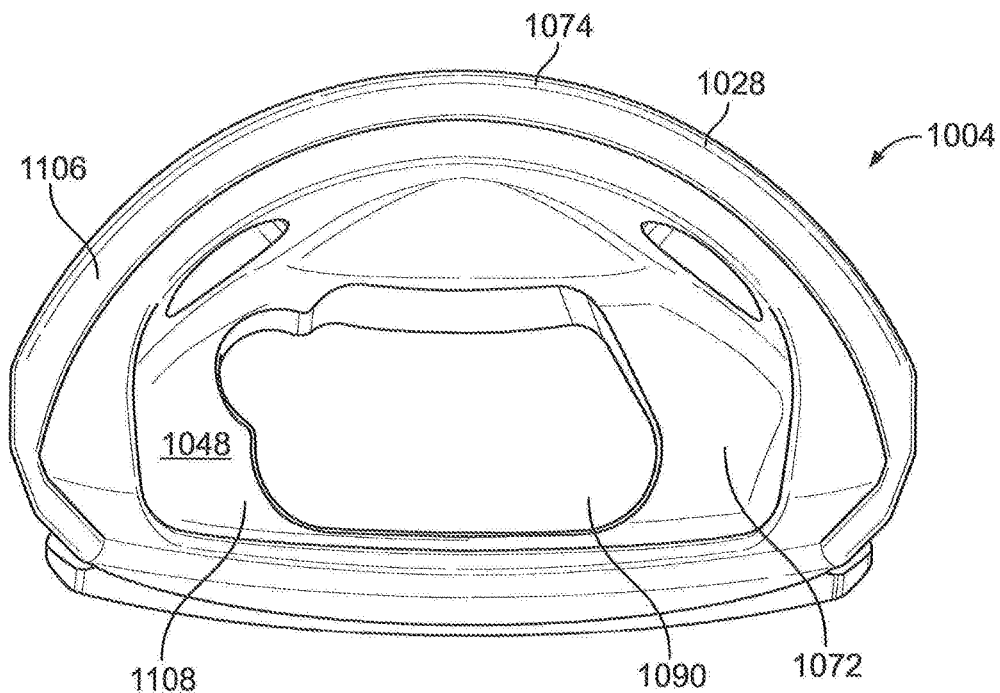
FIG. 9C illustrates a bottom view of the augment shown in FIG. 9A.

Similar to the buttress portion 1008, the body segment 1030 can have a back side 1044 and an opposing front or bone facing side 1046. As shown by at least FIG. 9H, according to the illustrated embodiment, at least a portion of the front side 1046 of the body segment 1030 can be linearly offset from the front side 1020 of the buttress portion 1008 by a distance (as shown by "$D_1$" in FIG. 9H) that can accommodate placement of at least a portion of the augment component 1004 below the front side 1046 of the body segment 1030 at least when the face segment 1032 is positioned in, or through, an internal cavity 1048 (FIG. 9C) of the augment component 1004. Further, as shown in FIG. 9H, given the angled or tapered configuration at the second end 1016 of the buttress portion 1008 from which the body segment 1030 extends, according to certain embodiments, the front side 1046 of the body segment 1030 can extend a linear distance that is shorter than a corresponding linear distance of the back side 1044 of the body segment 1030. Further, as shown by at least FIG. 9A, the body segment 1030 has a length that at least assists in the face segment 1032 being positionable at least when the variable angle blade augment 1002 is implanted at a location at which the face segment 1032 has direct physical contact with the acetabular cup or shell 1000.

The face segment 1032 includes at least a back side 1050, a front side 1052, and a bottom side 1054. Further, in view of at least the difference in length or width between the first and second sidewalls 1036, 1038 of the face segment 1032 in relation to the corresponding width between sidewalls 1037, 1039 of the body segment 1030, the illustrated face segment 1032 can also include a top side 1056. As discussed below in more detail, the front side 1052 of the face segment 1032 can be at least linearly offset from the front side 1020 of the buttress portion 1008 by a distance (as shown by "$D_2$" in FIG. 9H) that is smaller than a distance ("$D_1$") that the front side 1020 of the body segment 1030 is linearly offset from the front side 1020 of the buttress portion 1008. Such differences in offset distances ($D_1$, $D_2$) allows for the formation of a gap 1058 beneath the body segment 1030 and between the face portion 1056 of the face segment 1032 and the second end 1016 of the buttress portion 1008 that can, according to certain embodiments, receive a portion of the augment wall 1028. Moreover, as discussed below, the presence of a portion of the augment wall 1028 in the gap 1058 when the blade component 1006 is assembled with the augment component 1004 can, according to certain embodiments, provide a barrier against linear displacement of the face segment 1032 out of the augment component 1004 in a manner that can at least assist in preventing removal of the face segment 1032 from the internal cavity 1048 of the augment component 1004.

According to certain embodiments, the face segment 1032 can extend between a first sidewall 1036 and a second sidewall 1038 generally along a central axis 1040 that is non-parallel to, and may or may not intersect, the central axis 1034 about which the body segment 1030 extends. For example, referencing FIG. 9B, the central axis 1040 of the face segment 1032 may be generally perpendicular to, although may not intersect, the central axis 1034 about which the body segment 1030 extends. Further, as previously mentioned, the face segment 1032 can have a linear length, or width, between the first and second sidewalls 1036, 1038 of the face segment 1032 that is larger than a corresponding linear length, or width, between similar first and second sidewalls 1037, 1039 of the body segment 1030. According to such a configuration, the neck portion 1010 can have at least a generally "T" shaped appearance in at least one plane (as shown, for example, in FIG. 9B). However, depending on the shape at or around the engagement/transition between the body segment 1030 and the buttress portion 1008, according to certain embodiments, the neck portion 1010 can have a generally "I" beam shaped appearance in at least one plane.

Figure 9D:
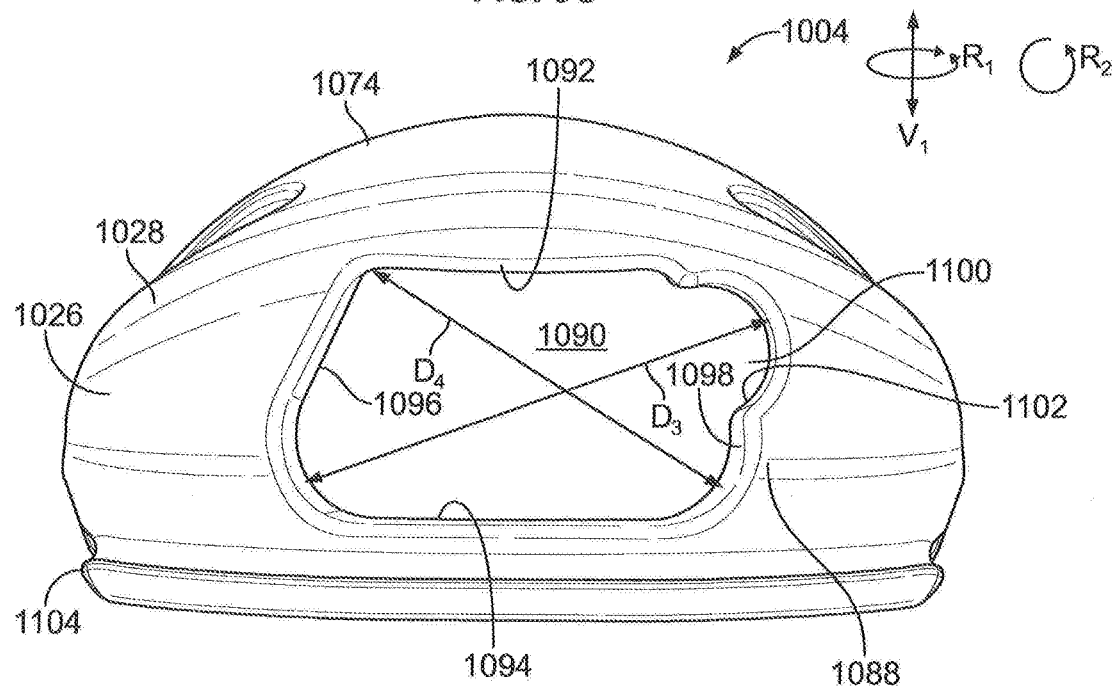
FIG. 9D illustrates a top view of the augment shown in FIG. 9A.
Figure 9H:
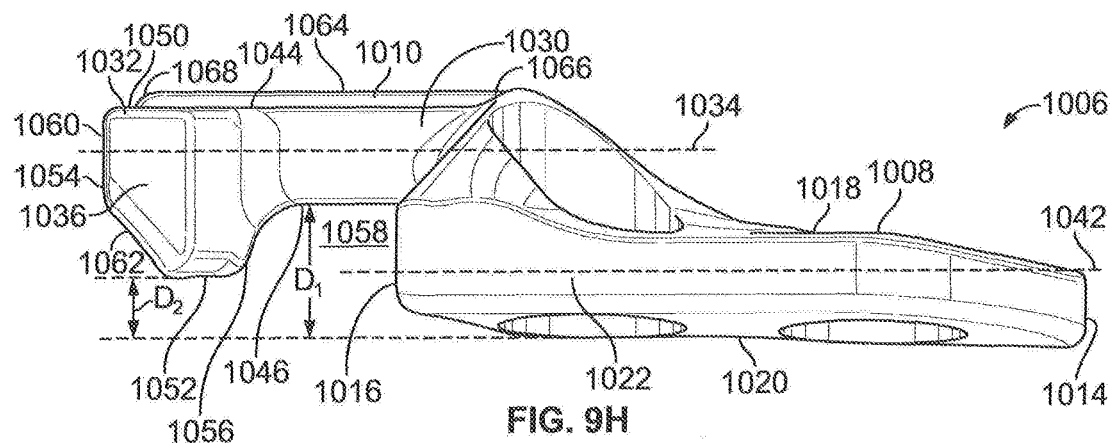
FIG. 9H illustrates a side view of a portion of a neck portion of the blade component shown in FIG. 9A.
Figure 9I:
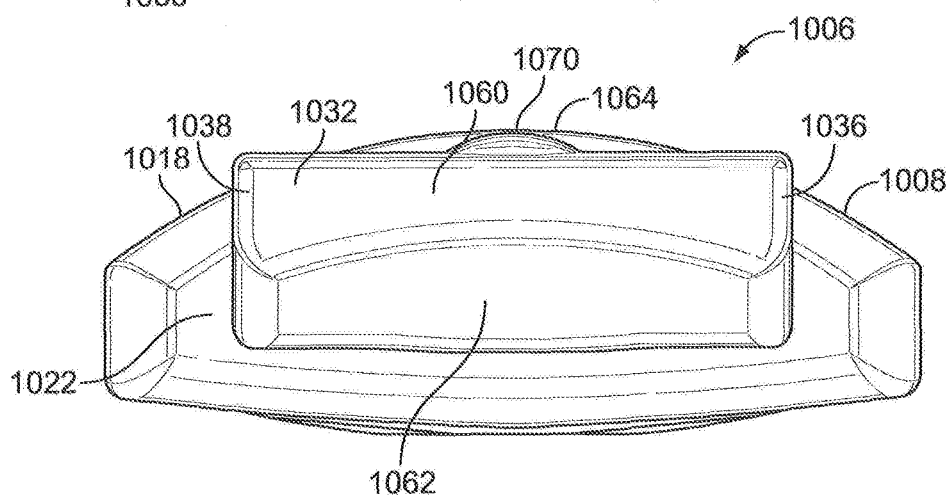
FIG. 9I illustrates a bottom view of a portion of a neck portion of the blade component shown in FIG. 9A.
Figure 9J:
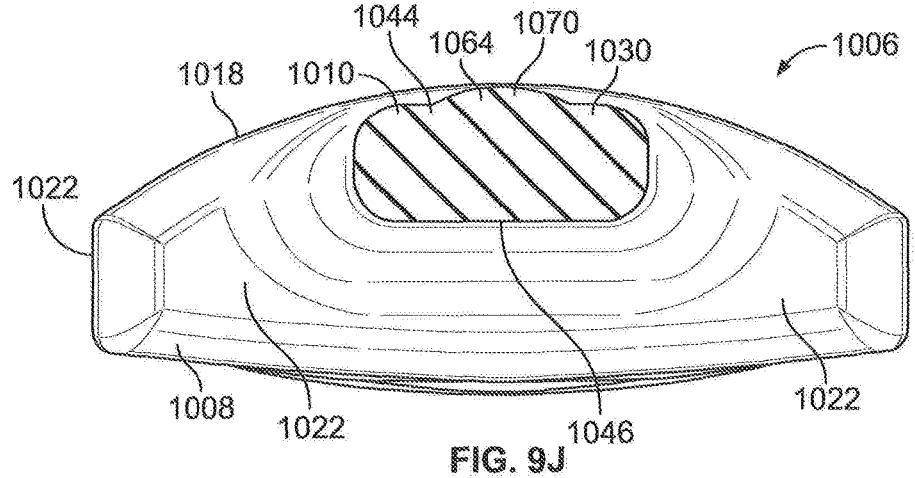
FIG. 9J illustrates a partial cross sectional bottom view taken along line A-A of FIG. 9A.

As shown in at least FIGS. 9G, 9H, and 9I, according to the certain embodiments, at least a portion of the bottom side 1054 of the face segment 1032 is contoured to mate the shape of a corresponding surface of an acetabular cup or shell 1000 against which the face segment 1032 can abut or otherwise contact. For example, according to certain embodiments, the bottom side 1054 of the face segment 1032 includes at least a first face portion 1060 and a second face portion 1062 that generally extend between the first and second side walls 1036, 1038 of the face segment 1032. According to certain embodiments, the first face portion 1060 extends along a different plane than the second face portion 1062, and/or has different shape and/or contours than the second face portion 1062. For example, as shown in at least FIG. 9H, according to certain embodiments, the first face portion 1060 can have at least a side profile that extends in a first plane that is non-parallel, and non-perpendicular, to a the plane about which the second face portion 1062 extends. Further, according to certain embodiments, the first plane in which the first face portion 1060 extend be generally perpendicular to at least the central axis 1034 of at least the body segment 1030 of the neck portion 1010.

According to certain embodiments, only one of the first and second face portions 1060, 1062 may be configured to matingly engage the acetabular cup or shell 1000. For example, as shown by at least FIGS. 9G and 9I, according to certain embodiments, the second face portion 1062 can have a contour, such as, for example, a radius and/or concave curvature, among other shapes and/or contours, along at least a portion, if not approximately all, of the length of the second face portion 1062 between the first and second side walls 1036, 1038 of the face segment 1032. As shown by at least FIG. 9G, the mating shape provided by the second face portion 1062 can, at least according to certain embodiments, be sized to match a mating rounded outer surface or portion of the acetabular cup or shell 1000.

As shown in at least FIGS. 9A, 9B and 9H-9I, according to certain embodiments, a ridge 1064 can extend along at least a portion of the neck portion 1010 of the blade component 1006. For example, according to the illustrated embodiment, the ridge 1064 extends along the back sides 1044, 1050 of at least a portion of both the face segment 1032 and the body segment 1030 of the neck portion 1010. Further, according to the illustrated embodiment, the ridge 1064 can extend from a first end 1066 that is at, or approximately adjacent to, the second end 1016 of the buttress portion 1008, to a second end 1068 that is at, or approximately adjacent to, the first face portion 1060 of the face segment 1032.

The ridge 1064 can have a variety of different shapes, sizes, and configurations. For example, according to the illustrated embodiment, the ridge 1064 is generally semi-cylindrical in configuration such that the ridge 1064 generally rises to an apex 1070 that extends to a height at the back sides 1044, 1050 that is above other portions of the neck portion 1010. Additionally, according to certain embodiments, the apex 1070 of the ridge 1064 may generally extend along at least a portion of the neck portion 1010 that is generally parallel to, and offset from the central axis 1034 about which the body segment 1030 extends. According to certain embodiments, the ridge 1064 can be sized to provide additional support and/or strength to at least the neck portion 1010. For example, according to certain embodiments, the ridge 1064 can be configured, such as, for example, sized and/or positioned, to provide support and/or strengthen the neck portion 1010 with respect to bending moments that the neck portion 1010 may encounter during at least use of the variable angle blade augment 1002.

At least FIGS. 9A-9F also illustrate an example of an augment component 1004 that can be configured to be assembled with the blade component 1006 to provide the variable angle blade augment 1002. According to the illustrated embodiment, the augment component 1004 can comprise an augment wall 1028 having an outer surface 1026 and an inner surface 1072. The inner surface 1072 of the augment wall 1028 can generally define at least a portion of the internal cavity 1048 of the augment component 1004. The outer surface 1026 of the augment wall 1028 can generally define at least an external shape(s) of the augment component 1004 as well as provide a variety of different features for the augment component 1004.

As shown in at least FIGS. 9B and 9F, a back side portion 1074 of the augment wall 1028 can include one or more cement ports 1076 that are in fluid communication with the internal cavity 1048. For example, in the illustrated embodiment, the augment component 1004 includes two cement ports 1076 that are positioned at generally opposite sides of at least the back side portion 1074 of the augment wall 1028, and which provide passageways in the augment wall 1028 through which cement can be injected into, or otherwise delivered to, the internal cavity 1048 of the augment component 1004.

As also shown in at least FIGS. 9B, 9E and 9F, the augment component 1004 can also include a plurality of provisional holes 1078. According to certain embodiments, the provisional holes 1078 can be sized to receive a mechanical fastener, such as, for example, a provisional pin, that can be used to at least temporarily secure the position and/or orientation of the augment component 1004 relative to the bone of the patient and/or other components of the implant. For example, according to certain embodiments, one or more of the provisional holes 1078 can receive a pin that secures the position and/or location of the augment component 1004 at least while cement is inserted into the internal cavity 1048 via the cement port(s) 1076 and/or while cement in the internal cavity 1048 cures. The provisional holes 1078 can be positioned at a variety of locations about the augment component 1004. For example, a first end 1080 of the provisional holes 1078 can be positioned at a sidewall portion 1082a, 1082b of the augment wall 1028 proximally adjacent to the back side portion 1074 of the augment wall 1028, and extend to a second end 1086 of the provisional hole 1078 along a portion of the sidewall portion 182a, 182b of the augment wall 1028 that is at or near a front side portion 1086 of the augment wall 1028. While embodiments discussed herein address the use of provisional holes 1078 with an augment component 1004, similar provisional holes can also be used to at least temporarily secure a position of the blade component 1006. For example, according to certain embodiments, provisional holes can also be positioned at one or more locations along the buttress portion 1008 of the blade component 1006 such that a provisional pin or other fixation device can extend though at least a portion of the provisional hole and into the bone of the patient. For example, according to certain embodiment, one or more provisional holes can be positioned to extend from the back side 1018 through the front side 1020 or the outer blade wall 1022 of the buttress portion 1008, and/or from the outer blade wall 1022 and through the front side 1020 of the buttress portion 1008, among other locations.

As shown in at least FIG. 9D, the augment wall 1028 can include a top side portion 1088. According to certain embodiments, at least a portion of the outer surface 1026 of the top side portion 1088 of the augment wall 1028 can be configured, such as, for example, sized, shaped, and/or oriented, for a mating engagement with, or otherwise for being positioned approximately adjacent to, the second end 1016 of the buttress portion 1008 of the blade component 1006. For example, as previously discussed and shown in at least FIGS. 9A and 9B, the outer surface 1026 of the top side portion 1088 of the augment wall 1028 can have a rounded, curved, or convex shape that is generally similar to a rounded, curved, or concave shape of at least a portion of the second end 1016 of the buttress portion 1008 that can be positioned against, or in positioned approximately adjacent to, the augment wall 1028.

The top side portion 1088 of the augment wall 1028 can include a first opening 1090 that is in communication with the internal cavity 1048. The first opening 1090 can be sized to accommodate insertion of at least the face segment 1032 of the neck portion 1010 of the blade component 1006 through the first opening 1090 and into at least the internal cavity 1048 when the blade component 1006 is at a select position or orientation relative to the augment component 1004. Such select position(s) and/or orientation(s) for insertion of at least the face segment 1032 of the neck portion 1010 through the first opening 1090 can be generally limited to one or more select relative orientations that are generally different than a relative orientation of the augment component 1004 and the blade component 1006 that may typically be attained during subsequent installation/implantation steps and/or use of the implanted variable angle blade augment 1002. Additionally, the first opening 1090 can be sized such that, once at least the face segment 1032 of the neck portion 1010 has passed through the first opening 1090 and is positioned at least in the internal cavity 1048, the face segment 1032 cannot be removed through the first opening 1090 without returning the blade component 1006 to an orientation used to initially insert the face segment 1032 into/through the first opening 1090.

According to the embodiment illustrated in at least FIGS. 9C and 9D, the first opening 1090 in the augment wall 1028 can include an upper wall 1092 and an opposing lower wall 1094. Further, a first sidewall 1096 and a second sidewall 1098 of the first opening 1090 can extend between opposing ends of the upper and lower walls 1092, 1094. At least the first and second sidewalls 1096, 1098 can be configured to increase at least a portion of a size of the first opening 1090 such that, when at least the neck portion 1010 of the blade component 1006 is at least at one select, and not every, angular orientation (as indicated by "$R_1$" in FIG. 9D) relative to the augment component 1004, the face segment 1032 of the neck portion 1010 can pass through the first opening 1090 and into at least the internal cavity 1048. According to certain embodiments, at least one of the first and second sidewalls 1096, 1098 can have a configuration that increases at least one length of the first opening 1090 in only one general area across the first opening 1090.

For example, in the embodiment illustrated in FIG. 9D, the second sidewall 1098 can include a notch 1100 that increases a size of only a portion of the first opening 1090. According to such an embodiment, the inclusion of the notch 1100 can result in an opened area in the first opening 1090 along a first diagonal distance ("$D_3$" in FIG. 9D) that extends between at least the general proximity of two diagonally opposing corners of the first opening 1090. Further, the inclusion of the additional space provided by the inclusion of the notch 1100 in a portion of the first opening 1090 can result in the first diagonal distance ("$D_3$") being is larger than another diagonal distance ("$D_4$" in FIG. 9D) that extends generally between the other two diagonally opposing corners of the first opening 1090. Further, the first diagonal distance ("$D_3$") may be smaller than a linear distance between the opposing first and second sidewalls 1036, 1038 of the face segment 1032 of the neck portion 1010. Accordingly, insertion of the face segment 1032 through the first opening 1090 via use of at least the notch 1100 can be configured to be limited to situations in which the blade component 1006 is manipulated to at least and a certain angular orientation relative to the augment component 1004 such that one of the first and second sidewalls 1036, 1038 of the face segment 1032 can at least initially enter into first opening 1090, if not generally passes through the first opening 1090, before the other of the first and second sidewalls 1036, 1038 can enter the first opening 1090 and/or pass through the first opening 1090. For example, according to certain embodiments, insertion of the face segment 1032 of the neck portion 1010 into, and through the first opening, can be limited to instances when the blade component 1006 has at least been rotated about a first axis (as indicated by "$R_1$" in FIG. 9D) that can be, for example, generally perpendicular to the central axis 1032 of the body segment 1030, and in which the blade component 1006 has been manipulated so that at least a portion of the face segment 1032 passes through the notch 1100.

In addition to differences in sizes between the first opening 1090 of the augment component 1004 and the face segment 1032 of the neck portion 1010 generally limiting the ability to insert, and thus also remove, the face segment 1032 into/through the first opening 1090, as previously discussed, the location of the portion of the first opening providing the increased size, such as, for example, the notch 1100, can also be used to control insertion/removal of the face segment 1032 through the first opening 1090. For example, as shown by at least FIG. 9D, the notch 1100 can be position away from, or above, the lower wall 1094 in a first vertical direction (as indicated by "$V_1$" in FIG. 9D).

Accordingly, according to certain embodiments, insertion of at least the face segment 1032 through the first opening 1090 may involve not only the blade component 1006 being angled relative to the augment component 1004 so that the larger length of the face segment 1032 can pass through the first opening 1090, but also being tilted or rotated about a second axis (as indicated by the "$R_2$" direction in FIG. 9D) that, for example, can be generally parallel to the central axis 1034 of the body segment 1030. According to the illustrated embodiment, for example, the blade component 1006 can be rotated about the second axis such that the one of the first and second sidewalls 1036, 1038 of the face segment 1032 that is to pass through the notch 1100 is generally aligned with the notch 1100. According to such an example, the rotation of the blade component 1006 about the second axis can result in the one of the first and second sidewalls 1036, 1038 of the face segment 1032 that is to pass through the notch 1100 being at a distance away from the lower wall 1094 of the first opening (generally in the "$V_1$" direction) that is larger than a corresponding distance between the lower wall 1094 and the other of the first and second sidewalls 1036, 1038 of the face segment 1032. Additionally, the notch 1100 can be positioned such that when the blade component 1006 is operably assembled with the augment component 1004, including, for example, at least when the variable angle blade augment 1002 is implanted in a patient and/or while the assembled variable angle blade augment 1002 is being positioned for implantation, a lower portion 1102 the notch 1100 is at location in generally in the "$V_1$" direction (FIG. 9D) that is higher than, or offset from front side 1052 of the face segment 1032 so as to further generally prevent or restrict the ability of the face segment 1032 that is positioned in the internal cavity 1048 from reentering into the notch 1100 without the blade component 1006 being re-manipulated to an orientation/position similar that which previously allowed passage of the face segment 1032 through the first opening 1090 and into the internal cavity 1048.

Additionally, according to at least some embodiments, the lower wall 1094 of the first opening 1090 can be generally positioned from the front side portion 1084 of the augment wall 1028 by a distance that further assists in retaining a blade component 1006 that has been received through the first opening 1090 and into the internal cavity 1048 from subsequently being inadvertently removed from the augment component 1004. More specifically, as previously discussed with respect to at least FIG. 9H, the front side 1052 of the face segment 1032 can be at least linearly offset from the front side 1020 of the buttress portion 1008 by a distance ("$D_2$") that is smaller than the distance ("$D_1$") that the front side 1046 of the body segment 1030 is linearly offset from the front side 1020 of the buttress portion 1008. Such a configuration can provide the gap 1058 beneath the body segment 1030, and moreover, between the face segment 1032 and the buttress portion 1008, that can, when the blade component 1006 and the augment component 1004 are assembled, generally receive placement of at least a portion of the lower wall 1094 of the first opening 1090. According to such an embodiment, at least the lower wall 1094 can provide a barrier against inadvertent displacement of at least the face segment 1032 from the internal cavity 1048 through the first opening 1090.

At least the internal cavity 1048 and the first opening 1090 of the augment component 1004 are size relative to the face segment 1032 and body segment 1030, respectively, such that when the face segment 1032 has been received in the internal cavity 1048 and the body segment 1030 extends through the first opening 1090, the variable angle blade augment 1002 can accommodate a relatively wide range of angulation between the blade component 1006 and the augment component 1004. Moreover, such sizing of the augment component 1004 and blade component 1006 can accommodate the blade component 1006 being twisted and/or positioned off-centered relative to the augment component 1004 so that the variable angle blade augment 1002 can have an adjustable configuration that can accommodate the various different anatomies and/or defects of a relatively wide range of patients.

For example, FIG. 9B illustrates the blade component 1006 at a generally centered, neutral position relative to the augment component 1004, as represented by a centerline 1012 of the blade component 1004. For at least purposes of illustration, FIG. 9B also provides an example of an off-centered location, as represented by centerline 1012a of the blade component 1006, that, according to the depicted embodiment, the blade component 1006 can be linearly displaced and positioned relative to the augment component 1004. Such sizing of the features of the augment component 1004 and blade component 1006 can also accommodate a degree of rotational displacement of the blade component 1006 relative to the augment component 1004, as illustrated by a comparison of the angular position of the centerline 1012b of the blade component 1006 shown in FIG. 9B with the position of the centerline 1012 when the blade component 1006 is at the central, neutral position. Such rotational displacement of the relative position of the blade component 1006 can accommodate the positioning, and implantation of the blade component at a location at which the rotated centerline 1012b of the angularly adjusted blade component 1006 is non-parallel to the depicted central, neutral position of the centerline 1012.

While, for purposes of illustration, FIG. 9B provides a single example of the blade component 1006 being offset from a central, neutral location, as well as a single example of the blade component 1006 being angularly adjusted relative to the central, neutral location of the blade component 1006, the augment component 1004 and the blade component 1006 can be configured to accommodate the blade component 1006 being off-centered from, and/or angularly positioned relative to, the central, neutral position by a variety of different distances and/or degrees. Additionally, such sizing of the augment component 1004 and the blade component 1006 can accommodate such linear and/or angular adjustments in the positioning and/or orientation in a variety of different directions relative to the central, neutral location of the blade component 1006. Further, while FIG. 9B illustrates the blade component 1006 being either linearly adjusted or angularly adjusted from the depicted central, neutral location, the sizing of the augment component 1004 and the blade component 1006 can also accommodate the combination of both such linear, off-centered adjustment(s) and angular adjustment of the relative position of the blade component 1006. Further, while FIG. 9B generally illustrates such linear and angular adjustments of the blade component 1006 in a single plane, such as, for example, generally linearly or rotably displacing the blade component 1006 toward one of the first and second sidewalls 1096, 1098 of the first opening 1090, the augment component 1004 and blade component 1006 can be sized to accommodate such linear and/or angular adjustment of the blade component 1006 in other planes, and a combination thereof, such as, for example, but not limited to, generally linearly or rotably displacing the blade component 1006 toward one of the upper and/or lower walls 1092, 1094 of the first opening 1090 in addition to, or in lieu of, adjustments relative to the first and second sidewalls 1096, 1098 of the first opening 1090.

The body segment 1030 of the blade component 1006 can also be sized, such as, for example, have a length, to accommodate linear adjustment in the location of at least the face segment 1032 relative to the augment component 1004 and/or the acetabular cup or shell 1002. Moreover, such body segment 1030 have a length that can accommodate adjusting the linear location of at least the face segment 1032 such that the face segment 1032 can be displaced to a location at which at least a portion of the face segment 1032 can abut the acetabular cup or shell 1000. For example, the body segment 1030 can have a length between the second end 1016 of the buttress portion 1008 and the top side 1056 of the face segment 1032 that can accommodate at least linear adjustments in the positioning of the body segment 1030 relative to at least the first opening 1090 so as to facilitate the face segment 1032 being positioned to contact the acetabular cup or shell 1000.

According to certain embodiments, at least a portion of the bone facing sides of the outer surface 1026 of the augment wall 1028, such as for example, at least a portion of the top side portion 1088 and/or sidewall portions 1082a, 1082b of the outer surface 1026 of the augment wall 1028 can also include a retention ridge or lip 1104. The retention lip 1104 can have a variety of shapes and sizes, and can be generally configured to provide a barrier against, or to minimize, the flow, if any, of cement into the host bone. For example, according to the illustrated embodiment, the retention lip 1104 generally outwardly protrudes away from adjacent portions of the outer surface of the augment wall 1028 so as to provide a barrier that at least attempts to stop the flow, or otherwise catch, cement that may pass along or around at least a portion of the outer surface 1026 of the augment wall 1028. While the retention lip 1104 can be positioned at a variety of locations about the bone facing sides of the augment wall 1028, according to the illustrated embodiment, the retention lip 1104 can be generally located in the "V₁" direction (FIG. 9D) between the lower wall 1094 of the first opening 1090 and the front side portion 1084 of the outer surface 1026 of the augment wall 1028. Moreover, according to certain embodiments, the retention lip 1104 can be proximally adjacent to the front side portion 1084 of the outer surface 1026 of the augment wall 1028, and/or can be an extension of at least a portion of the front side portion 1084 of the outer surface 1026 of the augment wall 1028, as indicated, for example, by FIG. 9E.

The augment wall 1028 also includes a bottom side portion 1106, as shown in at least FIG. 9C, that is configured to abut, or otherwise be positioned proximally adjacent to, the acetabular cup or shell 1000, as shown in FIGS. 9A and 9B. Thus, at least the outer surface 1026 of the augment wall 1028 along at least a portion of the bottom side portion 1106 can have a shape and/or contours that generally mate the shape of at least the portion of the acetabular cup or shell 1000 against which the augment component 1004 can abut. Additionally, the bottom side portion 1106 of the augment wall 1028 can be configured to generally define a second opening 1108 in the augment component 1004. The second opening 1108 is in fluid communication with the internal cavity 1048 and sized to accommodate the face segment 1032 of the blade component 1006 being in direct contact with the acetabular cup or shell 1000. For example, according to certain embodiments, the second opening 1108 can be sized to receive insertion of at least a portion of at one of the acetabular cup or shell 1000 and the face segment 1032 of the blade component 1006. Further, according to certain embodiments, the face segment 1032 of the blade component 1006 can be in direct contact with the acetabular cup or shell 1000 at, or in the general vicinity of, the second opening 1108.

FIG. 9E illustrates an exemplary front side portion 1084 of the augment wall 1028 according to certain embodiments of the present application. As shown, according to certain embodiments, the front side portion 1084 can extend between a region of the bottom side portion 1106 of the augment wall 1028 that has a shape that generally conforms to the shape of the acetabular cup or shell 1000 to a region of the bottom side portion 1106 that is proximally adjacent to, if not part of, the retention ridge or lip 1104. Additionally, according to certain embodiments, at least a portion of the provisional holes 1078 can also extend to, or be in the general vicinity of, the front side portion 1084 of the augment wall 1028.

The internal cavity 1048 of the augment component illustrate in at least FIG. 9A, as well as the augment components of other embodiments discussed below, is sized to receive not only at least a portion of the neck portion 1010 of the blade component 1006, such as, but not limited to, a portion of the face segment 1032, but to also receive an injected fixation material, such as for example, and adhesive material, including, but not limited to, bone cement. As previously mentioned, the blade component 1006 and augment component 1004 can be sized and configured to accommodate the blade component 1006 being in direct contact with the acetabular cup or shell 1000 when the variable angle blade augment 1002 is being implanted. Accordingly, with the variable angle blade augment 1002 positioned such that blade component 1006 is operably inserted into the augment component 1004 at a selected position/orientation, and with the blade component 1006, and moreover the face segment 1032, in contact with the acetabular cup or shell 1000, cement can be injected into the internal cavity 1048 via one or more cement ports 1076. In such a situation, the curing of the cement will at least assist in unitizing the acetabular cup or shell 1000 and the blade component 1006. Further, such curing of the cement can also assist in securing the augment component 1004 to the acetabular cup or shell 1000. Thus, the unitizing of at least the acetabular cup or shell 1000 and the blade component, including blade component 1006, as well as the securing of the augment component 1004, to the acetabular cup or shell 1000 can occur at generally one location within the internal cavity 1048. Such features are also applicable to at least the various other embodiments of augment components and blade components discussed below.

Additionally, according to certain embodiments, at least some portions of the blade component 1006 that can be exposed to the fixation material that is injected into the internal cavity 1048 via one or more cement ports 1076 can be configured to at least assist in facilitating or enhancing the adherence of the fixation material to the blade component 1006. For example, according to certain embodiments, at least a portion of an outer surface(s) of the body segment 1030 and/or face segment 1032 can have surface features or characteristics that can enhance adherence of a fixation material, such as, but not limited to, bone cement, to the body segment 1030 and/or face segment 1032. A variety of such surface features or characteristics can be utilized, including, for example, a plurality of protrusions or bumps that are positioned at various locations along at least a portion of the outer surface of the body segment 1030 and/or face segment 1032, among other surface features or characteristics.

FIGS. 10A-10G illustrate an exemplary variable angle blade augment 1200. As depicted, the variable angle blade augment 1200 includes an augment component 1202 and a blade component 1204. Further, similar to the blade component 1006 depicted in at least FIG. 9A, the blade component 1204 is also sized to engage, or otherwise interface, the acetabular cup or shell 1000 when the variable angle blade augment 1200 is operably implanted in a patient. Again, such direct, physical engagement between the blade component 1204 and the acetabular cup or shell 1000 can enhance the structural support and/or stabilization provided by the variable angle blade augment 1200 to the acetabular cup or shell 1000 in recreating the acetabular rim in the host bone.

Figure 10A:
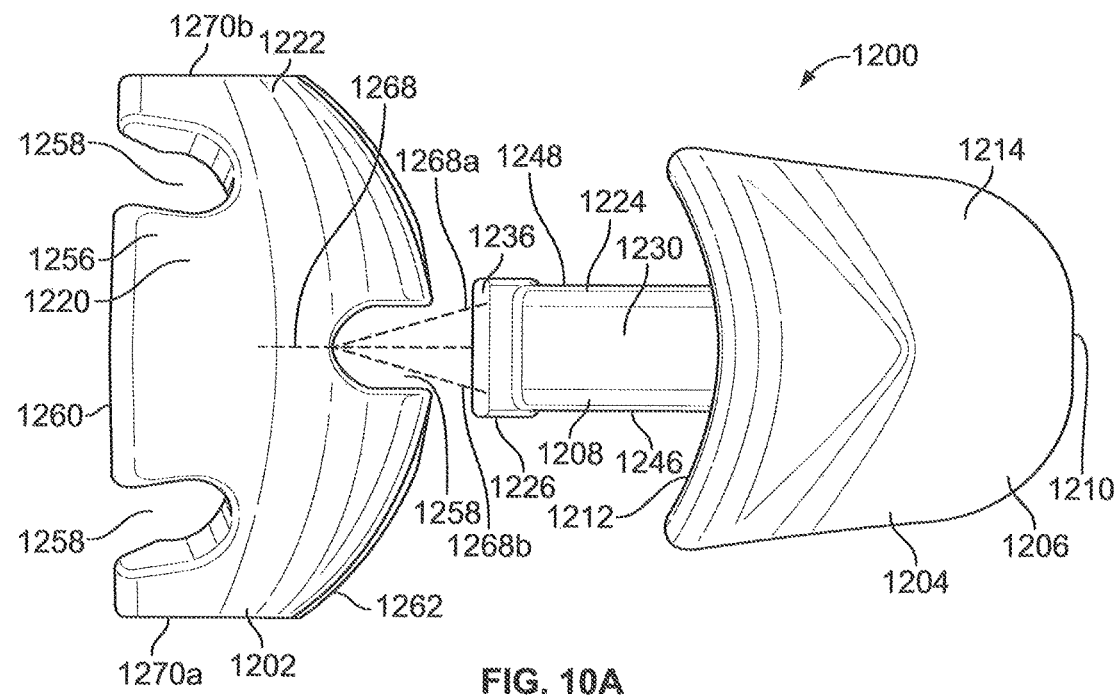
FIG. 10A illustrates an exploded back view of a variable angle blade augment having a slotted-type augment component and a separate blade component.
Figure 10B:
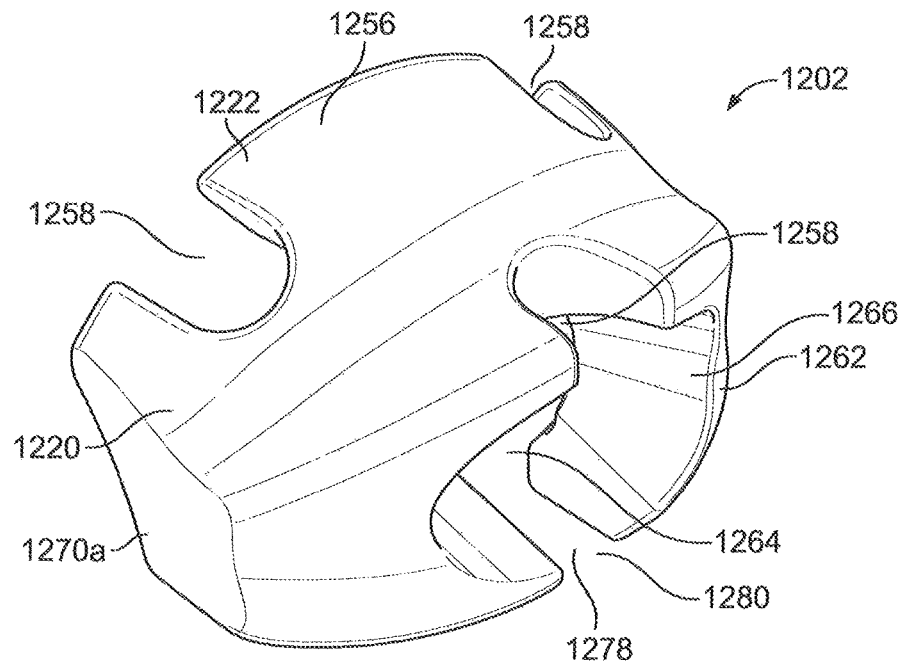
FIG. 10B illustrates a perspective back view of the slotted-type augment component shown in FIG. 10A.
Figure 10C:
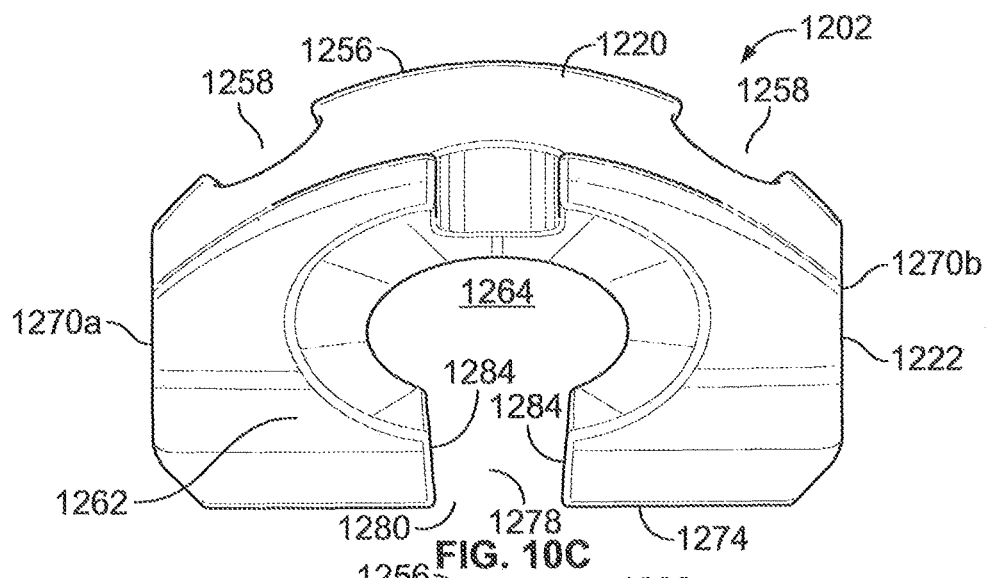
FIG. 10C illustrates a top view of the slotted-type augment component shown in FIG. 10A.
Figure 10D:
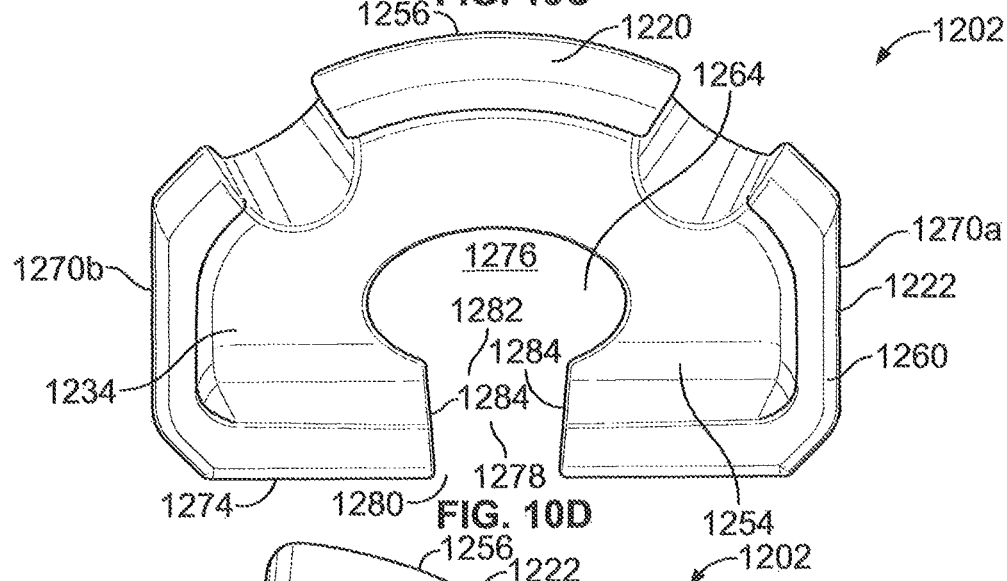
FIG. 10D illustrates a bottom view of the slotted-type augment component shown in FIG. 10A.
Figure 10E:
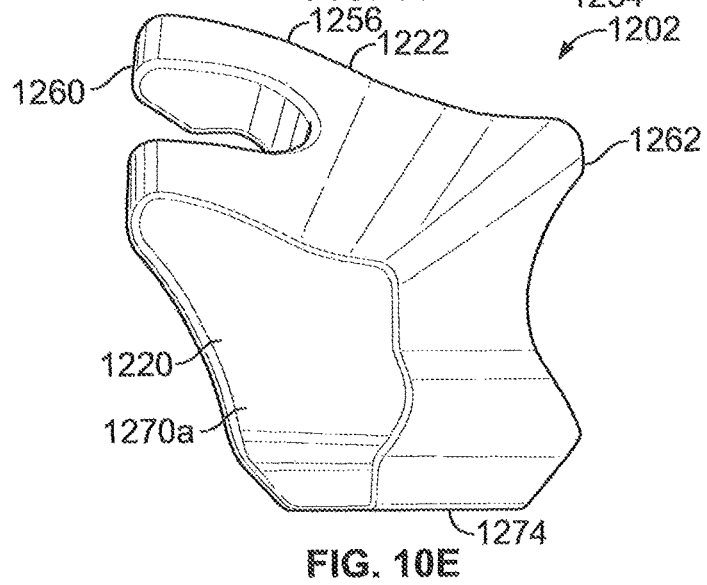
FIG. 10E illustrates a side view of the slotted-type augment component shown in FIG. 10A.
Figure 10F:
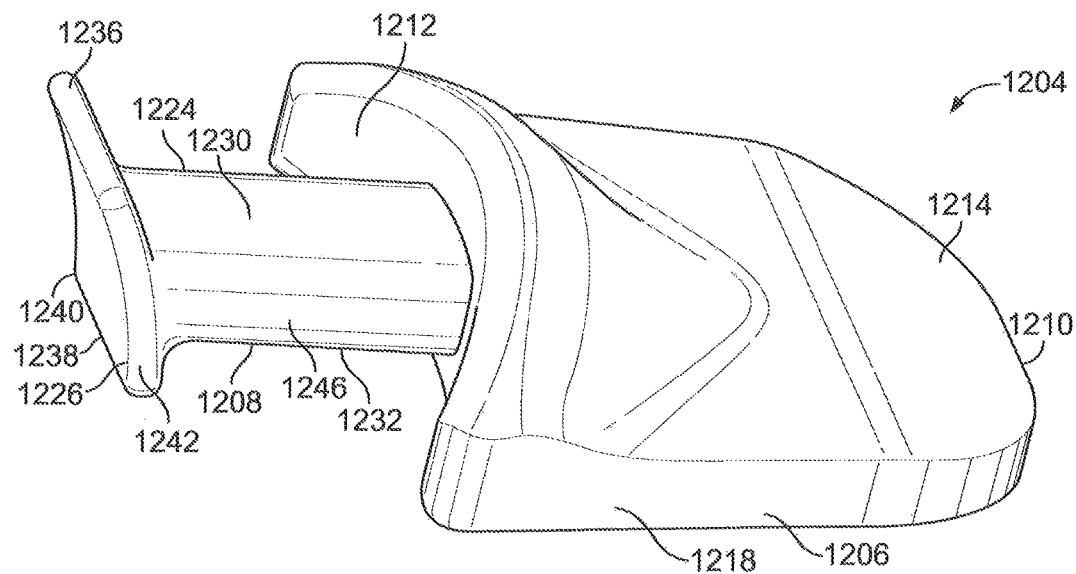
FIG. 10F illustrates a perspective side view of the blade component shown in FIG. 10A.
Figure 10G:
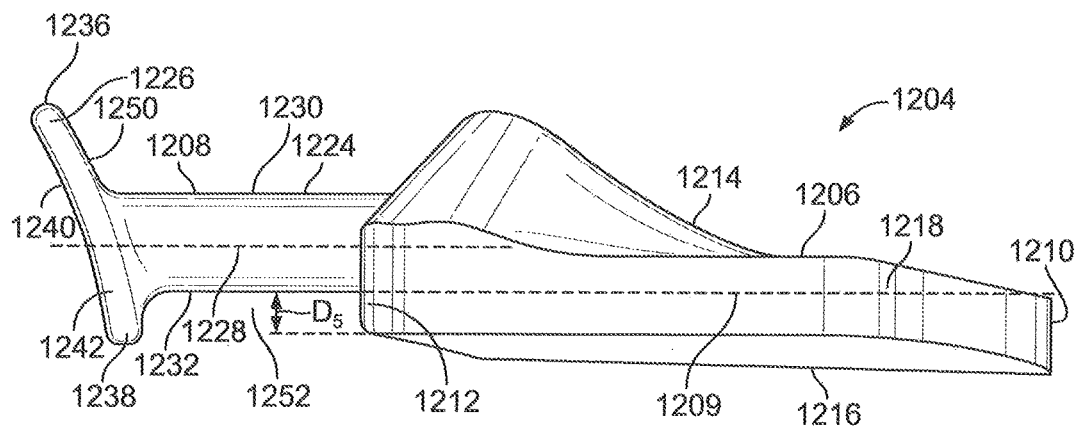
FIG. 10G illustrates a side view of the blade component shown in FIG. 10A.

Referencing at least FIGS. 10A, 10F and 10G, the blade component 1204 can include a buttress portion 1206 and a neck portion 1208. The buttress portion 1206 can extend along a central axis 1209 (FIG. 10G) of the buttress portion 1206 between a first end 1210 and a second end 1212 of the buttress portion 1206, and include a back side 1214 and an opposing front, or bone facing, side 1216. Further, according to certain embodiments, an outer blade wall 1218 can extend along an outer perimeter of at least a portion of the buttress portion 1206. The height or width of the outer blade wall 1218 can vary to at least accommodate differences in distances between portions of the opposing back and front sides 1214, 1216 of the buttress portion 1206 that are generally adjacent to the outer blade wall 1218, as shown, for example, by at least FIGS. 10F and 10G.

Unlike the buttress portion 1006 discussed above with respect to at least FIG. 9A, the buttress portion 1206 depicted in FIGS. 10A, 10F and 10G, as shown, does not include fixation holes 1024. However, according to other embodiments, the buttress portion 1206 can include fixation holes that are at least similar, if not the same, as the fixation holes 1024 that were previously discussed with respect to the buttress portion 1006.

As shown in at least FIGS. 10A and 10F, according to certain embodiments, at least a portion of the outer blade wall 1218 along the second end 1212 of the buttress portion 1206 can have a shape that generally mates, and/or conforms, to the shape of at least a portion of an outer surface 1220 of an augment wall 1222 of the augment component 1202 that the outer blade wall 1218 may engage, or otherwise be at least proximately adjacent to, when the variable angle blade augment 1200 is implanted or otherwise assembled. For example, as shown in at least FIG. 10A, at least a portion of the outer blade wall 1218 at the second end 1212 of the buttress portion 1206 can have a generally concave shape that is sized to generally mate with, and/or abut against, a mating convex shaped portion of the outer surface 1220 of the augment wall 1222 of the augment component 1202. Such mating shapes along the second end 1212 of the buttress portion 1206 and the outer surface 1220 of the augment component 1202 may at least increase the size of the surface area, and/or length of the distance, of the portion of the buttress portion 1206 that can be abutted against the augment component 1202, and thereby further enhance the strength and/or stability of the engagement between at least the blade component 1204 and the augment component 1202. Moreover, as the augment component 1202 may abut against at least a portion of the acetabular cup or shell 1000, an enhancement of the strength of the engagement between the blade component 1204 and the augment component 1202 may further enhance the strength and/or stability of the engagement between at least the augment component 1202 and the acetabular cup or shell 1000.

The neck portion 1208 includes a body segment 1224 and a face segment 1226. An end of the body segment 1224 can be connected to, and/or extend from, the second end 1212 of the buttress portion 1206. For example, according to certain embodiments, the body segment 1224 can extend from a portion of the outer blade wall 1218 and/or a portion of the back side 1214 of the buttress portion 1206 that is generally located around the second end 1212 of the buttress portion 1206. As shown, the body segment 1224 extends from a different location along the second end 1212 of the buttress portion 1206 than the location from which the body segment 1030 extends in the embodiment depicted in at least FIG. 9A. Further, for example, as shown in at least FIG. 10G, according to certain embodiments, the body segment 1224 can generally extend along a central axis 1228 of the neck portion 1208 that is parallel to, and linearly offset from, the central axis 1209 of the buttress portion 1206.

Similar to the buttress portion 1206, the body segment 1224 can have a back side 1230 and an opposing front, or bone facing, side 1232. As shown by at least FIG. 10G, according to the illustrated embodiment, at least a portion of the front side 1232 of the body segment 1224 can be linearly offset from the front side 1216 of the buttress portion 1206 by a distance (as shown by "$D_5$" in FIG. 10G) that can accommodate placement of at least a portion of the augment component 1202 below the front side 1232 of the body segment 1224 at least when of the face segment 1226 is positioned in, or through, an internal cavity 1234 (FIG. 10D) of the augment component 1202. Further, similar to the body segment 1030 discussed above, the body segment 1224 depicted in at least FIGS. 10A, 10F and 10G has a length that at least assists in the face segment 1226 being positionable at least when the variable angle blade augment 1200 is implanted at a location at which the face segment 1226 has direct physical contact with the acetabular cup or shell 1000.

The face segment 1226 includes at least a back side 1236, a front side 1238, and a bottom side 1240. Further, in view of at least the difference in length or width between the first and second sidewalls 1242, 1244 of the face segment 1226 in relation to the corresponding width between sidewalls 1246, 1248 of the body segment 1224, as well as difference between the back and front sides 1236, 1238 of the face segment 1226 in relation to the back and front sides 1230, 1232 of the body segment 1224, the illustrated face segment 1226 can also include a top side 1250. As discussed below in more detail, the front side 1238 of the face segment 1226 can be at least linearly offset from the front side 1216 of the buttress portion 1206 by a distance (as shown by "$D_5$" in FIG. 10G), while the front side 1238 of the face segment 1226 is approximately aligned with the front side 1216 of the buttress portion 1206 so that a gap 1252 beneath the body segment 1224 and between the face portion 1250 of the face segment 1226 and the second end 1212 of the buttress portion 1206 that can, according to certain embodiments, receive a portion of, or be relatively adjacent to, the augment wall 1222. Moreover, in a manner similar that discussed above with respect to the variable angle blade augment 1002 discussed above with respect to at least FIG. 9A, the presence of a portion of the augment wall 1222 in the gap 1252 when the blade component 1204 is assembled with the augment component 1202 can, according to certain embodiments, provide a barrier against linear displacement of the face segment 1226 out of the augment component 1202 in a manner that can at least assist in preventing removal of the face segment 1226 from the internal cavity 1234 of the augment component 1202.

According to certain embodiments, the face segment 1226 can extend between a first sidewall 1242 and a second sidewall 1244. Further, when compared with the body segment 1224, the relative distance between the back and front sides 1236, 1238 and/or between the first and second sidewalls 1242, 1244 can provide the neck portion 1208 with at least a generally "T" shaped appearance in one or more plane (as shown for example in FIGS. 10A, 10F and 10G). However, depending on the shape at or around the engagement/transition between the body segment 1224 and the buttress portion 1206, according to certain embodiments, the neck portion 1208 can have a generally "I" beam shaped appearance in at least one plane.

As shown in at least FIGS. 10F and 10G, according to the certain embodiments, at least a portion of the bottom side 1240 of the face segment 1226 is contoured to mate the shape of a corresponding surface of an acetabular cup or shell 1000 against which the face segment 1226 can abut or otherwise contact. For example, according to certain embodiments, the bottom side 1240 of the face segment 1226 can have a contour, such as, for example, a radius and/or concave curvature, among other shapes and/or contours, along at least a portion, if not approximately all, of the length of the bottom side 1240 of the face segment 1226. According to the embodiment illustrated in FIG. 10F, the bottom side 1240 of the face segment 1226 can have a curvature that generally extends between the back and front sides 1236, 1238 of the face segment 1226. However, according to other embodiments, the bottom side 1240 of the face segment 1226 can be contoured in a variety of other directions. As shown by at least FIG. 10G, the mating shape provided by the bottom side 1240 of the face segment 1226 can, at least according to certain embodiments, be sized to match a mating rounded outer surface or portion of the acetabular cup or shell 1000. Further, as shown in at least FIG. 10F, at least the bottom side 1240 of the face segment 1226 can be defined by generally parallel back and front sides 1236, 1238 and generally parallel first and second sidewalls 1242, 1244 such that, aside from the curvature or contouring of the bottoms side 1240, provide a generally square or rectangular appearance.

At least FIGS. 10A-10E also illustrate an example of an augment component 1202 that can be configured to be assembled with the blade component 1204 to provide the variable angle blade augment 1200. According to the illustrated embodiment, the augment component 1202 can comprise an augment wall 1222 having an outer surface 1220 and an inner surface 1254. The inner surface 1254 of the augment wall 1222 can generally define at least a portion of the internal cavity 1234 of the augment component 1202. The outer surface 1220 of the augment wall 1222 can generally define at least an external shape(s) of the augment component 1202 as well as provide a variety of different features for the augment component 1202.

As shown in at least FIGS. 10A-10E, a back side portion 1256 of the augment wall 1222 can include one or more cement ports 1258 that are in fluid communication with the internal cavity 1234, and, moreover, provide passageways through which cement can be injected into, or otherwise delivered to, the internal cavity 1234. The cement ports 1258 can have a variety of shapes, sizes, and configurations, including, for example, the configuration similar to the cement ports 1076 depicted in at least FIG. 9A. However, in the illustrated embodiment, each of the cement ports 1258 are positioned such that a portion of the wall that defines the passage to the internal cavity 1234 provided by the cement ports 1258 extends, or through, the bottom side portion 1260 and/or top side portion 1262 of the augment wall 1222 such that the cement portions 1258 are open along at least one side of the cement port 1258.

As shown in at least FIG. 10C, the augment wall 1222 can include a top side portion 1262. According to certain embodiments, at least a portion of the outer surface 1220 of the top side portion 1262 of the augment wall 1222 can be configured, such as, for example, sized, shaped, and/or oriented, for a mating engagement with, or otherwise for being positioned approximately adjacent to, the second end 1212 of the buttress portion 1206 of the blade component 1204. For example, as previously discussed and shown in at least FIG. 10A, the outer surface 1220 of the top side portion 1262 of the augment wall 1222 can have a rounded, curved, or convex shape that is generally similar to a rounded, curved, or concave shape of at least a portion of the second end 1212 of the buttress portion 1206 that can be positioned against, or in positioned approximately adjacent to, the augment wall 1222.

The top side portion 1262 of the augment wall 1222 can include a first opening 1264 that is in communication with the internal cavity 1234. The first opening 1264 can be sized to accommodate passage of the body segment 1224 of the neck portion 1208 through the first opening 1264 at least when a portion of the face segment 1226 is operably positioned in the internal cavity 1234. Further, the first opening can be sized to accommodate linear and/or angular adjustment of the position of the body segment 1224 within the first opening 1264, and thereby accommodate a relatively wide range of angulation between the blade component 1204 and the augment component 1202.

According to the depicted embodiment, the first opening 1264 is generally defined by an opening wall 1266 that is outwardly tapered as the opening wall 1266 extends generally from an area adjacent to the internal cavity 1234 to an area generally adjacent to the top side portion 1262 of the augment wall 1222. Thus, according to such a configuration, the size of the first opening 1264 adjacent to the internal cavity 1234 may be smaller than the size of the first opening 1264 adjacent to the top side portion 1262 of the augment wall 1222. When the body segment 1224 is operably positioned in the first opening 1264, such a configuration of the first opening 1264, as well as the size of the body segment 1224 between the sidewalls 1246, 1248, can at least accommodate pivotal and/or rotational displacement of the body segment 1224, and thus of the blade component 1204, relative to the centered, neutral position (as indicated by the centerline 1268 in FIG. 10A) of the blade component 1204 when assembled with the augment component 1202. Two non-limiting examples of such pivotal and/or rotational displacement of the body segment 1224, and thus of the blade component 1204, relative to the augment component 1202 are, for purposes of illustration, indicated by the changes in the centerline 1268a, 1268b. While such examples depict pivotal or rotational adjustment in the position of the centerline 1268 in a single plane, according to certain embodiments, the tapered configuration and size of the opening wall 1266 can, in at least some embodiments, accommodate relative pivotal or rotational displacement of the blade component 1204 in other directions or planes. Additionally, according to certain embodiments, the first opening 1264 can also be sized to accommodate linear displacement of the body segment 1224 in a variety of directions, and thus accommodate adjustments to the relative linear positions of the blade component 1204 and the augment component 1202.

According to certain embodiments, at least a portion of the bone facing sides of the outer surface 1220 of the augment wall 1222, such as for example, at least a portion of the top side portion 1262 and/or sidewall portions 1270a, 1270b of the outer surface 1220 of the augment wall 1222 can also include a retention ridge or lip 1272. The retention lip 1272 can have a variety of shapes and sizes, and can be generally configured to provide a barrier against, or to minimize, the flow, if any, of cement into the host bone. For example, according to the illustrated embodiment, the retention lip 1272 generally outwardly protrudes away from adjacent portions of the outer surface of the augment wall 1222 so as to provide a barrier that at least attempts to stop the flow, or otherwise catch, cement that may pass along or around at least a portion of the outer surface 1220 of the augment wall 1222. While the retention lip 1272 can be positioned at a variety of locations about the bone facing sides of the augment wall 1222, according to the illustrated embodiment, the retention lip 1272 can be generally located in the between the first opening 1264 and the front side portion 1274 of the outer surface 1220 of the augment wall 1222, as indicated, for example, by FIG. 10E.

The augment wall 1222 also includes a bottom side portion 1260, as shown in at least FIG. 10D that is configured to abut, or otherwise be positioned proximally adjacent to, the acetabular cup or shell 1000. Thus, at least the outer surface 1220 of the augment wall 1222 along at least a portion of the bottom side portion 1260 can have a shape and/or contours that generally mate the shape of at least the portion of the acetabular cup or shell 1000 against which the augment component 1202 can abut. Additionally, the bottom side portion 1260 of the augment wall 1222 can be configured to generally define a second opening 1276 in the augment component 1202. The second opening 1276 is in fluid communication with the internal cavity 1234 and sized to accommodate the face segment 1226 of the blade component 1204 being in direct contact with the acetabular cup or shell 1000. For example, according to certain embodiments, the second opening 1276 can be sized to receive insertion of at least a portion of at one of the acetabular cup or shell 1000 and the face segment 1226 of the blade component 1204. Further, according to certain embodiments, the face segment 1226 of the blade component 1204 can be in direct contact with the acetabular cup or shell 1000 at, or in the general vicinity of, the second opening 1276.

As shown in at least FIGS. 10B-10D, the augment component 1202 includes a slot 1278 that extends through the augment wall 1222 and is in communication with the first and second openings 1264, 1276. According to certain embodiments, the slot 1278 has a first end 1280 in the front side portion 1276 of the augment wall 1222 and a second end 1282 that extends through the opening wall 1266 of the first opening 1264. Additionally, as shown by at least FIG. 10C, the slot 1278 can also extend through a portion of the top side portion 1262 of the augment wall 1222.

The slot 1278 can be generally defined by an opposing pair of slot walls 1284. According to certain embodiments, the slot walls 1284 can be inwardly tapered generally from the internal cavity 1234 and/or first opening 1264 toward the front side portion 1274 of the augment wall 1222. Thus, the first end 1280 of the slot 1278 can have a smaller width between the slot walls 1284 than the second end 1282 of the slot 1278. Further, according to certain embodiments, the distance between the opposing slot walls 1284 can be used to control at least the placement, as well as removal, of the body segment 1224 into/from the first opening 1264, and moreover control the assembly/disassembly of the blade component 1204 to/from the augment component 1202.

For example, according to certain embodiments, the distance between the opposing slot walls 1284 at least at the first end 1280 of the slot may be smaller than the distance between the opposing sidewalls 1246, 1248 of the body segment 1224, but larger than the distance between the opposing back and front sides 1230, 1232 of the body segment 1224. According to such an embodiment, assembly of the blade component 1204 to the augment component 1202 may be limited to situations in which the blade component 1204 has been manipulated, such as rotated, such that the opposing back and front sides 1230, 1232 of the body segment 1224 are generally aligned with the slot walls 1284 at the first end 1280 of the slot 1278. Such manipulation may include, for example, rotating the blade component 1204 about 90 degrees from the relative orientation shown in FIG. 10A. With the smaller sized of the width between the back and front sides 1230, 1232 of the body segment 1224 are generally aligned with the slot walls 1284 at the first end 1280 of the slot 1278, the blade component 1204 can be displaced relative to the augment component 1202 such that the body segment 1224 is moved along the slot 1278 to a position at which at least a portion of the body segment 1224 is received in the first opening 1264. Moreover, the body segment 1224 can be moved at least into a portion of the first opening 1264 such that the body segment 1224, and thus the blade component 1204, can be rotated back to a position at which the back and front sides 1230, 1232 of the body segment 1224 are generally perpendicular, or otherwise misaligned, with the slot walls 1284 at the second end 1282 of the slot 1278. Thus, according to certain embodiments, the first opening 1264 may be shaped and sized to accommodate such rotation of the body segment 1224. For example, in the illustrated embodiment, the first opening 1264 can have a generally oval shape, among other shapes, that can accommodate such rotation of the body segment 1224, as well as accommodate off-centered linear positioning of the blade component 1204 relative to the augment component 1202, as previously discussed. Additionally, the second end 1282 of the slot 1278 can have a size that can at least assist in preventing the slots walls 1284 from interfering with such rotational displacement of the body segment 1224.

Additionally, according to at least some embodiments, the face segment 1226 can have a size that prevents the passage of the face segment 1226 through the first opening 1264. Such differences in sizing can at least assist in retaining the blade component 1204 in assembly with the augment component 1202. For example, according to certain embodiments, the face segment 1226 can have a length between the opposing back side 1236 and front side 1238 of the face segment 1226 that is greater than a width of a corresponding adjacent portion of the first opening 1264. According to such an embodiment, portions of the inner surface 1254 of the augment wall 1222, including, but not limited to, portions of the inner surface 1254 of the augment wall 1222 positioned in the gap 1252 between the face segment 1226 and the buttress portion 1206, can at least assist in preventing the passage of the face segment 1226 through the first opening 1264.

The body segment 1224 of the blade component 1204 can also be sized, such as, for example, have a length, to accommodate linear adjustment in the location of at least the face segment 1226 relative to the augment component 1202 and/or the acetabular cup or shell 1200. Moreover, such body segment 1224 have a length that can accommodate adjusting the linear location of at least the face segment 1226 such that the face segment 1226 can be displaced to a location at which at least a portion of the face segment 1226 can abut the acetabular cup or shell 1000. For example, the body segment 1224 can have a length between the second end 1212 of the buttress portion 1206 and the top side 1250 of the face segment 1226 that can accommodate at least linear adjustments in the positioning of the body segment 1224 relative to at least the first opening 1264 so as to facilitate the face segment 1226 being positioned to contact the acetabular cup or shell 1000.

In the illustrated embodiment, the front side portion 1276 of the augment wall 1222 can have a configuration that, with at least the exception of the slot 1278, is generally similar to at least the configuration of the front side portion 1084 of the augment wall 1028 of the augment component 1004 shown in at least FIG. 9E.

FIGS. 11A-11G illustrate an exemplary variable angle blade augment 1300. As depicted, the variable angle blade augment 1300 includes an augment component 1302 and a blade component 1304. Further, similar to the previously discussed blade components, the blade component 1304 is also sized to engage, or otherwise interface, the acetabular cup or shell 1000 when the variable angle blade augment 1300 is operably implanted in a patient.

Figure 11D:
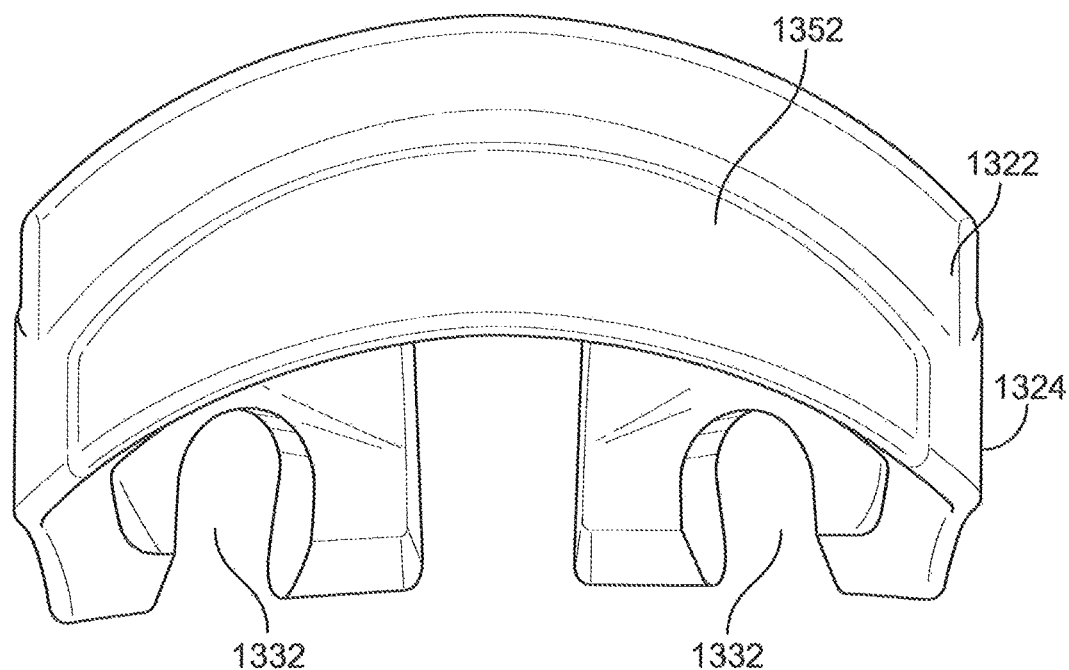
FIG. 11D illustrates a front view of the slotted-type augment component shown in FIG. 11A.
Figure 11E:
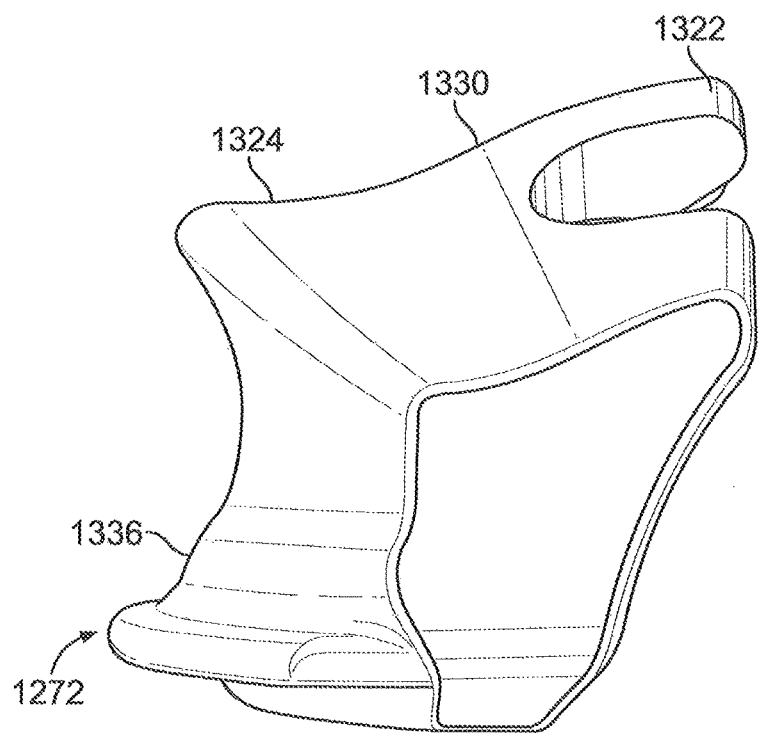
FIG. 11E illustrates a side view of the slotted-type augment component shown in FIG. 11A.
Figure 11F:
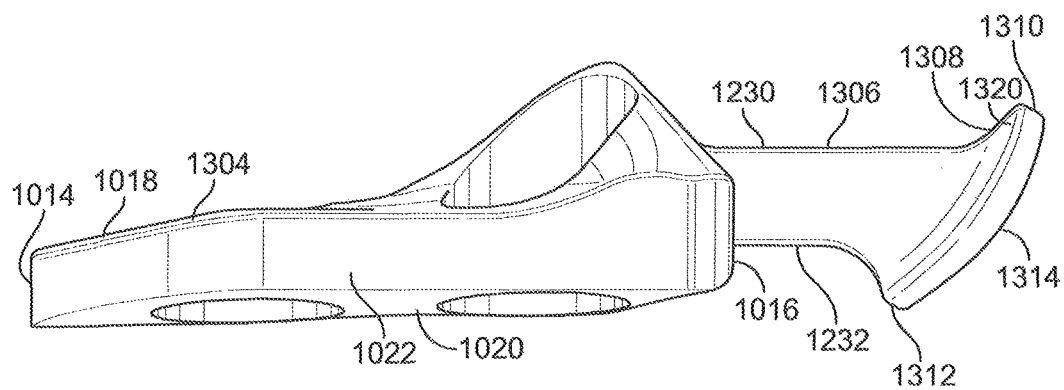
FIG. 11F illustrates a side view of the blade component shown in FIG. 11A.
Figure 11G:
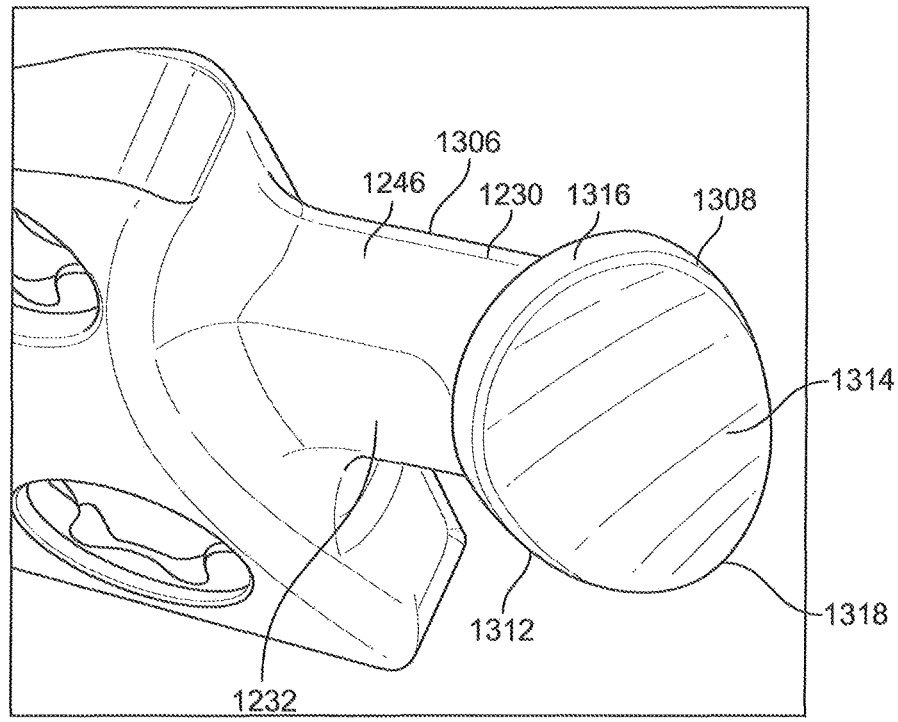
FIG. 11G illustrates a side perspective view of the blade component shown in FIG. 11A.

The blade component 1304 depicted in at least FIGS. 11A, 11F and 11G has many features similar to those previously discussed with respect to the blade components 1006, 1204 depicted in at least FIGS. 9A and 10A. For example, the blade component 1304 can include a buttress portion 1008 having a configuration similar to that discussed with respect to the blade component 1006 discussed with respect to at least FIG. 9A. Further, the neck portion 1306 can include a body segment 1224 similar to that previously discussed with respect to the blade component 1204 illustrated in FIG. 10A, although the body segments shown in FIGS. 10A and 11A are at least depicted as having different overall lengths.

The face segment 1308 of the neck portion 1306 depicted in at least FIGS. 11A, 11F and 11G can include at least a back side 1310, a front side 1312, and a bottom side 1314. Further, in view of at least the difference in length or width between the first and second sidewalls 1316, 1318 of the face segment 1308 in relation to the corresponding width between sidewalls 1246, 1248 of the body segment 1224, as well as difference between the back and front sides 1310, 1312 of the face segment 1308 in relation to the back and front sides 1230, 1232 of the body segment 1224, the illustrated face segment 1308 can also include a top side 1320.

According to certain embodiments, the face segment 1308 can extend between a first sidewall 1316 and a second sidewall 1318. Further, when compared with the body segment 1224, the relative distance between the back and front sides 1310, 1312 and/or between the first and second sidewalls 1316, 1318 can provide the neck portion 1306 with at least a generally "T" shaped appearance in one or more plane (as shown for example in FIGS. 11A and 11F). However, depending on the shape at or around the engagement/transition between the body segment 1224 and the buttress portion 1008, according to certain embodiments, the neck portion 1306 can have a generally "I" beam shaped appearance in at least one plane.

As shown in at least FIGS. 11F and 11G, according to the certain embodiments, at least a portion of the bottom side 1314 of the face segment 1308 is contoured to mate the shape of a corresponding surface of an acetabular cup or shell 1000 against which the face segment 1308 can abut or otherwise contact. For example, according to certain embodiments, the bottom side 1314 of the face segment 1308 can have one or more contours, such as, for example, one or more radius and/or concave curvatures, among other shapes and/or contours, along at least a portion, if not approximately all, of the length of the bottom side 1314 of the face segment 1308. According to the embodiment illustrated in FIG. 11G, the bottom side 1314 of the face segment 1308 can have one or more curvatures that provide the bottom side 1314 with a generally rounded shape. For example, the bottom side 1314 may be generally rounded in multiple directions, such as, for example, at least between the back and front sides 1310, 1312 and the sidewalls 1316, 1318 of the bottom side 314 of the face segment 1308.

At least FIGS. 11A-11E also illustrate an example of an augment component 1302 that can be configured to be assembled with the blade component 1304 to provide the variable angle blade augment 1300. Similar to the blade component 1304, the augment component 1302 can incorporate a variety of the previously features of the augment components 1004, 1202 that were discussed with respect to at least FIGS. 9A and 10A.

According to the illustrated embodiment, the augment component 1302 can comprise an augment wall 1322 having an outer surface 1324 and an inner surface 1326. The inner surface 1326 of the augment wall 1322 can generally define at least a portion of the internal cavity 1328 of the augment component 1302. The outer surface 1324 of the augment wall 1322 can generally define at least an external shape(s) of the augment component 1302 as well as provide a variety of different features for the augment component 1302.

A back side portion 1330 of the augment wall 1322 can include one or more cement ports 1332 that are in fluid communication with the internal cavity 1328, and, moreover, provide passageways through which cement can be injected into, or otherwise delivered to, the internal cavity 1328. While the cement ports 1332 can have a variety of shapes, sizes, and configurations, similar to the cement ports 1258 illustrated in at least FIG. 10A, the depicted cement ports 1332 are positioned such that a portion of the wall that defines the passage to the internal cavity 1328 provided by the cement ports 1332 extends, or through, the bottom side portion 1334 of the augment wall 1322.

As shown in at least FIG. 10C, the augment wall 1322 can include a top side portion 1336. According to certain embodiments, at least a portion of the outer surface 1324 of the top side portion 1336 of the augment wall 1322 can be configured, such as, for example, sized, shaped, and/or oriented, for a mating engagement with, or otherwise for being positioned approximately adjacent to, the second end 1212 of the buttress portion 1008 of the blade component 1304. For example, as previously discussed and shown in at least FIG. 11A, the outer surface 1324 of the top side portion 1336 of the augment wall 1322 can have a rounded, curved, or convex shape that is generally similar to a rounded, curved, or concave shape of at least a portion of the second end 1212 of the buttress portion 1008 that can be positioned against, or in positioned approximately adjacent to, the augment wall 1322.

The top side portion 1336 of the augment wall 1322 can include a first opening 1338 that is in communication with the internal cavity 1328. The first opening 1338 can be sized to accommodate passage of the body segment 1224 of the neck portion 1306 through the first opening 1338 at least when a portion of the face segment 1308 is operably positioned in the internal cavity 1328. Further, in at least a manner similar to that described above with respect to the first opening 1264 and augment component 1202 shown in at least FIG. 10A, the first opening 1338 can be sized to accommodate linear and/or angular adjustment of the position of the body segment 1224 within the first opening 1338, and thereby accommodate a relatively wide range of angulation between the blade component 1304 and the augment component 1302.

According to the depicted embodiment, the first opening 1338 is generally defined by an opening wall 1340 that is outwardly tapered as the opening wall 1340 extends generally from an area adjacent to the internal cavity 1328 to an area generally adjacent to the top side portion 1336 of the augment wall 1322. Thus, according to such a configuration, the size of the first opening 1338 adjacent to the internal cavity 1328 may be smaller than the size of the first opening 1338 adjacent to the top side portion 1336 of the augment wall 1322. When the body segment 1224 is operably positioned in the first opening 1338, such a configuration of the first opening 1338, as well as the shape and/or size of the body segment 1224 between the sidewalls 1246, 1248, can at least accommodate pivotal and/or rotational displacement of the body segment 1224, and thus of the blade component 1304, relative to the centered, neutral position of the blade component 1204. Such angular adjustment(s) of the blade component 1304 as well as linear adjustments, relative to the augment component 1302 can be in a manner that is similar to that previously illustrated and discussed with respect to the exemplary adjustment of the position of the centerline 1268 depicted in FIG. 10A.

The augment wall 1322 also includes a bottom side portion 1334, as shown in at least FIG. 10D that is configured to abut, or otherwise be positioned proximally adjacent to, the acetabular cup or shell 1000. Additionally, the bottom side portion 1334 of the augment wall 1322 can be configured to generally define a second opening 1342 in the augment component 1302. Similar to the previously discussed second openings 1108, 1276 the second opening 1342 is in fluid communication with the internal cavity 1328 and sized to accommodate the face segment 1308 of the blade component 1304 being in direct contact with the acetabular cup or shell 1000.

Similar to the augment component 1202 shown in at least FIG. 10A, the augment component 1302 shown in at least FIGS. 11B-11D includes a slot 1344. Although the slots 1278, 1344 of the augment components 1202, 1304 can have a similar construction, the first end 1346 of the slot 1344 of the augment component 1304 can be positioned at the back side portion 1330 of the augment wall 1322. Further, similar to the previously discussed slot 1278, the slot 1344 depicted in at least FIG. 11A can have tapered slot walls 1350 such that the second end 1348 is larger than the first end 1346 of the slot 1344. Accordingly, the slot 1344 and the first opening 1338 can be sized and/or shaped to control the insertion/removal of the body segment 1224 into/from the slot 1344 and the first opening 1338 in a manner similar to that previously discussed with respect to the slot 1278 and first opening 1264. Additionally, similar to the first opening 1264 and face segment 1226 previously discussed, at least the face segment 1308 of the blade component 1302 and the first opening 1338 can also have a size and/or shape that prevents the passage of the face segment 1308 through the first opening 1338.

In the illustrated embodiment, the front side portion 1352 of the augment wall 1322 can have a configuration that, with at least the exception of the slot 1344, is generally similar to at least the configuration of the front side portion 1084 of the augment wall 1028 of the augment component 1004 shown in at least FIG. 9E.

Figure 12A:
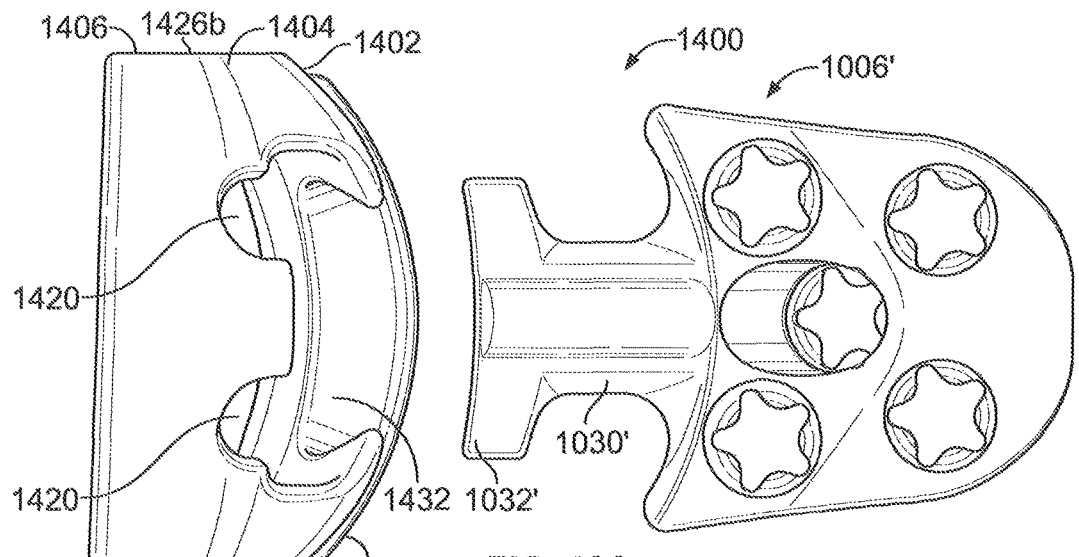
FIG. 12A illustrates an exploded back view of a variable angle blade augment having a keyed-type augment component and a separate blade component.

FIGS. 12A-12G illustrate another exemplary variable angle blade augment 1400. As depicted, the variable angle blade augment 1300 includes an augment component 1402 and a blade component 1006'. For purposes of discussion, the blade component 1006' illustrated in FIG. 12A is generally similar, although shorted in overall length, to the blade component 1006 discussed with respect to at least FIG. 9A. Further, while a least FIGS. 9A, 10A, 11A and 12A illustrate variable angle blade augments 1000, 1200, 1300, 1400 comprising particular combinations of augment components 1004, 1202, 1302 and blade components 1006, 1006', 1204, 1304, various variable angle blade augments can comprise different combinations of augment components 1004, 1202, 1302 and blade components 1006, 1006', 1204, 1304, which can also have a variety of difference shapes, sizes, and/or features, or combinations thereof.

According to the illustrated embodiment, the augment component 1402 can comprise an augment wall 1404 having an outer surface 1406 and an inner surface 1408. The inner surface 1408 of the augment wall 1404 can generally define at least a portion of the internal cavity 1410 of the augment component 1402. The outer surface 1406 of the augment wall 1404 can generally define at least an external shape(s) of the augment component 1402 as well as provide a variety of different features for the augment component 1402. Further, similar to the previously discussed augment components 1004, 1202, 1302 and associated features, the augment component 1402 can include a back side portion 1412, a bottom side portion 1414, top side portion 1416, and a front side portion 1418.

The top side portion 1416 of the augment wall 1404 can include a first opening 1422 that is at least partially defined by an opening wall 1424 and is in communication with at least the internal cavity 1410. The first opening 1422 can be sized to accommodate passage of the body segment 1030' of the neck portion 1306 through the first opening 1422 at least when a portion of the face segment 1308 is operably positioned in the internal cavity 1410. According to the illustrated embodiment, the first opening 1422 has a generally trapezoidal shape, with the trapezoidal shape extending outwardly as the first opening 1422 extends in the general direction of the front side portion 1418 of the augment wall 1404. Further, in at least a manner similar to that described above with respect to at least the first openings 1090, 1264 and augment components 1004, 1202 shown in at least FIGS. 9A and 10A, the first opening 1422 can be sized and/or shaped to accommodate linear and/or angular adjustment of the position of the body segment 1030' within the first opening 1422, and thereby accommodate a relatively wide range of angulation between the blade component 1006' and the augment component 1402. Thus, when the body segment 1030' is operably positioned in the first opening 1422, such a configuration of the first opening 1422, as well as the shape and/or size of the body segment 1030' between the sidewalls 1246, 1248, can at least accommodate pivotal and/or rotational displacement of the body segment 1030', and thus of the blade component 1006', relative to the centered, neutral position of the blade component 1204. Such angular adjustment(s) of the blade component 1006' as well as linear adjustments, relative to the augment component 1402 can be in a manner that is similar to that previously illustrated and discussed with respect to the exemplary adjustment of the position of the centerlines 1012, 1268 depicted in at least FIGS. 9A and 10A.

Figure 12B:
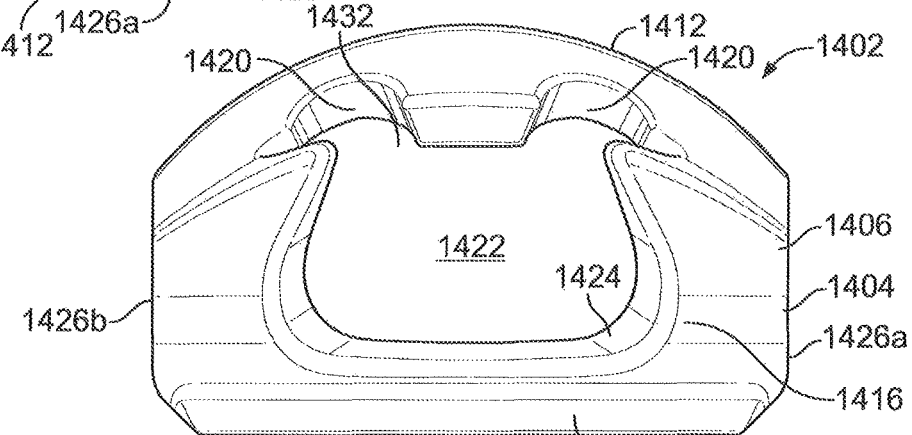
FIG. 12B illustrates a top view of the keyed-type augment component shown in FIG. 12A.
Figure 12C:
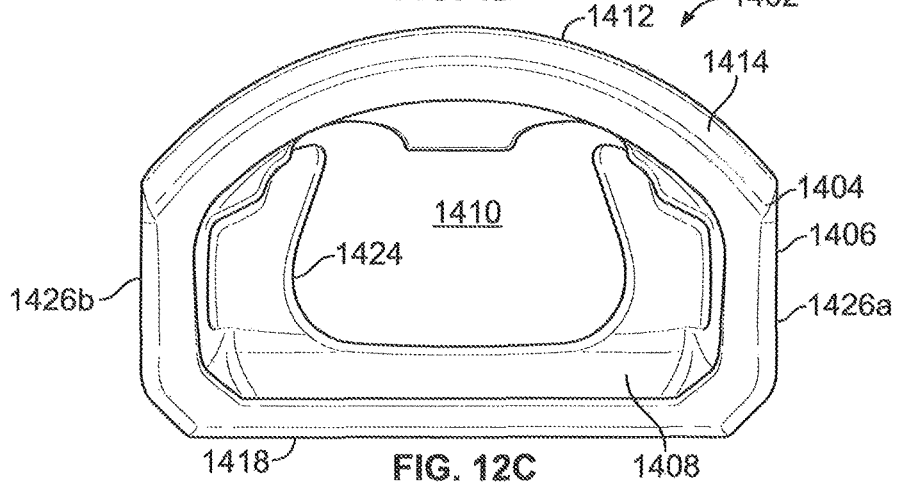
FIG. 12C illustrates a bottom view of the keyed-type augment component shown in FIG. 12A.
Figure 12D:
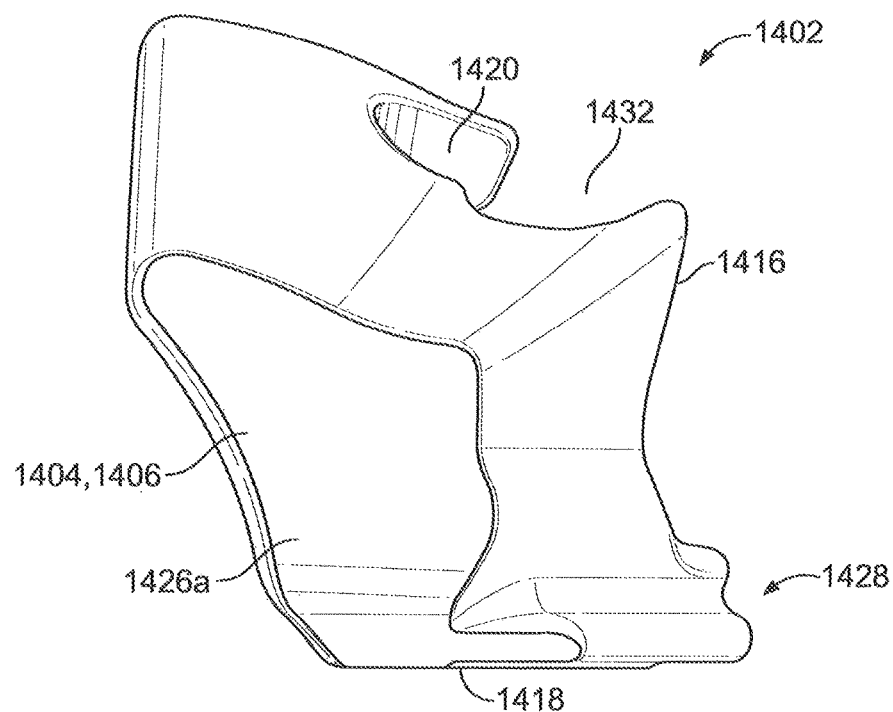
FIG. 12D illustrates a side view of the keyed-type augment component shown in FIG. 12A.
Figure 12E:
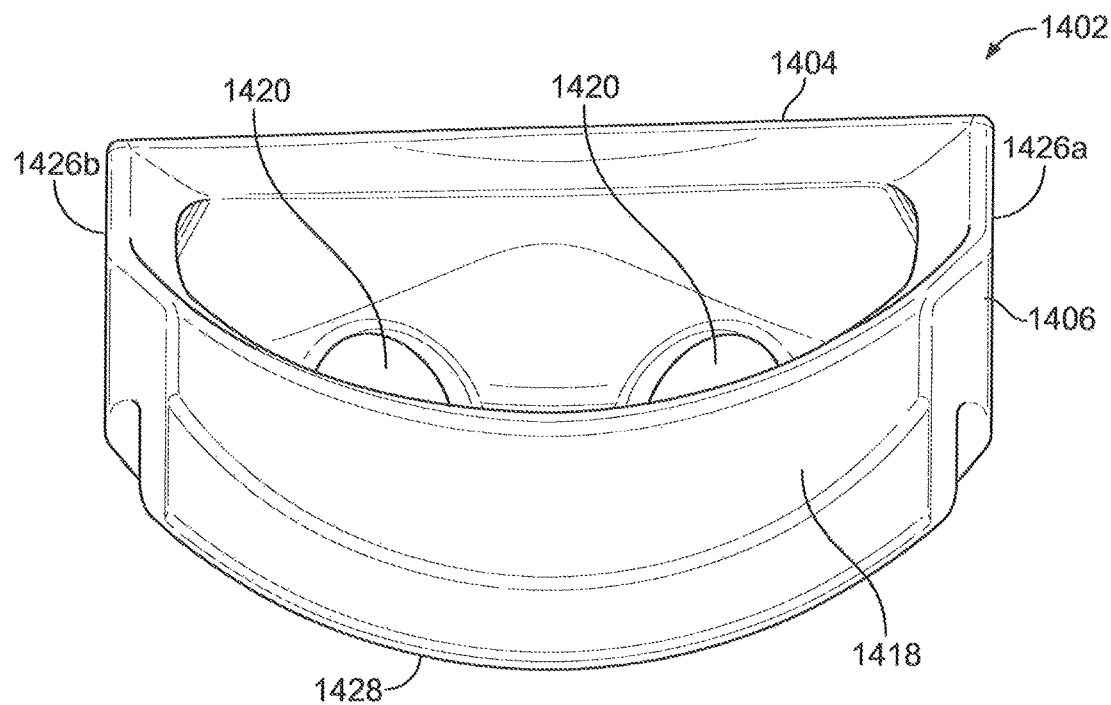
FIG. 12E illustrates a front view of the keyed-type augment component shown in FIG. 12A.

As shown in at least FIGS. 12A, 12B and 12D, similar to at least the augment component 1004 shown in at least FIG. 9A, at least a portion of the bone facing sides of the outer surface 1406 of the augment wall 1404, such as for example, at least a portion of the top side portion 1416 and/or sidewall portions 1426a, 1426b of the outer surface 1406 of the augment wall 1404 can also include a retention ridge or lip 1428. As previously discussed, the retention lip 1428 can be generally configured to provide a barrier against, or to minimize, the flow, if any, of cement into the host bone.

The bottom side portion 1414, as shown in at least FIG. 12C, can be configured to abut, or otherwise be positioned proximally adjacent to, the acetabular cup or shell 1000, and generally defines a second opening 1430 in the augment component 1402. Similar to at least the previously discussed second openings 1108, 1276, the second opening 1430 is in fluid communication with the internal cavity 1410 and sized to accommodate the face segment 1032' of the blade component 1006' being in direct contact with the acetabular cup or shell 1000.

As shown in at least FIGS. 12A, 12B and 12D, the augment component 1402 also includes a slot 1432 that is sized to receive insertion of the face segment 1032'. However, as shown by FIG. 12A, in the illustrated embodiment, the slot 1432 has a shape and/or configuration that is similar to that of the face segment 1032'. Thus, according to such an embodiment, the slot 1432 can be a keyway type opening that can limit, and thus control, the insertion of the face segment 1032' into the slot 1432 to a limited number of relative orientations and/or relative positions between the blade component 1006' and the augment component 1402. Moreover, by configuring the slot 1432 to have both a similar shape and size as a particular profile of the face portion 1030', the face portion 1030' may not be able to pass through the slot 1432 unless the face segment 1032' is linearly aligned with the slot 1432 and has an angular orientation(s) that can facilitate passage of the face portion face segment 1032' through the slot 1432.

In the illustrated embodiment, the slot 1432 is positioned about at least a portion of the back side portion 1412 of the augment wall 1404, and at a location that is proximately adjacent to the top side portion 1416 of the augment wall 1404. Additionally, the slot 1432 can extend through a portion of the top side portion 1416 of the augment wall 1404 so as to accommodate for the passage of at least a portion of the body segment 1030' through the slot and to first opening 1422. Thus, the slot 1432 is in communication with the first opening 1422, as well as with the internal cavity 1410 so that the face segment 1032' can pass through the slot 1432 and into the internal cavity 1410.

The back side portion 1412 of the augment wall 1404 can also include one or more cement ports 1420 that are in fluid communication with the internal cavity 1410, and, moreover, provide passageways through which cement can be injected into, or otherwise delivered to, the internal cavity 1410. The cement ports 1420 can have a variety of shapes, sizes, and configurations. Further, while the cement ports 1420 can be positioned at a variety of locations, the depicted cement ports 1420 are positioned such that a portion of the wall that defines the passage to the internal cavity 1410 provided by the cement ports 1420 extends through the augment wall 1404 and into the slot 1432 the top side portion 1416 of the augment wall 1404.

FIGS. 13A-13E illustrate another exemplary augment component 1500 that can be used with a variety of different blade components 1006, 1006', 1204, 1304. According to the illustrated embodiment, the augment component 1500 can comprise an augment wall 1502 having an outer surface 1504 and an inner surface 1506. The inner surface 1506 of the augment wall 1502 can generally define at least a portion of the internal cavity 1508 of the augment component 1500. The outer surface 1504 of the augment wall 1502 can generally define at least an external shape(s) of the augment component 1500 as well as provide a variety of different features for the augment component 1500. Further, similar to the previously discussed augment components 1004, 1202, 1302 and associated features, the augment component 1500 can include a back side portion 1510, a bottom side portion 1512, top side portion 1514, and a front side portion 1516.

Figure 13A:
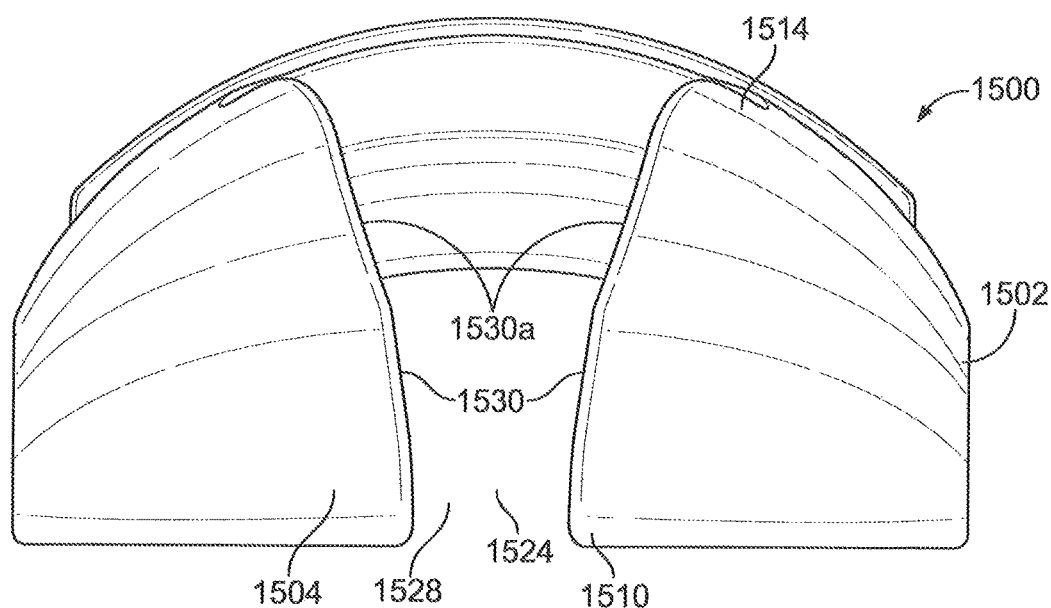
FIG. 13A illustrates a back view of a keyed-type augment component.
Figure 13B:
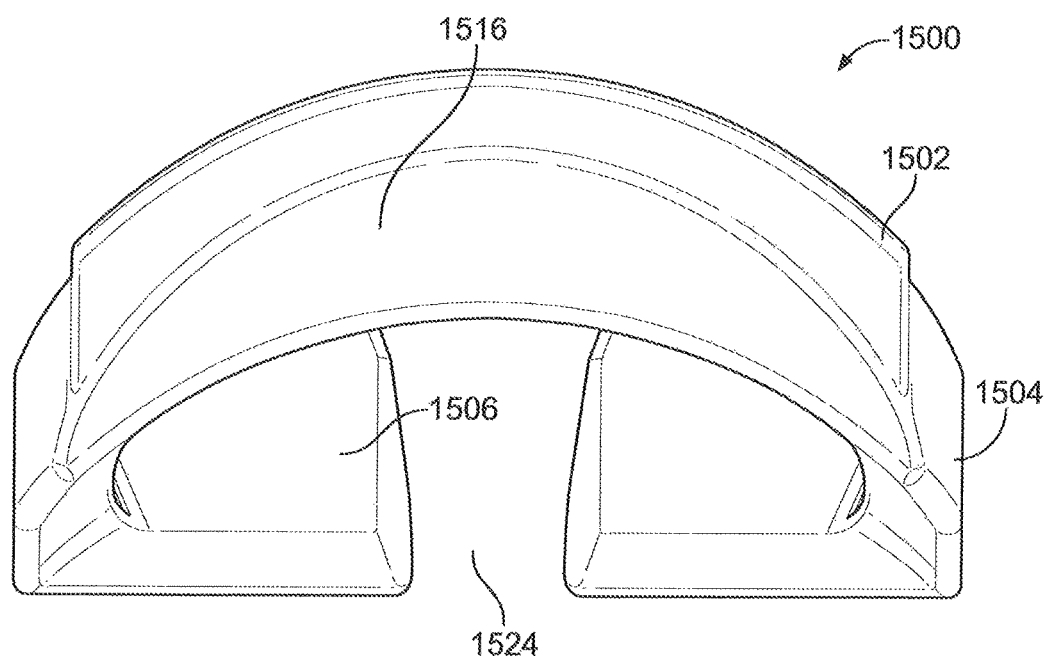
FIG. 13B illustrates a front view of the keyed-type augment component shown in FIG. 13A.
Figure 13C:
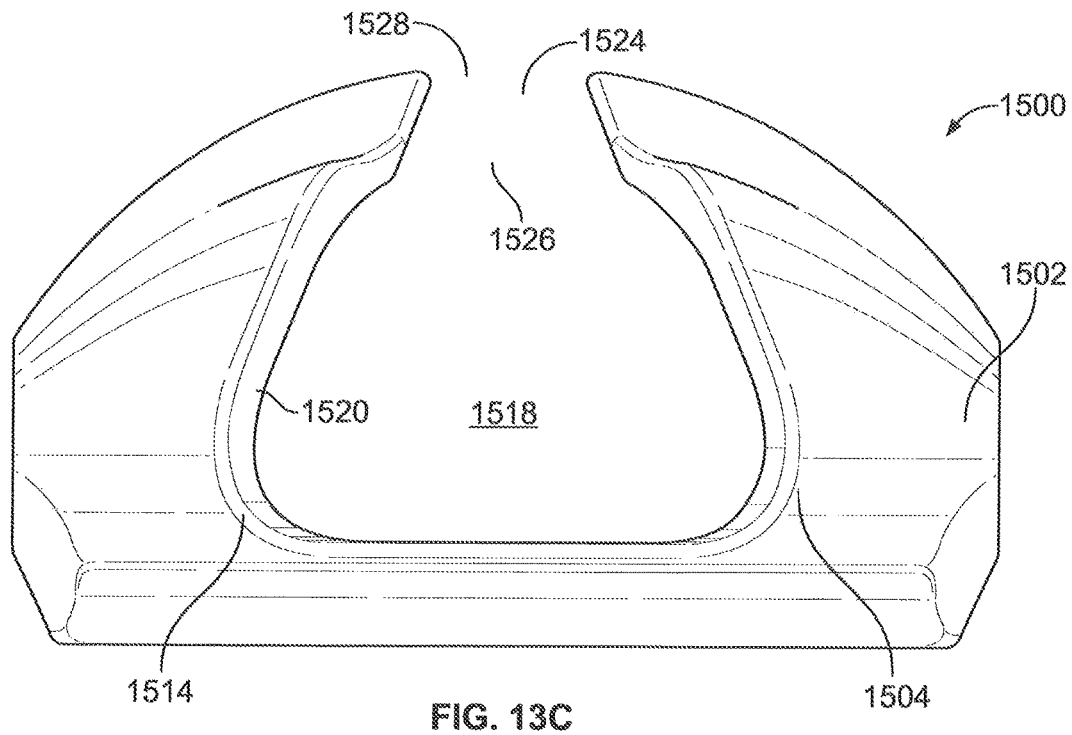
FIG. 13C illustrates a top view of the keyed-type augment component shown in FIG. 13A.
Figure 13D:
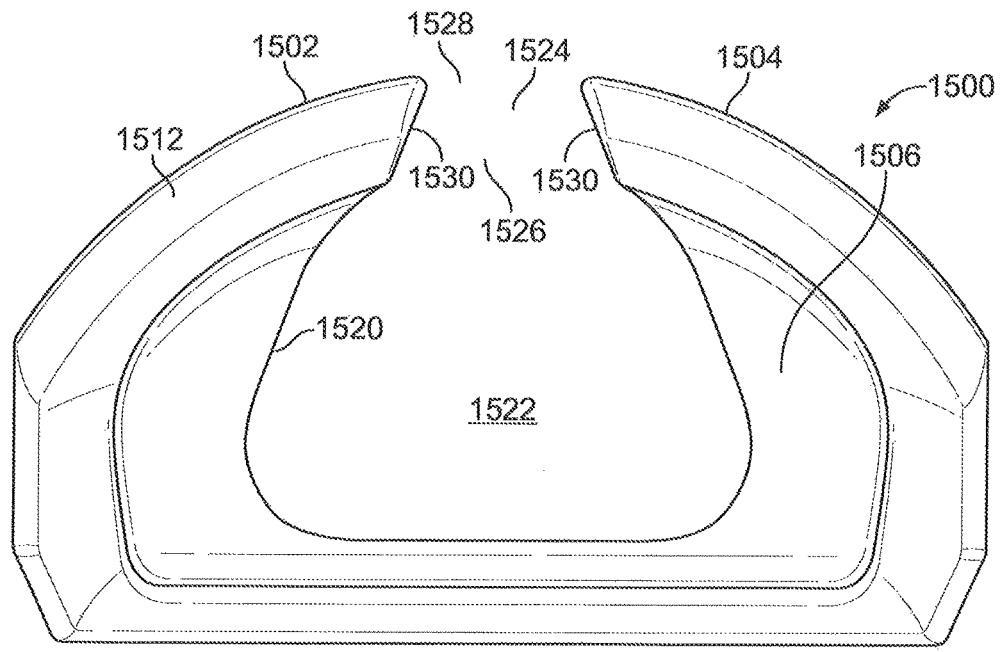
FIG. 13D illustrates a bottom view of the keyed-type augment component shown in FIG. 13A.
Figure 13E:
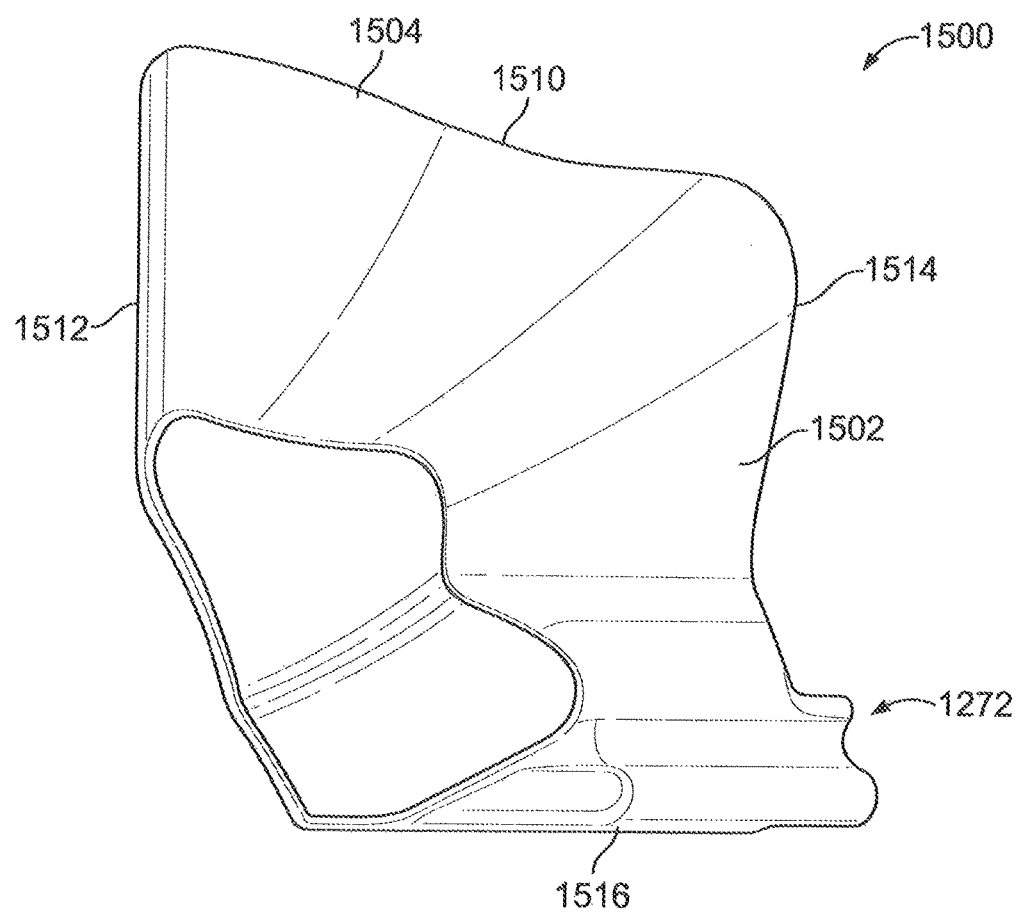
FIG. 13E illustrates a side view of the keyed-type augment component shown in FIG. 13A.

As shown in at least FIG. 13C, the top side portion 1514 of the augment wall 1502 can include a first opening 1518 that is at least partially defined by an opening wall 1520 and is in communication with at least the internal cavity 1508. The first opening 1518 can be sized to accommodate passage of the body segment 1030, 1030', 1224 of the neck portion 1010, 1208, 1306 through the first opening 1518 at least when a portion of the face segment 1032, 1032', 1226, 1308 is operably positioned in the internal cavity 1508. According to the illustrated embodiment, the first opening 1518 has a generally trapezoidal shape, with the trapezoidal shape extending outwardly as the first opening 1518 extends in the general direction of the front side portion 1516 of the augment wall 1502. Further, in at least a manner similar to that described above with respect to at least the first openings 1090, 1264 and augment components 1004, 1202 shown in at least FIGS. 9A and 10A, the first opening 1518 can be sized and/or shaped to accommodate linear and/or angular adjustment of the position of the body segment 1030, 1030', 1224 within the first opening 1518, and thereby accommodate a relatively wide range of angulation between the blade component 1006' and the augment component 1500. Thus, when the body segment 1030, 1030', 1224 is operably positioned in the first opening 1518, such a configuration of the first opening 1518, as well as the shape and/or size of the body segment 1030, 1030', 1224 can at least accommodate pivotal and/or rotational displacement of the body segment 1030, 1030', 1224, and thus of the blade component 1006', relative to the centered, neutral position of the blade component 1006, 1006', 1204, 1304 or similar central, neutral position of the blade component 1006, 1006', 1204, 1304. Such angular adjustment(s) of the blade component 1006' as well as linear adjustments, relative to the augment component 1500 can be in a manner that is similar to that previously illustrated and discussed with respect to the exemplary adjustment of the position of the centerlines 1012, 1268 depicted in at least FIGS. 9A and 10A.

Additionally, similar to the previously discussed first openings 1090, 1264, 1338, 1422 and face segments 1032, 1032', 1226, 1308, at least the first opening 1528 of the augment component 1500 depicted in at least FIG. 13A can also have a size and/or shape that prevents the passage of the face segment 1032, 1032', 1226, 1308 through the first opening 1338.

The bottom side portion 1512, as shown in at least FIG. 12D, can be configured to abut, or otherwise be positioned proximally adjacent to, the acetabular cup or shell 1000, and generally defines a second opening 1522 in the augment component 1500. Similar to at least the previously discussed second openings 1108, 1276, the second opening 1522 is in fluid communication with the internal cavity 1508 and sized to accommodate the face segment 1032, 1032', 1226, 1308 of the blade component 1006, 1006', 1204, 1304 being in direct contact with the acetabular cup or shell 1000.

As shown in at least FIGS. 13A-13D, the augment component 1500 also includes a slot 1524 that is sized to receive insertion of the body segment 1030, 1030', 1224. Similar to at least the slot 1344 depicted in FIG. 11A, the slot 1524 can be positioned at the back side portion 1510 of the augment wall 1502. Further, according to certain embodiments, the passage provided by the slot 1524 to at least the first opening 1518 can be generally defined by tapered slot walls 1350 such that a second end 1526 of the slot 1524 is larger than the first end 1528 of the slot 1524. Accordingly, the slot 1524 and the first opening 1528 can, be sized and/or shaped, among other shapes and configurations, to control the insertion/removal of the body segment 1030, 1030', 1224 into/from the slot 1524 and the first opening 1528 in a manner similar to that previously discussed with respect to the slots 1278, 1344 and first opening 1264, 1346. However, the slot 1524 can also be sized to receive the body segment 1030, 1030', 1224 in a variety of other manners.

Additionally, as shown in at least FIG. 13A, in addition to the tapered walls 1530 being generally tapered in the direction of the first opening 1518, at least a portion of the tapered walls 1530, as indicate by tapered wall segments 1530a can also be outwardly tapered in the general direction of the top side portion 1514 of augment wall 1502.

The modular variable blade augments 1002, 1200, 1300, 1400 can be implanted in a patient using a variety of different methods or techniques. For example, according to certain embodiments in which the augment component 1004, 1202, 1302, 1500 and the blade component 1006, 1006', 1204, 1304 are separate components that are assembled during the implantation procedure, the augment component 1004, 1202, 1302, 1500 and the blade component 1006, 1006', 1204, 1304 can be implanted or otherwise positioned in the patient prior to implantation of the acetabular cup or shell 1000. According to such an method, after preparation of the acetabulum and any bone defects or other bone losses in the area, trial components for both of the acetabular cup or shell 1000 and the blade component 1006, 1006', 1204, 1304 can be used to at least assist in determining a sizing and positioning of at least those implant devices. With the sizing and positioning generally determined, and the trial component for the blade component can be replaced by a blade component 1006, 1006', 1204, 1304 having the selected size that is to be implanted in the patient. The selected blade component 1006, 1006', 1204, 1304 can then be placed at the determined position along the host bone. Further, optionally, as discussed above, the blade component 1006, 1006', 1204, 1304 can have one or more provisional holes that can receive a provisional pin that is driven into at least a portion of the bone of the patient so as to at least assist in temporarily securing the blade component 1006, 1006', 1204, 1304 at the selected position.

With the blade component 1006, 1006', 1204, 1304 at the selected position, and which may be at least temporarily secured at that position via the use of the provisional pin(s), the augment component 1004, 1202, 1302, 1500 can be positioned so that at least the body segment 1030, 1030', 1224 is positioned in the first opening 1090, 1264, 1338, 1422, 1518 of the augment component 1004, 1202, 1302, 1500. With the augment component 1004, 1202, 1302, 1500 at a selected position relative to at least the blade component 1006, 1006', 1204, 1304, the position of the augment component 1004, 1202, 1302, 1500 can be secured by the placement of provisional pins through the provisional holes 1078 in the augment component 1004, 1202, 1302, 1500 that extend into at least a portion of the bone. Such securing of the positioning of the augment component 1004, 1202, 1302, 1500 can also at least assist in re-establishing the acetabular rim.

With the augment component 1004, 1202, 1302, 1500 positioned about the blade component 1006, 1006', 1204, 1304 and secured in position by at least the use of the provisional pin(s), the trial acetabular cup or shell can be removed and replaced by the acetabular cup or shell 1000 that will be implanted into the patient. According to such a procedure, after removal of the trial acetabular cup or shell, the acetabular cup or shell 1000 that is to be implanted into the patient can be impacted and fixed into position in/along the host bone. With the acetabular cup or shell 1000 fixed in position, the position of the augment component 1004, 1202, 1302, 1500 and/or the blade component 1006, 1006', 1204, 1304 can be verified. Such verification can, according to certain embodiments, include determining that the augment component 1004, 1202, 1302, 1500 and/or the blade component 1006, 1006', 1204, 1304 are properly positioned, which can include confirming that at least a portion of the blade component 1006, 1006', 1204, 1304, such as the face segment 1032, 1032', 1226, 1308, is in direct contact with the acetabular cup or shell 1000. With the positions of the components of the modular variable blade augments 1002, 1200, 1300, 1400 verified and the acetabular cup or shell 1000 fixed in position, locking and/or non-locking bone screws can be received into the fixation holes 1024 in the blade component 1006, 1006', 1204, 1304 and into the host bone so as to at least partially secure the blade component 1006, 1006', 1204, 1304 at the selected position on the host bone. Fixation material, such as bone cement, can then be injected into the augment component 1004, 1202, 1302, 1500, such as into the internal cavity 1048, 1234, 1328, 1410, 1508, so as to unitize the components of the modular variable blade augments 1002, 1200, 1300, 1400 and the acetabular cup or shell 1000. Such fixation material can also be used to fill in space, if any, remaining at the top of the augment component 1004, 1202, 1302, 1500.

According to other embodiments in which the augment component 1004, 1202, 1302, 1500 and the blade component 1006, 1006', 1204, 1304 are separate components that are assembled during the implantation procedure, the acetabular cup or shell 1000 can be implanted or otherwise positioned in the patient prior to implantation of the augment component 1004, 1202, 1302, 1500 and the blade component 1006, 1006', 1204, 1304. According to such an method, after preparation of the acetabulum and any bone defects or other bone losses in the area, trial components for both of the acetabular cup or shell 1000 and the blade component 1006, 1006', 1204, 1304 can be used to at least assist in determining a sizing and positioning of at least those implant devices. With the sizing and positioning generally determined, the trial component for the acetabular cup or shell 1000 can be replaced with the acetabular cup or shell 1000 that will be implanted. The acetabular cup or shell 1000 can then be impacted and fixed into position in/along the host bone.

With the acetabular cup or shell 1000 fixed in position, the components of the modular variable blade augments 1002, 1200, 1300, 1400 can be assembled and placed into position. For example, the trial blade component can be removed and replaced with a blade component 1006, 1006', 1204, 1304 having a selected size. Moreover, the selected blade component 1006, 1006', 1204, 1304 can be placed at the determined position along the host bone. Further, optionally, as discussed above, the blade component 1006, 1006', 1204, 1304 can have one or more provisional holes that can receive a provisional pin that is driven into at least a portion of the bone of the patient so as to at least assist in temporarily securing the blade component 1006, 1006', 1204, 1304 at the selected position. Such positioning can include positioning the blade component 1006, 1006', 1204, 1304 such that at least a portion of the blade component 1006, 1006', 1204, 1304, such as the face segment 1032, 1032', 1226, 1308, is in direct contact with the acetabular cup or shell 1000. The augment component 1004, 1202, 1302, 1500 can then be positioned so that at least the body segment 1030, 1030', 1224 is positioned in the first opening 1090, 1264, 1338, 1422, 1518 of the augment component 1004, 1202, 1302, 1500. With the augment component 1004, 1202, 1302, 1500 at a selected position relative to at least the blade component 1006, 1006', 1204, 1304, the position of the augment component 1004, 1202, 1302, 1500 can be secured by the placement of provisional pins through the provisional holes 1078 in the augment component 1004, 1202, 1302, 1500 that extend into at least a portion of the bone. The position of the augment component 1004, 1202, 1302, 1500 and/or the blade component 1006, 1006', 1204, 1304 can then be verified, which can include verifying that the face segment 1032, 1032', 1226, 1308 of the blade component 1006, 1006', 1204, 1304 is in direct contact with the acetabular cup or shell 1000.

With the positions of the components of the modular variable blade augments 1002, 1200, 1300, 1400 verified and the acetabular cup or shell 1000 fixed in position, locking and/or non-locking bone screws can be received into the fixation holes 1024 in the blade component 1006, 1006', 1204, 1304 and into the host bone so as to at least partially secure the blade component 1006, 1006', 1204, 1304 at the selected position on the host bone. Fixation material, such as bone cement, can then be injected into the augment component 1004, 1202, 1302, 1500, such as into the internal cavity 1048, 1234, 1328, 1410, 1508, so as to unitize the components of the modular variable blade augments 1002, 1200, 1300, 1400 and the acetabular cup or shell 1000. Such fixation material can also be used to fill in space, if any, remaining at the top of the augment component 1004, 1202, 1302, 1500.

In one form of the invention, an implantable variable angle blade augment is provided to support an acetabular shell, and includes a blade component and an augment component. The blade component includes a buttress portion and a neck portion, with the neck portion having a body segment and a face segment. The augment component having a first opening extending through a top side portion of the augment component and a second opening extending through a bottom side portion of the augment component, the first opening and the second opening being on opposing sides of, and in fluid communication with, an internal cavity of the augment component, the first opening sized to accommodate selective adjustment of at least one of a linear orientation and an angular orientation of the blade component relative to the augment component when the body segment is positioned in the first opening, the neck portion having a length that is sized to position, when the body segment is positioned in the first opening, the face segment at a location at least proximally adjacent to the second opening such that, when the bottom side portion is positioned adjacent to the acetabular shell, a portion of the face segment directly engages an outer surface of the acetabular shell.

In another form of the invention, an implant system is provided which includes an acetabular shell having an outer surface, and a variable blade augment. The variable blade augment includes a blade component and an augment component. The blade component has a buttress portion and a neck portion, with the neck portion having a body segment and a face segment. The augment component has a first opening extending through a top side portion of the augment component and a second opening extending through a bottom side portion of the augment component, with the top and bottom sides being on opposing sides of the augment component, and with the bottom side shaped for mating engagement with the outer surface of the acetabular shell. The first opening and the second opening are in fluid communication with an internal cavity of the augment component, with the first opening sized and shaped to receive at least a portion of the body segment and accommodate selective adjustment of at least one of a linear orientation and an angular orientation of the blade component relative to the augment component when the body segment is positioned in the first opening. The neck portion has a length that is sized to extend the body segment through the first opening and into the internal cavity by a length that positions a portion of the face segment at a location that is at least proximally adjacent to the second opening such that, when the bottom side portion is positioned adjacent to the acetabular shell, a portion of the face segment directly contacts the outer surface of the acetabular shell.

In a further form of the invention, a variable angle blade augment is provided and which includes an augment section and a blade segment. The augment section is structured to abut against at least an outer surface of a component of an implantable medical device, and with a reservoir of the augment section structured to receive injection of an adhesive that is configured to unitize at least the augment section with the component of the implantable medical device. The blade segment includes a body segment and an extension, with the extension having a first connector adapted for pivotal displacement about an aperture of the augment section, and with at least a portion of the first connector structured to be secured to the augment section by a mechanical connection, and wherein at least a portion of the blade segment has a length sized to extend through the augment section and directly contact the component of the implantable medical device.

In one aspect of the invention, the first opening includes a first sidewall and a second sidewall, with the first and second sidewalls positioned on opposing sides of the first opening, wherein a portion of the first sidewall is separated from the second sidewall by a linear distance having a length sized to receive passage of the face segment through the first opening, and wherein linear distances between other portions of the first and second sidewalls cannot accommodate passage of the face portion through the first opening.

In another aspect of the invention, the first sidewall includes a notch that outwardly extends from a portion of the first sidewall, and with the linear distance between a portion of the notch and the second sidewall having the length sized to receive passage of the face segment through the first opening.

In a further aspect of the invention, the face segment has a length between a first sidewall and a second sidewall of the face segment that is greater than the linear distance between a portion of the notch and the second sidewall that is sized receive passage of the face segment through the first opening, and wherein at least a portion of the portion of the face segment that is contoured for the mating engagement with the acetabular shell being positioned between the first and second sidewalls of the face segment.

In a further aspect of the invention, the at least a portion of a bone facing outer surface of the augment component includes a retention lip that at least outwardly projects from another proximally adjacent portion of the bone facing outer surface, and wherein the retention lip is structured to provide a barrier to a flow of bone cement.

In a further aspect of the invention, the neck portion further includes a ridge that extends along a length of an outer surface of at least a portion of the body segment, and with the ridge outwardly projecting from adjacent portions of the outer surface and structured to enhance a strength of the neck portion when the neck portion is subjected to a bending moment.

In a further aspect of the invention, the augment component further defines at least one cement delivery port in fluid communication with the internal cavity.

In a further aspect of the invention, the augment component includes a slot that extends through an outer surface of the augment component at either a back side portion or a front side portion of the augment component, wherein the slot is in fluid communication with the first opening, and wherein the first opening is sized to prevent passage of the face segment through the first opening.

In a further aspect of the invention, the body segment includes a back side, a front side, a first sidewall, and a second sidewall, with the first and second sidewalls positioned on opposing sides of the body segment and separated by a first width, and the back and front sides positioned on opposing sides of the body segment and separated by a second width, and wherein the slot is sized to accommodate passage of the body segment to the first opening for only one of the first and second widths.

In a further aspect of the invention, the slot is defined by a first slot wall and a second slot wall, with the first and second slot walls being tapered from a first end to a second end, and a distance between the first and second slot walls at the first end being lesser than a distance between the first and second sidewalls at the second end, and wherein the first end is smaller than only one of the first and second widths of the body segment.

In a further aspect of the invention, the at least a portion of the first and second slot walls are tapered in at least two different directions.

In a further aspect of the invention, the augment component includes a slot having a shape that mates with a profile of the face segment, and with the slot being in fluid communication with the first opening and the internal cavity of the augment component.

Various features and advantages of the present invention are set forth in the following claims. Additionally, changes and modifications to the described embodiments described herein will be apparent to those skilled in the art, and such changes and modifications can be made without departing from the spirit and scope of the present invention and without diminishing its intended advantages. While the present invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

While the invention has been described with reference to certain embodiments, it should be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An implantable variable angle blade augment structured to support an acetabular shell, the variable angle blade augment comprising:
   a blade component having a buttress portion and a neck portion, the neck portion having a body segment and a face segment; and
   an augment component having a first opening extending through a top side portion of the augment component and a second opening extending through a bottom side portion of the augment component, the first opening and the second opening being on opposing sides of, and in fluid communication with, an internal cavity of the augment component, the first opening sized to accommodate selective adjustment of at least one of a linear orientation and an angular orientation of the blade component relative to the augment component when the body segment is positioned in the first opening, the neck portion having a length that is sized to position, when the body segment is positioned in the first opening, the face segment at a location at least proximally adjacent to the second opening such that, when the bottom side portion is positioned adjacent to the acetabular shell, a portion of the face segment directly engages an outer surface of the acetabular shell.

2. The variable angle blade augment of claim 1, wherein the first opening includes a first sidewall and a second sidewall, the first and second sidewalls positioned on opposing sides of the first opening, wherein a portion of the first sidewall is separated from the second sidewall by a linear distance having a length sized to receive passage of the face segment through the first opening, and further wherein linear distances between other portions of the first and second sidewalls cannot accommodate passage of the face portion through the first opening.

3. The variable angle blade augment of claim 2, wherein the first sidewall includes a notch that outwardly extends from a portion of the first sidewall, the linear distance between a portion of the notch and the second sidewall having the length sized to receive passage of the face segment through the first opening.

4. The variable angle blade augment of claim 3, wherein the face segment has a length between a first sidewall and a second sidewall of the face segment that is greater than the linear distance between a portion of the notch and the second sidewall that is sized receive passage of the face segment through the first opening, and wherein at least a portion of the portion of the face segment that is contoured for the mating engagement with the acetabular shell being positioned between the first and second sidewalls of the face segment.

5. The variable angle blade augment of claim 2, wherein at least a portion of a bone facing outer surface of the augment component includes a retention lip that at least outwardly projects from another proximally adjacent portion of the bone facing outer surface, and wherein the retention lip is structured to provide a barrier to a flow of bone cement.

6. The variable angle blade augment of claim 2, wherein the neck portion further includes a ridge that extends along a length of an outer surface of at least a portion of the body segment, the ridge outwardly projecting from adjacent portions of the outer surface and structured to enhance a strength of the neck portion when the neck portion is subjected to a bending moment.

7. The variable angle blade augment of claim 2, wherein the augment component further defines at least one cement delivery port in fluid communication with the internal cavity.

8. The variable angle blade augment of claim 2, wherein the augment component includes a slot that extends through an outer surface of the augment component at either a back side portion or a front side portion of the augment component, the slot being in fluid communication with the first opening, and wherein the first opening is sized to prevent passage of the face segment through the first opening.

9. The variable angle blade augment of claim 8, wherein the body segment includes a back side, a front side, a first sidewall, and a second sidewall, the first and second sidewalls positioned on opposing sides of the body segment and separated by a first width, the back and front sides positioned on opposing sides of the body segment and separated by a second width, and wherein the slot is sized to accommodate passage of the body segment to the first opening for only one of the first and second widths.

10. The variable angle blade augment of claim 9, wherein the slot is defined by a first slot wall and a second slot wall, the first and second slot walls being tapered from a first end to a second end, a distance between the first and second slot walls at the first end being lesser than a distance between the first and second sidewalls at the second end, and wherein the first end is smaller than only one of the first and second widths of the body segment.

11. The variable angle blade augment of claim 10, wherein at least a portion of the first and second slot walls are tapered in at least two different directions.

12. The variable angle blade augment of claim 2, wherein the augment component includes a slot having a shape that mates with a profile of the face segment, the slot being in fluid communication with the first opening and the internal cavity of the augment component.

13. An implant system, comprising:
an acetabular shell having an outer surface; and
a variable blade augment including:
   a blade component having a buttress portion and a neck portion, the neck portion having a body segment and a face segment; and
   an augment component having a first opening extending through a top side portion of the augment component and a second opening extending through a bottom side portion of the augment component, the top and bottom sides being on opposing sides of the augment component, the bottom side shaped for mating engagement with the outer surface of the acetabular shell, the first opening and the second opening being in fluid communication with an internal cavity of the augment component, the first opening sized and shaped to receive at least a portion of the body segment and accommodate selective adjustment of at least one of a linear orientation and an angular orientation of the blade component relative to the augment component when the body segment is positioned in the first opening, the neck portion having a length that is sized to extend the body segment through the first opening and into the internal cavity by a length that positions a portion of the face segment at a location that is at least proximally adjacent to the second opening such that, when the bottom side portion is positioned adjacent to the acetabular shell, a portion of the face segment directly contacts the outer surface of the acetabular shell.

14. The implant system of claim 13, wherein the first opening includes a first sidewall and a second sidewall, the first and second sidewalls positioned on opposing sides of the first opening, wherein a portion of the first sidewall is separated from the second sidewall by a linear distance having a length sized to receive passage of the face segment through the first opening, and further wherein linear distances between other portions of the first and second sidewalls cannot accommodate passage of the face portion through the first opening.

15. The implant system of claim 14, wherein the face segment has a length between a first sidewall and a second sidewall of the face segment that is greater than a linear distance between a portion of the first and second sidewalls that is sized to receive passage of the face segment through the first opening, and wherein at least a portion of the portion of the face segment that is contoured for the mating engagement with the outer surface of the acetabular shell is positioned between the first and second sidewalls of the face segment.

16. The implant system of claim 13, wherein at least a portion of a bone facing outer surface of the augment component includes a retention lip that at least outwardly projects from another proximally adjacent portion of the bone facing outer surface, and wherein the retention lip is structured to provide a barrier to a flow of bone cement.

17. The implant system of claim 13, wherein the neck portion further includes a ridge that extends along a length of an outer surface of at least a portion of the body segment, the ridge outwardly projecting from adjacent portions of the outer surface and structured to enhance a strength of the neck portion when the neck portion is subjected to a bending moment.

18. The implant system of claim 13, wherein the augment component includes at least one cement delivery port in fluid communication with the internal cavity.

19. The implant system of claim 13, wherein the augment component includes a slot that extends through an outer surface of the augment component at either a back side portion or a front side portion of the augment component, wherein the slot is in fluid communication with the first opening, and wherein the first opening is sized to prevent passage of the face segment through the first opening.

20. The implant system of claim 19, wherein the body segment includes a back side, a front side, a first sidewall, and a second sidewall, the first and second sidewalls positioned on opposing sides of the body segment and separated by a first width, the back and front sides positioned on opposing sides of the body segment and separated by a second width, and wherein the slot is sized to accommodate passage of the body segment to the first opening for only one of the first and second widths.

21. The implant system of claim 20, wherein the slot is defined by a first slot wall and a second slot wall, the first and second slot walls being tapered from a first end to a second end, a distance between the first and second slot walls at the first end being lesser than a distance between the first and second sidewalls at the second end, and wherein the first end is smaller than only one of the first and second widths of the body segment.

22. The implant system of claim 21, wherein at least a portion of the first and second slot walls are tapered in two different directions.

23. The implant system of claim 13, wherein the augment component includes a slot having a shape that mates with a profile of the face segment, and wherein the slot is in fluid communication with the first opening and the internal cavity of the augment component.

24. A variable angle blade augment, comprising:
   an augment section structured to abut against at least an outer surface of a component of an implantable medical device, a reservoir of the augment section structured to receive injection of an adhesive that is configured to unitize at least the augment section with the component of the implantable medical device; and
   a blade segment including a body segment and an extension, the extension having a first connector adapted for pivotal displacement about an aperture of the augment section, wherein at least a portion of the first connector is structured to be secured to the augment section by a mechanical connection, and further wherein at least a portion of the blade segment has a length sized to extend through the augment section and directly contact the component of the implantable medical device.

* * * * *